(12) United States Patent
Feingold et al.

(10) Patent No.: US 7,603,201 B2
(45) Date of Patent: Oct. 13, 2009

(54) SYSTEMS AND METHODS FOR THE AUTOMATED PRE-TREATMENT AND PROCESSING OF BIOLOGICAL SAMPLES

(75) Inventors: Gordon Alan Feingold, Santa Barbara, CA (US); James B. Gilmartin, Los Alamos, CA (US); Mark Richard Holbrook, Fort Collins, CO (US); John A. Favuzzi, Santa Barbara, CA (US); Marc E. Key, Ojai, CA (US)

(73) Assignee: Dako Denmark A/S, Glostrup (DK)

( * ) Notice: Subject to any disclaimer, the term of this patent is extended or adjusted under 35 U.S.C. 154(b) by 39 days.

(21) Appl. No.: 11/338,524

(22) Filed: Jan. 23, 2006

(65) Prior Publication Data

US 2007/0010912 A1 Jan. 11, 2007

Related U.S. Application Data

(60) Division of application No. 11/229,098, filed on Sep. 16, 2005, each and a continuation of application No. 10/741,628, filed on Dec. 19, 2003, each and a continuation-in-part of application No. 10/731,316, filed on Dec. 8, 2003, application No. 11/338,524, which is a continuation-in-part of application No. 11/119,417, filed on Apr. 30, 2005, now abandoned, which is a continuation of application No. PCT/DK03/08771, filed on Dec. 15, 2003, application No. 11/338,524, which is a continuation-in-part of application No. 11/156,760, filed on Jun. 20, 2005, and a continuation-in-part of application No. PCT/DK2003/000877, filed on Dec. 15, 2003, and a continuation-in-part of application No. PCT/DK2003/000911, filed on Dec. 19, 2003, and a continuation-in-part of application No. PCT/US2003/040518, filed on Dec. 19, 2003, and a continuation-in-part of application No. PCT/US2003/040591, filed on Dec. 19, 2003, and a continuation-in-part of application No. PCT/US2003/040520, filed on Dec. 19, 2003, and a continuation-in-part of application No. PCT/US2003/040974, filed on Dec. 19, 2003, and a continuation-in-part of application No. PCT/US2003/040519, filed on Dec. 19, 2003, and a continuation-in-part of application No. PCT/US2003/041022, filed on Dec. 22, 2003, and a continuation-in-part of application No. PCT/US2003/040880, filed on Dec. 22, 2003, and a continuation-in-part of application No. PCT/US2005/006383, filed on Feb. 28, 2005.

(60) Provisional application No. 60/697,591, filed on Jul. 7, 2005, provisional application No. 60/697,813, filed on Jul. 7, 2005.

(51) Int. Cl.
*G06F 19/00* (2006.01)

(52) U.S. Cl. .............................. 700/245; 700/1; 700/95; 700/108; 422/63; 422/65; 435/286.4; 435/287.3; 702/182

(58) Field of Classification Search ................. 700/245, 700/1, 95, 108; 702/182; 422/63, 65; 435/286.4, 435/287.3
See application file for complete search history.

(56) References Cited

U.S. PATENT DOCUMENTS

| | | | |
|---|---|---|---|
| 4,311,667 | A | 1/1982 | Gocho |
| 4,967,606 | A | 11/1990 | Wells et al. |
| 5,068,091 | A | 11/1991 | Toya |
| 5,073,504 | A | 12/1991 | Bogen |
| 5,289,385 | A | 2/1994 | Grandone |
| 5,338,358 | A | 8/1994 | Mizusawa et al. |
| 5,346,672 | A | 9/1994 | Stapleton et al. |
| 5,355,439 | A | 10/1994 | Bernstein et al. |
| 5,380,486 | A | 1/1995 | Anami |
| 5,399,316 | A | 3/1995 | Yamada |
| 5,425,918 | A | 6/1995 | Healey et al. |
| 5,439,649 | A | 8/1995 | Tseung et al. |
| 5,552,087 | A | 9/1996 | Zeheb et al. |
| 5,573,727 | A | 11/1996 | Keefe |
| 5,578,452 | A | 11/1996 | Shi et al. |
| 5,595,707 | A | 1/1997 | Copeland et al. |
| 5,646,049 | A | 7/1997 | Tayi |
| 5,650,327 | A | 7/1997 | Copeland et al. |

SCS ROBOT SCHEDULER BLOCK DIAGRAM
2010

| | | | |
|---|---|---|---|
| 5,654,199 A | 8/1997 | Copeland et al. | |
| 5,654,200 A | 8/1997 | Copeland et al. | |
| 5,696,887 A | 12/1997 | Bernstein et al. | |
| 5,839,091 A | 11/1998 | Rhett et al. | |
| 5,896,488 A | 4/1999 | Jeong | |
| 5,948,359 A | 9/1999 | Kalra et al. | |
| 5,963,368 A | 10/1999 | Domanik et al. | |
| 6,045,759 A | 4/2000 | Ford et al. | |
| 6,080,363 A | 6/2000 | Takahashi et al. | |
| 6,093,574 A | 7/2000 | Druyor-Sanchez et al. | |
| 6,096,271 A | 8/2000 | Bogen et al. | |
| 6,296,809 B1 * | 10/2001 | Richards et al. | 422/64 |
| 6,349,264 B1 | 2/2002 | Rhett et al. | |
| 6,352,861 B1 | 3/2002 | Copeland et al. | |
| 6,403,036 B1 | 6/2002 | Rodgers et al. | |
| 6,403,931 B1 | 6/2002 | Showalter et al. | |
| 6,405,609 B1 | 6/2002 | Richards et al. | |
| 6,451,551 B1 | 9/2002 | Zhan et al. | |
| 6,472,217 B1 | 10/2002 | Richards et al. | |
| 6,495,106 B1 | 12/2002 | Kalra et al. | |
| 6,534,008 B1 * | 3/2003 | Angros | 422/64 |
| 6,544,798 B1 | 4/2003 | Christensen et al. | |
| 6,582,962 B1 | 6/2003 | Richards et al. | |
| 6,632,598 B1 | 10/2003 | Zhang et al. | |
| 6,635,225 B1 | 10/2003 | Thiem et al. | |
| 6,735,531 B2 | 5/2004 | Rhett et al. | |
| 6,746,851 B1 * | 6/2004 | Tseung et al. | 435/40.5 |
| 6,821,072 B2 | 11/2004 | Thiem et al. | |
| 6,855,292 B2 * | 2/2005 | Angros | 422/64 |
| 6,855,559 B1 | 2/2005 | Christensen et al. | |
| 7,135,992 B2 | 11/2006 | Karlsson et al. | |
| 7,142,852 B2 | 11/2006 | Tell et al. | |
| 7,396,508 B1 * | 7/2008 | Richards et al. | 422/64 |
| 7,404,927 B2 * | 7/2008 | Lemme et al. | 422/64 |
| 2002/0001849 A1 | 1/2002 | Copeland et al. | |
| 2002/0072122 A1 | 6/2002 | Copeland et al. | |
| 2002/0114733 A1 | 8/2002 | Copeland et al. | |
| 2003/0099573 A1 | 5/2003 | Tseung et al. | |
| 2003/0100043 A1 | 5/2003 | Kalra et al. | |
| 2003/0120633 A1 | 6/2003 | Torre-Bueno | |
| 2004/0033163 A1 | 2/2004 | Tseung et al. | |
| 2004/0219069 A1 | 11/2004 | Kalra et al. | |
| 2004/0265185 A1 | 12/2004 | Kitagawa | |
| 2004/0266015 A1 | 12/2004 | Favuzzi et al. | |
| 2005/0038676 A1 | 2/2005 | Showalter et al. | |
| 2005/0064535 A1 | 3/2005 | Favuzzi et al. | |
| 2005/0124028 A1 | 6/2005 | Windeyer et al. | |
| 2005/0159982 A1 | 7/2005 | Showalter et al. | |
| 2006/0045806 A1 | 3/2006 | Winther et al. | |
| 2006/0046298 A1 | 3/2006 | Key et al. | |
| 2006/0063265 A1 | 3/2006 | Welcher et al. | |
| 2006/0085140 A1 | 4/2006 | Feingold et al. | |
| 2006/0088928 A1 | 4/2006 | Sweet et al. | |
| 2006/0088940 A1 | 4/2006 | Feingold et al. | |
| 2006/0105359 A1 | 5/2006 | Favuzzi et al. | |
| 2006/0148063 A1 * | 7/2006 | Fauzzi et al. | 435/286.4 |
| 2006/0178776 A1 * | 8/2006 | Feingold et al. | 700/245 |
| 2006/0265133 A1 | 11/2006 | Cocks et al. | |
| 2007/0010911 A1 * | 1/2007 | Feingold et al. | 700/245 |
| 2007/0010912 A1 | 1/2007 | Feingold et al. | |
| 2007/0196909 A1 | 8/2007 | Showalter et al. | |
| 2007/0231889 A1 * | 10/2007 | Angros | 435/308.1 |

FOREIGN PATENT DOCUMENTS

| | | |
|---|---|---|
| DE | 4313807 | 11/1993 |
| JP | 03209163 A2 | 12/1991 |
| WO | WO 95/10035 | 4/1995 |
| WO | WO 97/26541 | 7/1997 |
| WO | WO 99/43434 | 9/1999 |
| WO | WO 00/02660 | 1/2000 |
| WO | WO 01/51909 | 7/2001 |
| WO | WO 01/68259 | 9/2001 |
| WO | WO 01/88500 | 11/2001 |
| WO | WO 02/056121 | 7/2002 |
| WO | WO 03/045560 | 6/2003 |
| WO | WO 03/052386 | 6/2003 |
| WO | WO 2004/074845 | 9/2004 |
| WO | WO 2004/074847 | 9/2004 |
| WO | WO 2005/031312 | 4/2005 |

* cited by examiner

*Primary Examiner*—Khoi Tran
*Assistant Examiner*—McDieunel Marc
(74) *Attorney, Agent, or Firm*—Finnegan, Henderson, Farabow, Garrett & Dunner, L.L.P.

(57) ABSTRACT

Systems and methods allowing for the automatic control and scheduling of a staining apparatus for biological samples on slides present within the apparatus. In some embodiments, the actions of a robot coupled to the staining apparatus, which performs some of the staining tasks on the individual slides in accordance with their respective protocols, may be prioritized and scheduled. In some embodiments, the scheduling may result in increasing or maximizing the throughput of slides. In some embodiments, robot scheduling ensures that the individual slides are processed substantially within the tolerances specified by their respective protocols. In some embodiments, the robot scheduler may respond to spontaneous user actions and adaptively schedule or re-schedule robot actions.

37 Claims, 29 Drawing Sheets

SMS LOGICAL DATA MODEL (contd.)
1800

STAINER CONTROL SOFTWARE BLOCK DIAGRAM

SCS Communications Subsystem Block Diagram
1920

SCS STAINER API BLOCK DIAGRAM
2000

SYSTEMS AND METHODS FOR THE AUTOMATED PRE-TREATMENT AND PROCESSING OF BIOLOGICAL SAMPLES

CROSS REFERENCES TO RELATED APPLICATIONS

This application is a continuation of U.S. application Ser. No. 11/229,098, entitled "Systems and Methods for the Automated Pre-Treatment and Processing of Biological Samples," filed Sep. 16, 2005, which is incorporated herein by reference in its entirety.

This application claims priority to Provisional Patent Application 60/697,591, filed on Jul. 7, 2005 and Provisional Patent Application 60/697,813, filed on Jul. 7, 2005, which are herein incorporated by reference in their entirety.

This application is a continuation of U.S. patent application Ser. No. 11/229,098, filed on Sep. 16, 2005, which is a continuation-in-part of U.S. patent application Ser. No. 10/741,628, filed on Dec. 19, 2003 and of U.S. patent application Ser. No. 10/731,316, filed on Dec. 8, 2003, both of which claim priority to U.S. Provisional Application No. 60/435,601, filed on Dec. 20, 2002, all of which are herein incorporated by reference in their entirety.

This application is also a continuation-in-part of U.S. patent application Ser. No. 11/119,417, filed on Apr. 30, 2005, which is a continuation-in-part of international application PCT/DK2003/000877, having an international filing date of Dec. 15, 2003 and designating the United States of America, which claims priority to U.S. Provisional Application No. 60/435,601, filed on Dec.20, 2002, all of which are herein incorporated by reference in their entirety. This application is also a continuation-in-part of U.S. patent application Ser. No. 11/156,760, filed on Jun. 20, 2005, which is herein incorporated by reference in its entirety.

This application is a continuation-in-part of the folowing international applications: PCT/DK2003/000877, having an international filing date of Dec. 15, 2003 and designating the United States of America; PCT/DK2003/000911, having an international filing date of Dec. 19, 2003 and designating the United States of America; PCT/US2003/040518, having an international filing date of Dec. 19, 2003 and designating the United States of America; PCT/US2003/040591, having an international filing date of Dec. 19, 2003 and designating the United States of America; PCT/US2003/040520, having an international filing date of Dec. 19, 2003 and designating the United States of America; PCT/US2003/040974, having an international filing date of Dec. 19, 2003 and designating the United States of America; PCT/US2003/040519, having an international filing date of Dec. 19, 2003 and designating the United States of America; PCT/US2003/041022, having an international filing date of Dec. 22, 2003 and designating the United States of America; and PCT/US2003/040880, having an international filing date of Dec. 22, 2003 and designating the United States of America; all of which claim priority to U.S. Provisional Application No. 60/435,601, filed on Dec. 20, 2002, all of which are herein incorporated by reference in their entirety. This application is also a continuation-in-part of PCT/US2005/006383, having an international filing date of Feb. 28, 2005 and designating the United States of America, which claims priority to U.S. Provisional Application 60/549,889, filed on Mar. 2, 2004, both of which are herein incorporated by reference in their entirety.

U.S. patent application Ser. No. 11/227,270, filed on Sep. 16, 2005, is herein incorporated by reference in its entirety.

This application is also related to European Patent Office Application 03076463.3 filed on May 14, 2003. Each of the above-referenced patent applications is incorporated herein by reference, in its entirety. Each of the patent application publications corresponding to the above-referenced international applications is also incorporated herein by reference in its entirety, said patent application publications being, namely: international patent application publication WO 2004/057307 A1, international patent application publication WO 2004/057308 A1, international patent application publication WO 2004/058950 A1, international patent application publication WO 2004/059287 A2, international patent application publication WO 2004/058404 A2, international patent application publication WO 2004/059284 A2, international patent application publication WO 2004/059288 A2, international patent application publication WO 2004/059441 A2, and international patent application publication WO 2004/059297 A1.

FIELD OF THE INVENTION

This disclosure relates to preparation of biological samples and in particular, to systems and methods for the automated, continuous flow, pre-treatment and processing of biological samples.

BACKGROUND

In this disclosure, the term "staining" is used to refer to the process by which certain parts of a sample are treated in order to reveal or highlight characteristics of the sample. As a result of staining, characteristics sought to be revealed may acquire a different color, either in the optic range or in another electromagnetic range, such as the ultra-violet range. In some instances, staining may lead to a detectable change in properties, such as a change in the fluorescent, magnetic, electrical, or radioactive properties of the sample. To obtain a staining a sample may undergo a series of treatment steps referred to as a treatment protocol. A typical treatment protocol may include any or all of washing; binding of reagents to the specific parts of the sample; any activation of the reagents; and each treatment step may include a plurality of individual treatments.

Sample processing in immunohistochemical ("IHC") applications, for example, and in other chemical and biological analyses may involve one or a number of various processing sequences or treatment protocols as part of an analysis of one or more samples. Typically, such treatment protocols are defined by organizations or individuals requesting analysis, such as pathologists or histologists attached to a hospital, and may be further defined by the dictates of a particular analysis to be performed.

In preparation for sample analysis, a biological sample may be acquired and presented on a slide or other carrier usually in some form of preservation. As one example, a sample such as a layer or slice of skin may be preserved in formaldehyde and presented on a slide with one or more paraffin or other chemical layers overlaying the sample. Samples preserved with paraffin may undergo deparaffinization, a process by which paraffin layers overlaying the sample are removed. In addition, the target or sample may be restored to a condition where it is suitable for staining operations—a process known as target retrieval.

Immunologic applications, for example, may involve processing sequences or treatment protocols that comprise steps such as deparaffinization, target retrieval, and staining, especially for in-situ hybridization ("ISH") techniques. Previously, these steps have generally been performed manually, potentially creating a time-intensive treatment protocol and necessitating personnel to be actively involved in the sample processing. Attempts have been made to automate sample processing to address the need for a less manually burdensome and expedient sample processing operation. However, prior sample processing automation efforts have been extremely limited in scope and have been deficient in several aspects, such as, for example, the following: the lack of sufficient control and monitoring of sample processing; the lack of information sharing regarding processing treatment protocols and process status, especially for individual samples; the lack of diagnostic capabilities; and the lack of real-time or adaptive capabilities for continuous multiple sample processing.

Conventional apparatuses have also not provided for sample pre-treatment. Biological samples, such as tissue samples, are usually prepared before the staining can be performed and may be subjected to a pre-treatment process depending upon the type of staining process that is to be performed on the tissue. Pre-treatment processes are generally carried out manually in a laboratory and may include deparaffinization or target retrieval. In addition, pre-treatment processes may also require immersion of the slide in a buffer, or in other types of processing liquids, for some predetermined amount of time and at a specific temperature. Manual sample preparation is cumbersome because pre-treatment steps are often subject to stringent constraints and are sensitive to minute variations in experimental conditions. Consequently, small deviations in the pre-treatment protocol may lead to improper pre-treatment and inaccurate results.

Thus, there is a need for systems and methods to allow for the intelligent automatic real-time continuous processing of biological samples, so that once a carrier containing a sample, such as a slide, has been prepared and introduced into an apparatus, it is processed in accordance with specified treatment protocols, in conformity with any constraints, and, with minimal, or no further user-intervention.

There is also a need for systems that automate the scheduling of sample processing to maximize throughput and that allow users to track and monitor the status of slides in the apparatus. Additionally, because of the sensitive nature of the process, there is a need to provide feedback to users about processing related errors, or a lack of resources in sufficient time for corrective action to be taken. Moreover, there is a need to collect both slide and apparatus related information and share the collected information so as to improve efficiency and allow automatic interaction with other information processing systems.

SUMMARY

In some embodiments of systems, methods and apparatus according to the present invention the automatic pre-treatment of the biological samples on slides or other similar carriers or substrates in an automatic staining apparatus is performed, so that the entire processing of the biological samples may be performed automatically in a single physical apparatus.

Some embodiments of the present invention also include a method comprising steps for adaptively scheduling robot tasks in a time interval, for a robot coupled to a stainer. In some embodiments, the robot treats slides that are coupled to the stainer according to a treatment protocol using reagents in reagent bottles or fluid containers coupled to the stainer. In some embodiments, the steps in a method to adaptively schedule robot tasks in a time interval comprise creating a robot task list comprising all robot tasks that are ready for execution within the time interval, calculating a robot task priority for each robot task in the robot task list, sorting the robot task list in descending order of robot task priority, and adding robot tasks starting from the top of the sorted robot task list to a robot task execution queue until the robot is fully utilized in the time interval, or the robot task list is exhausted.

In some embodiments, the robot tasks ready for execution comprise those robot tasks where no prerequisites for commencing robot task execution remain to be completed. In some embodiments, creating a robot task list comprising all robot tasks that are ready for execution within the time interval further comprises determining slides that may spoil if a new treatment protocol step is not performed within the time interval, determining if robot tasks associated with the new treatment protocol step for each slide may be performed within the time interval, and substituting a task of applying buffer to a slide for each slide for which robot tasks associated with the new treatment protocol step cannot be performed within the time interval.

In some embodiments, creating the robot task list further comprises adding robot tasks that have been generated as a result of contemporaneous events to the robot task list. The contemporaneous events comprise one or more of introducing new slides into the stainer, adding or removing reagent bottles or fluid containers, and altering a priority assigned to one or more slide racks on which the slides are mounted. In some embodiments, the robot may performs tasks of many types comprising one or more of moving the robot to a position within the stainer, mixing reagents for a slide, applying a reagent to a slide from the reagent bottle or the fluid container, air blowing a slide, tipping a slide to a horizontal or a vertical position; and capturing an image of a slide. In some embodiments, applying a reagent to a slide from the reagent bottle or the fluid container further comprises one or more of applying a buffer to a slide; and applying deionized water to a slide.

In some embodiments, the steps in a method for adaptively scheduling robot tasks in a time interval are performed autonomously by the stainer, which may exercise control over the robot and its operations. In some embodiments, the steps are repeatedly executed for successive time intervals starting from the time at which the stainer is first powered on. In some embodiments, the steps are executed concurrent with the performance of other stainer and robot tasks.

In some embodiments, calculating a robot task priority for each robot task in the robot task list further comprises calculating a score for each robot task based on a mathematical function of sub-scores assigned to individual task parameters. In some embodiments, the individual task parameters further comprise the earliest start time for a task, the latest start time for a task, the time duration to execute the task, the location of the robot, the priority of the rack on which a slide associated with the task is mounted, and a predetermined relative priority for the robot task type. In some embodiments, a predetermined relative priority for a robot task may be one of high or low. In some embodiments, certain robot tasks may be designated highest priority and added directly to the top of the robot's execution queue.

The foregoing summary does not purport to define the invention. Indeed, it should be understood that the foregoing and following descriptions are exemplary. These and other embodiments of the invention are more fully described below with respect to the following figures.

BRIEF DESCRIPTION OF THE DRAWINGS

The accompanying drawings, which are incorporated in and constitute a part of this specification, illustrate a number of non-limiting embodiments of the invention and, together with the description, serve to explain the principles of the invention. In the figures, elements with similar functions are prefixed with the same numeric identifier, and individual instances are identified with a hyphenated ordinal suffix.

DETAILED DESCRIPTION

Figure 1A:
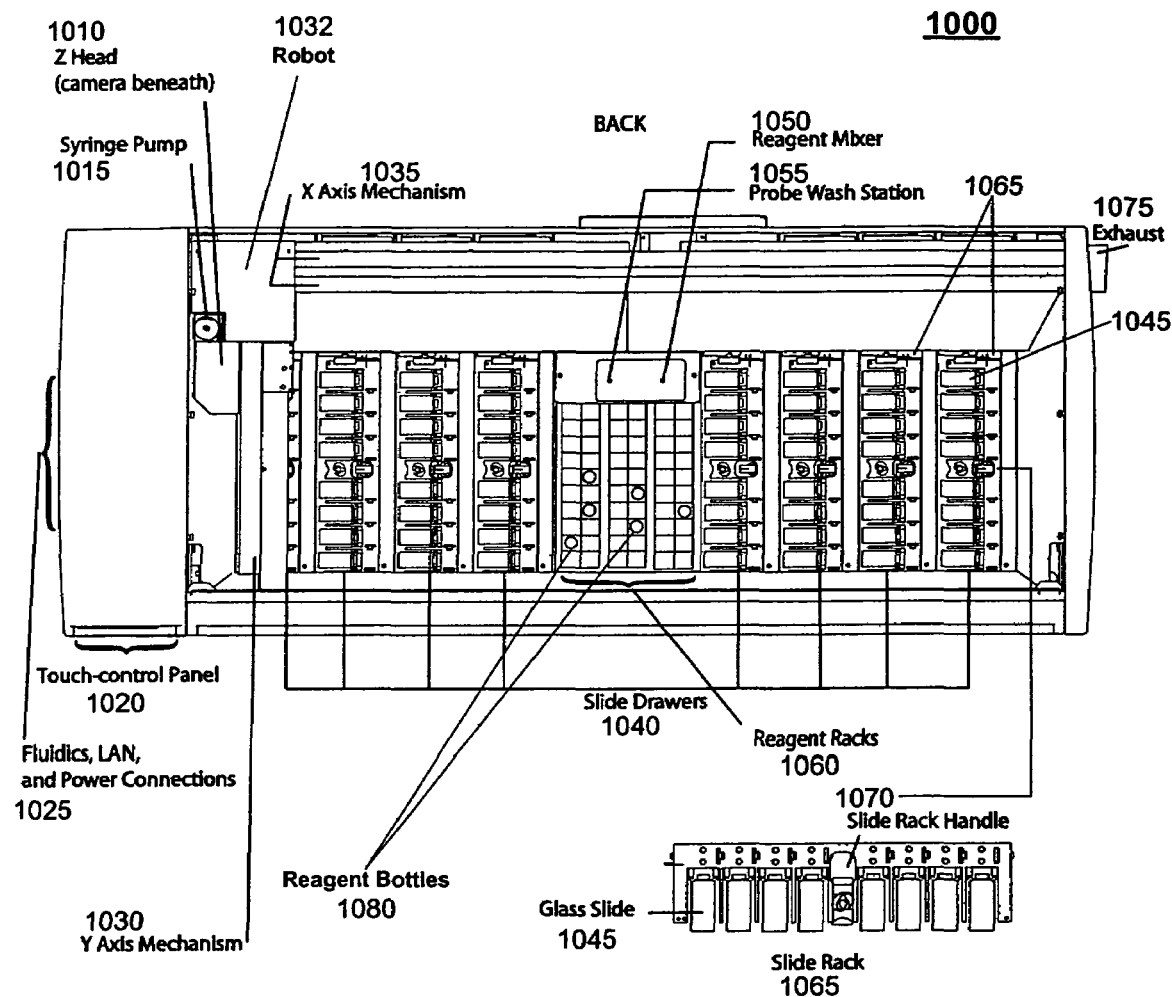
FIG. 1A shows the top-view of an apparatus for the automatic pre-treatment and processing of biological samples.

Some embodiments of the present invention include a system and method for pre-treatment of biological samples. Various modifications to the embodiments described will be readily apparent to those skilled in the art and generic principles disclosed herein may be applied to other embodiments. The described examples are exemplary only and embodiments described herein are not intended to limit the present invention. As such, the inventions are to be accorded the widest scope consistent with the principles and features described herein.

The present disclosure relates, in part, to the field of software and hardware for the control, management, tracking, monitoring, scheduling, and diagnosing of automatic biological sample processing systems. In some embodiments, systems, methods, and apparatus according to the present invention allow for the automatic pre-treatment of the biological samples on slides or other carriers or substrates (hereinafter referred to generally as slides) in an automatic staining apparatus (hereinafter referred to as a stainer) so that the entire processing of the biological samples may be performed automatically in a single physical apparatus.

In some embodiments, a method for processing slides comprises introducing one or more new slides into a stainer, obtaining slide identification information for at least one of the one or more new slides, obtaining a treatment protocol sequence for the at least one of the one or more new slides from a database associated with the stainer using the slide identification information, and processing the new slide according to commands in a command list corresponding to the treatment protocol sequence for the at least one new slide of the one or more new slides. In some embodiments, one or more new slides are introduced into the stainer while the stainer is processing of any old slides previously presented to the stainer.

In some embodiments, a treatment protocol sequence for the at least one new slide may be obtained from the database associated with the stainer by retrieving an individual slide record containing the treatment protocol sequence for the at least one new slide using the slide identification information on the at least one new slide.

In some embodiments, processing the at least one new slide according to commands in a command list corresponding to the treatment protocol sequence for the at least one new slide further comprises creating a list of stainer commands corresponding to individual processing steps in the treatment protocol sequence for the at least one new slide and executing commands in the command list in order on the stainer on the at least one new slide. In some embodiments, processing the new slide according to commands in a command list corresponding to the treatment protocol sequence for the at least one new slide of the one or more new slides is performed autonomously by the stainer.

In some embodiments, slide identification information for the at least one new slide may be obtained by reading a label containing the encoded slide identification information affixed to the at least one new slide. In some embodiments, slide identification may be obtained by reading a glyph that contains the encoded slide identification information. In some embodiments, slide identification information for the at least one new slide may be obtained by reading a radio frequency identification tag associated with the at least one new slide.

In some embodiments, the database associated with the stainer may be accessed for other purposes including slide pre-processing, data entry, queries, and report generation concurrent with the processing of any old slides previously presented to the stainer. Slide pre-processing includes creating or updating slide records pertaining to slides in the database associated with the stainer and generating labels containing slide identification information for affixment to slides.

In some embodiments, executing commands in the command list in order on the stainer on the at least one new slide further comprises determining if prerequisites for execution of a next command on the command list have been satisfied, taking corrective action if prerequisites for execution of the next command in order on the command list have not been satisfied, and executing the next command when prerequisites for execution of that command have been satisfied. In some embodiments, executing the next command when prerequisites for execution of that command have been satisfied further comprises applying a reagent to the at least one new slide and updating at least one database record in the database associated with the stainer to reflect the completion of execution. In some embodiments, determining if the prerequisites for execution of the next command on the command list have been satisfied further comprises obtaining information on reagents to be used in executing the next command and determining if an adequate quantity of the reagent is available.

In some embodiments, taking corrective action if prerequisites for execution of the next command in order on the command list have not been satisfied further comprises alerting an operator about prerequisites for the next command that have not been satisfied and monitoring unsatisfied prerequisites for the next command for changes in status.

In some embodiments, updating at least one database record in the database associated with the stainer to reflect the completion of execution further comprises updating at least one database record elected from a group consisting of a slide log to reflect the actions taken on the at least one new slide, a reagent log to reflect the actions taken on a reagent, and a stainer log to reflect the actions taken by the stainer.

Some embodiments of the invention also include a method for performing operations over a network on at least one stainer of a plurality of stainers connected in a LAN, comprising establishing a network connection with the at least one stainer in the LAN, sending commands to the at least one stainer over the network connection, and receiving responses corresponding to commands sent to the at least one stainer over the network connection. In some embodiments, establishing a network connection with the at least one stainer is initiated from a device within the LAN.

In some embodiments, establishing a network connection with the at least one stainer in the LAN further comprises establishing a network connection with an agent within the LAN, wherein the functions of the agent comprise relaying commands to, and responses from the at least one stainer, and relaying queries to, and returning responses from, a database associated with the plurality of stainers, wherein the database includes information including status information about stainers, slides, consumables, and treatment protocols associated with the plurality of stainers. In some embodiments, the agent is a software tool that also provides a defined interface for an external application through which operations may be performed on the at least one stainer over the network. In some embodiments, the external application is a laboratory information system.

In some embodiments, the operations performed over the network on the at least one stainer include running diagnostic tests and retrieving diagnostic information. In some embodiments, the diagnostic information is used to automatically schedule service on the at least one stainer, if the diagnostic information indicates that such service is to be performed. In some embodiments, the operations performed over the network on the at least one stainer include performing one or more of software and firmware updates.

In some embodiments, the operations performed over the network on the at least one stainer include obtaining information on stainer consumable usage. In some embodiments, information on stainer consumable usage could include aggregate stainer consumable usage for the plurality of stainers. In some embodiments, the information on stainer consumable usage includes reagent usage information and bulk fluid usage information. In some embodiments, the information on stainer consumable usage is used to make a determination regarding the ordering of additional supplies of one or more consumables. In some embodiments, the ordering of additional supplies of one or more consumables is done automatically. In some embodiments, the ordering of additional supplies of one or more consumables is based on an economic order quantity. In some embodiments, the ordering of additional supplies of one or more consumables is based on a predefined plan for the ordering of consumables subscribed to by an entity operating the stainer network.

In some embodiments, the operations performed over the network on the at least one stainer include monitoring the status of slides being processed by the at least one stainer apparatus. In some embodiments, the operations performed over the network on the at least one stainer include obtaining a real-time estimate of the completion time of any of the slides being processed by the at least one stainer. In some embodiments, a real-time estimate of the completion time may reflect the effect of user actions or other unscheduled events such as the introduction or removal of reagent bottles from the stainer, or changing a priority of a slide rack in the stainer, or introducing new slides into the stainer.

In some embodiments, the operations performed over the network on the at least one stainer include obtaining images of samples on slides being processed by the at least one stainer. In some embodiments, the images of the sample may be taken with an appropriate magnification and resolution. In some embodiments, the operations performed over the network on the at least one stainer include obtaining status information pertaining to slides that have not been loaded into the stainer. In some embodiments, all information exchanged with the stainer over the network connection, including all commands sent to the stainer over the network connection and all responses received over the network connection, are encrypted.

Some embodiments of the present invention also include a method comprising steps for adaptively scheduling robot tasks in a time interval for a robot coupled to a stainer. In some embodiments, the robot treats slides that are coupled to the stainer according to a treatment protocol using reagents in reagent bottles or fluid containers coupled to the stainer. In some embodiments, the steps in a method to adaptively schedule robot tasks in a time interval comprise creating a robot task list comprising all robot tasks that are ready for execution within the time interval, calculating a robot task priority for each robot task in the robot task list, sorting the robot task list in descending order of robot task priority, and adding robot tasks starting from the top of the sorted robot task list to a robot task execution queue until the robot is fully utilized in the time interval, or the robot task list is exhausted.

In some embodiments, the robot tasks ready for execution comprise those robot tasks where no prerequisites for commencing robot task execution remain to be completed. In some embodiments, creating a robot task list comprising all robot tasks that are ready for execution within the time interval further comprises determining slides that may spoil, if a new treatment protocol step is not performed within the time interval, determining if robot tasks associated with the new treatment protocol step for each slide may be performed within the time interval, and substituting a task of applying buffer to a slide for each slide for which robot tasks associated with the new treatment protocol step cannot be performed within the time interval.

In some embodiments, creating the robot task list further comprises adding robot tasks that have been generated as a result of contemporaneous events to the robot task list. The contemporaneous events comprise one or more of introducing new slides into the stainer, adding or removing reagent bottles or fluid containers, and altering a priority assigned to one or more slide racks on which the slides are mounted. In some embodiments, the robot may performs tasks of many types comprising one or more of moving the robot to a position within the stainer, mixing reagents for a slide, applying a reagent to a slide from the reagent bottle or the fluid container, air blowing a slide, tipping a slide to a horizontal or a vertical position; and capturing an image of a slide. In some embodiments, applying a reagent to a slide from the reagent bottle or the fluid container further comprises one or more of applying a buffer to a slide, and applying deionized water to a slide.

In some embodiments, the steps in a method for adaptively scheduling robot tasks in a time interval are performed autonomously by the stainer, which may exercise control over the robot and its operations. In some embodiments, the steps are repeatedly executed for successive time intervals starting from the time at which the stainer is first powered on. In some embodiments, the steps are executed concurrent with the performance of other stainer and robot tasks.

In some embodiments, calculating a robot task priority for each robot task in the robot task list further comprises calculating a score for each robot task based on a mathematical function of sub-scores assigned to individual task parameters. In some embodiments, the individual task parameters further comprise the earliest start time for a task, the latest start time for a task, the time duration to execute the task, the location of the robot, the priority of the rack on which a slide associated with the task is mounted, and a predetermined relative priority for the robot task type. In some embodiments, a predetermined relative priority for a robot task may be one of high or low. In some embodiments, certain robot tasks may be designated highest priority and added directly to the top of the robot's execution queue.

Some embodiments of the invention also include a method for dynamically allocating at least one of a plurality of resources coupled to a stainer in response to a resource allocation request by a task comprising determining a requested fraction of the at least one of a plurality of resources, computing a utilization factor of the at least one of a plurality of resources at several potential allocation time instants, adding the requested fraction of the at least one of a plurality of resources to the utilization factor at each potential allocation time instant to obtain a projected utilization factor, and allocating the at least one of a plurality of resources at the first time instant at which the projected utilization factor for the at least one of a plurality of resources is one or less.

In some embodiments, computing a utilization factor of the at least one resource at several potential allocation time instants further comprises determining resource utilization factors for the at least one resource by all tasks executing or scheduled to be executing at the several potential allocation time instants. In some embodiments, the plurality of resources coupled to a stainer comprise one or more of fluid conduits coupled to the stainer, one or more valves coupled to the stainer controlling access to the fluid conduits, one or more reagent mixers coupled to the stainer, and power available to processing tank heaters coupled to the stainer.

In some embodiments, the stainer may generate additional resource allocation requests corresponding to actions to be taken prior to allocating the at least one resource to a task. In some embodiments, the actions to be taken prior to allocating the at least one resource to a task may include flushing a fluid conduit or a reagent mixer coupled to the stainer.

Some embodiments of the invention provide a GUI to allow user input and control of the apparatus. Some embodiments of the present invention include a system for the software simulation of the operation of the sample processing system apparatus. Such a system allows testing, debugging, and performance tuning of the sample processing system apparatus, hardware, and software.

In some embodiments, one or more optical and/or electronic sensors may be used to retrieve slide-related information, including high resolution images of samples on the slides. In some embodiments, these images may be indexed, stored, and retrieved for processing and analysis. In some embodiments, images of the samples may be captured, indexed, and stored at various stages of the processing.

A detailed description of embodiments of the present invention follows, with reference to the accompanying drawings. In the figures, elements with the same numeric identifier have similar function, and individual instances are identified with a hyphenated ordinal suffix.

FIG. 1A shows the top-view of an exemplary stainer 1000 for the automatic pre-treatment and processing of biological samples. As shown in FIG. 1A, exemplary stainer 1000 includes slide drawers 1040 that contain slides 1045, which may contain biological samples needing treatment. In some embodiments, slides 1045 are mounted on individual holders hinged to slide rack handle 1070, which allow individual slides 1045 to be maneuvered to a horizontal or vertical position. In some embodiments, the slide rack handle 1070 may allow the slides 1045 to be tipped vertically or horizontally. In some embodiments, the slide rack 1065 may be placed in one of a plurality of slide drawers 1040, which is slid into stainer 1000. In some embodiments, processing tanks (not shown) may be present beneath the slides 1045. In some embodiments, the processing tanks may be temperature controlled. Processing tanks may be filled with fluid, drained, and/or flushed using fluids supplied by the fluidics component of fluidics, LAN, and power connections 1025. In some embodiments, slides 1045 may be immersed in the fluid present in a processing tank in accordance with some methods for the pretreatment of biological samples. In some embodiments, stainer 1000 also contains robot 1032.

Figure 1B:
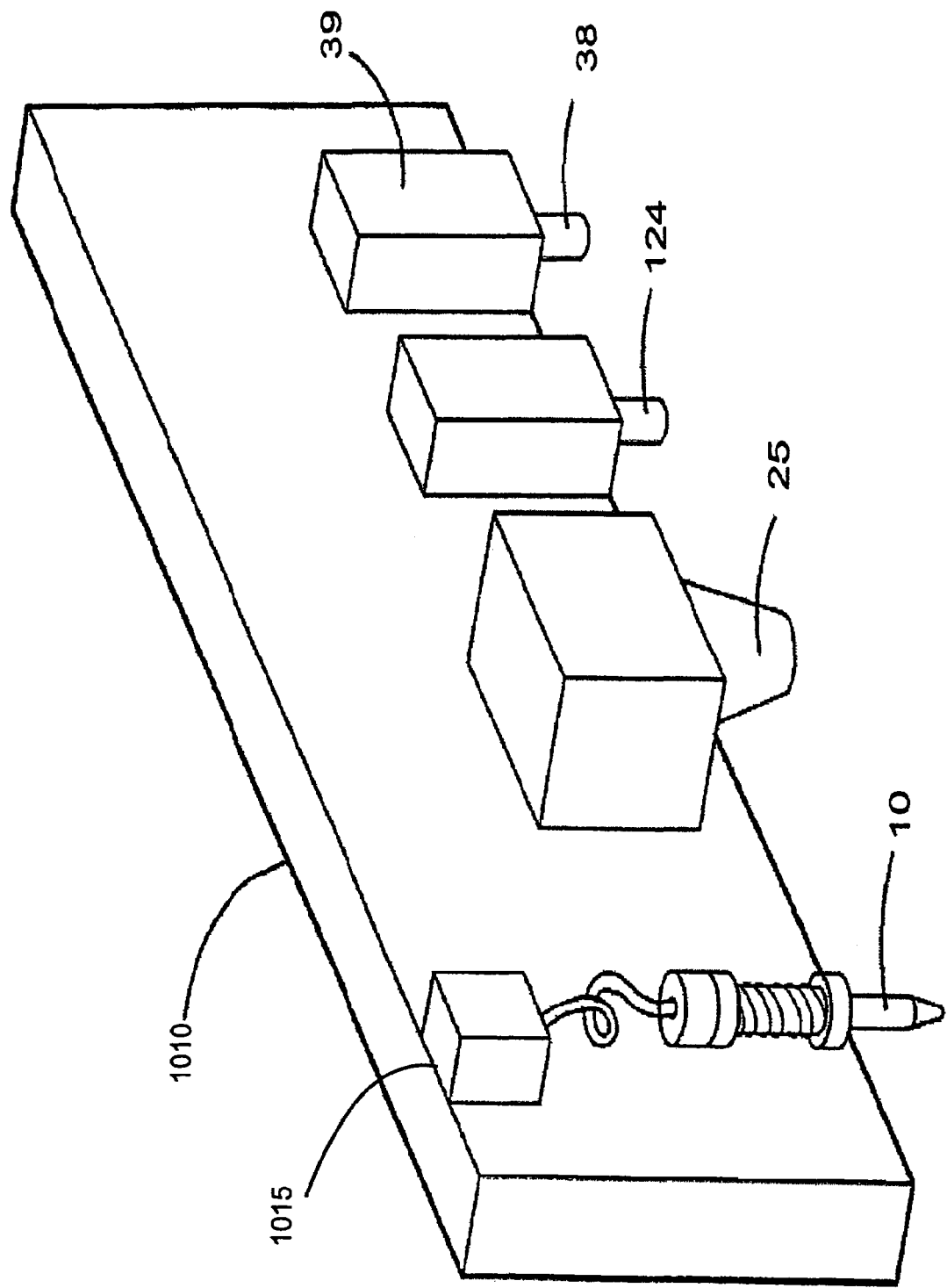
FIG. 1B shows a schematic of an exemplary robot head used in an apparatus for the automatic pre-treatment and processing of biological samples.

As shown in FIG. 1B, exemplary robot head 1010 may include one or more of a probe 10, optical or electronic sensing device 25, syringe pump 1015, air nozzle 124, air cylinder 39 and slide tipping tool 38. In some embodiments, probe 10 may be used to aspirate a precise quantity of reagent from reagent bottle 1080 for application to slide 1045. (FIGS. 1A and 1B). In some embodiments, robot 1032 may be directed to reagent mixer 1050 so that reagents aspirated from reagent bottle 1080 by probe 10 may be mixed in reagent mixer 1050 to create new or custom reagents. In some embodiments, robot 1032 may be directed to probe wash station 1055 to permit probe 10 to be washed. Washing probe 10 prevents reagent contamination and residue build-up in probe 10. In some embodiments, the aspiration and release of reagents may be controlled by syringe pump 1015.

As schematically illustrated in FIG. 1B, the robotic head 1032 may also be provided with an air nozzle 124 for blowing air onto slide 1045 in order dry slide 1045, or to blow away liquid. Robot head 1010 may also include a variety of other components, including, but not limited to a slide tipping tool 38, for actuating slide rotation, that may be coupled to an air cylinder 39. In some embodiments, slide tipping tool 38 may operate on slide 1045 to tip the slides from a vertical to a horizontal position and vice versa.

In some embodiments, robot head 1010 may include an optical or electronic sensor 25, which may be moved to various positions within stainer 1000 through action of the robot 1032. In some embodiments, optical or electronic sensor 25 can include a camera, which may be a Charge Coupled Device ("CCD") camera. In some embodiments, the camera may be a high resolution camera capable of taking pictures of the samples on the slides at an appropriate magnification. In some embodiments, the captured image may be analyzed for reagent analysis or other analyses. In some embodiments, the camera may be used 1) as an area locator, 2) to locate a tissue area, or 3) to apply reagent based on location and area. In some embodiments, data captured by electronic or optical sensor 25 may be associated with the location of robot 1032, and/or with the location of electronic or optical sensor 25, and/or with the location of slide 1045 or reagent bottle 1080.

In some embodiments, when a slide 1045 is in a horizontal position, a precise quantity of reagent may be applied to slide 1045 using a probe 10 and syringe pump 1015 mounted on robot 1032. In some embodiments, a separate conduit may be used to apply a buffer to slide 1045 in a horizontal position. Robot 1032 is capable of moving in two-dimensions using X axis mechanism 1035 and Y axis mechanism 1030. The movement and positions of robot 1032 may be tracked. Additionally, in some embodiments a docking or homing station with a known reference position may be provided for robot 1032. Robot 1032 may dock or be commanded to dock at the homing station when it is idle, prior to tracking its movements, for calibration purposes, and/or to prevent, correct, and minimize tracking errors. Robot 1032 also contains a Z head 1010 that is capable of being moved in the Z (vertical) dimension (perpendicular to the page). In some embodiments, the movement of robot 1032 and timing of reagent application may be controlled by a scheduler (not shown in FIG. 1A) that coordinates the movement of robot 1032 and reagent and buffer application based on treatment protocol constraints.

In some embodiments, a plurality of reagent racks 1060 hold individual labeled reagent bottles 1080, which may be both humanly and electronically readable to identify the contents of reagent bottles 1080. In some embodiments, the identifiers may take the form of an Infoglyph™ and may be read using a camera or other sensing apparatus 25 mounted beneath Z head 1010. In some embodiments, slides 1045 may also be labeled with identifiers, including an Infoglyph™, which may contain information about the slide. Other systems for reading information, for example transponders, radio frequency identification ("RFID") receivers, magnetic readers, optical character recognition ("OCR") techniques etc. may also be utilized.

Reagents may be aspirated from reagent bottles 1080 using syringe pump 1015 and probe 10, then mixed with other reagents using reagent mixer 1050, if specified by the protocol, before being applied to the slides 1045. In some embodiments, the quantity of reagent applied to a slide 1045 may be controlled precisely by controls operating on syringe pump 1015. In some embodiments, syringe pump hardware 1015 may be motor driven, so that rotating the motor in a forward direction causes fluid to be aspirated into the syringe, and rotating the motor in a reverse direction drives the fluid back out of the syringe. In some embodiments, commands to syringe pump 1015 to aspirate and/or dispense reagent may be driven by a configuration table, which details the steps that syringe pump 1032 follows to perform the task at hand.

In some embodiments, sensors (not shown) may be present in or introduced into reagent bottles 1080 to detect the level of reagent remaining in reagent bottle 1080. In some embodiments, an operator may be alerted if a reagent level falls below a certain threshold. In some embodiments, reagent mixer 1050 may be capable of mixing a wide variety of reagents including mixing small and large volumes of reagents, mixing reagents with different viscosities and densities, and mixing nearly immiscible reagents. In some embodiments, gases formed during the mixing process are allowed to escape through exhaust 1075. Probe wash station 1055 allows probe 10 to be washed to remove any residues, to prevent residue build-up, and to prevent contamination of reagents and samples.

In some embodiments, stainer 1000 may also include fluidics, Local Area Network ("LAN") and power connections 1025, which includes controls and connections for fluidics, for networking and for power. As shown in FIG. 1E, some embodiments of stainer 1000 may include a fluidics sub-system with a fluidics cart 1295 with labeled electronically readable containers 1299 that store bulk fluids such as for example, slide buffers, fluids for flushing conduits, probe cleaning fluids, de-ionized water etc. In some embodiments, fluids may be delivered to locations, such as processing tanks, within stainer 1000 at appropriate points in time using conduits (not shown) from fluid containers 1299 on fluidics cart 1295. In some embodiments, multiple conduits may be provided for fluid delivery and the conduits allocated to fluids, based on resource allocation and scheduling algorithms in accordance with treatment protocol-related constraints. In some embodiments, fluids drained from stainer 1000 may be held in a separate labeled fluidics container 1299 in fluidics cart 1295 for bio-hazardous material.

Some embodiments of the invention may also provide LAN connections to allow stainer 1000 to communicate with other devices, including remote devices, other stainers, other laboratory instruments, laboratory and third party information systems, and computers within LAN 1223. LAN connections 1025 allow stainer 1000 to send and receive status information including information about slides 1045, process-status, treatment protocols, reagents, fluids, diagnostics, and other information that may be requested by remote users. In some embodiments, a touch-control panel 1020 may be provided to allow users to interact directly with stainer 1000. Touch control panel 1020 may provide a GUI along with menu screens and help screens to facilitate user-interaction and control of stainer 1000. Additionally, in some embodiments, stainer 1000 may also include an embedded computing system with processors, memory, hard drives, graphics and other electronic sub-systems (not shown) that allow software, firmware, and other program code to be run and executed on stainer 1000.

Figure 1C:
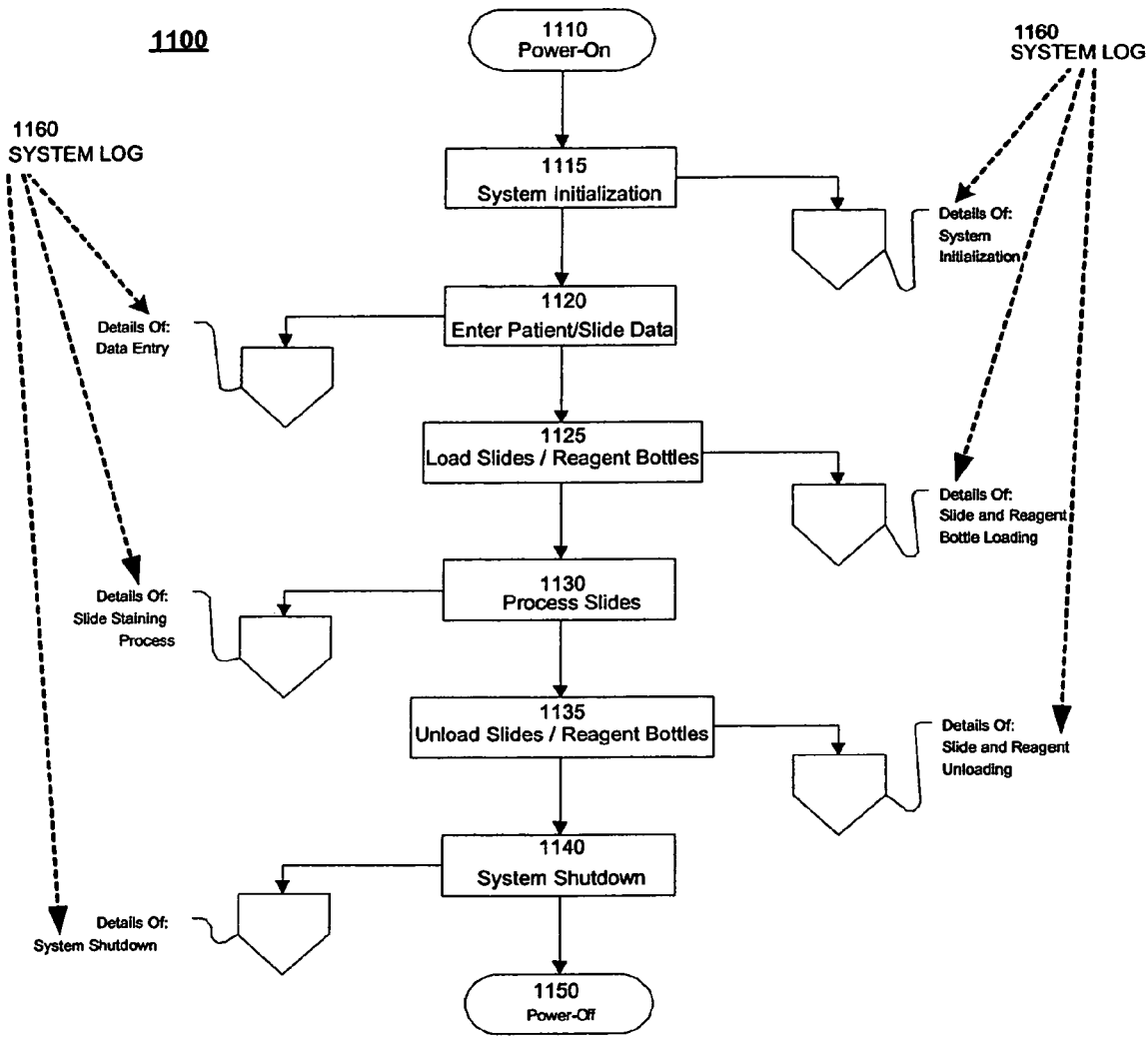
FIG. 1C illustrates an exemplary overall process flow for a slide undergoing automatic pre-treatment and processing in a stainer.

FIG. 1C illustrates an exemplary overall process flow 1100 for a single run of a system for the automatic pre-treatment of biological samples. It should be noted that steps 1120 through 1135 depicted in exemplary overall process flow 1100 occur in the sequence shown for a single slide. In general, steps 1120 through 1135 may be performed concurrently for different slides.

The system is turned on in step 1110, following which it goes through an initialization process in step 1115. In some embodiments, the initialization process may include booting up stainer 1000, running initial stainer diagnostics, establishing network and database connections, determining reagent and bulk fluid types and levels, moving robot 1032 to the homing station and other actions. In some embodiments, an operator may be alerted regarding possible diagnostic issues or other matters during the initialization phase.

After System Initialization has been completed, patient and/or slide data may be entered by an operator in step 1120. In some embodiments, the data may be retrieved electronically from another computer system, over a network, from a Laboratory Information System ("LIS"), or from another laboratory instrument. Patient data may include a patient identifier, sample related data, other identifying information and may include information regarding a medical provider or other services to which results data may be sent. Slide data may include a slide identifier and a treatment protocol associated with the slide. In some embodiments, slide data may be printed on a label in a machine readable format such as an Infoglyph™ and applied to a slide 1045 containing the sample.

In step 1125, slides 1045 and reagent bottles 1080 are loaded into stainer 1000. In some embodiments, a slide or reagent drawer is closed after slides 1045 have been loaded and slide and reagent labels may be read and any errors reported. For example, Infoglyph™ labels on the slides 1045 and reagent bottles 1080 may be read by a camera 25 mounted under Z-head 1010 (FIGS. 1A and 1B). In step 1130, the slides 1045 are processed according to the treatment protocol associated with the slide. Biological samples on a slide 1045 are often preserved using paraffin based agents. Samples on such slides 1045 may be subjected to a process of deparaffinization before a slide 1045 may be processed. Deparaffinization involves immersing slides 1045 into processing tanks where a series of fluids may be sequentially introduced and removed for predetermined periods of time (potentially for about 5 or 10 minutes). The process is intended to first remove from the tissue sample the paraffin in which it was mounted, then remove the paraffin solvent, then through a series of reagents progressively re-hydrate the sample. Deparaffinization and target retrieval processes are performed onboard stainer 1000 with the slides 1045 in a vertical orientation, immersed within their individual processing tanks that can be filled and emptied with various reagents. In some embodiments, the reagents may be heated to an appropriate temperature to permit effective treatment of the slides 1045.

In some embodiments, if deparaffinization or target retrieval is to be performed, the processing tanks beneath the slides 1045 are filled with the appropriate solution and the slides 1045 are lowered into the processing tank and immersed in the solution for an appropriate amount of time. Different fluids may then be introduced into processing tanks into which slides 1045 have been lowered according to the deparaffinization or target retrieval protocol. Slides 1045 may then be raised and the processing tanks drained. Deparaffinization is an initial slide processing step and generally performed only once, when slide pre-treatment is commenced. When the deparaffinization and target retrieval processes are complete the slides 1045 can be tipped back to a horizontal position and lowered down onto temperature controlled platforms to perform the staining phase.

A treatment protocol associated with a slide specifies the sequence of reagents, types of reagents, quantities, duration of exposure, temperature and other parameters related to the treatment of a slide. In some embodiments, the slide 1045 may be placed on a temperature controlled rack to ensure it is maintained at the correct temperature as specified in a treatment protocol. In some embodiments, software may check to ensure that all the reagents specified in a treatment protocol have been loaded prior to initialization of that protocol. An operator may be alerted if reagents specified for processing a slide 1045 are not present.

Once the processing of loaded slides 1045 has been completed, in step 1135, slides 1045 and reagent bottles 1080 may be unloaded. In some embodiments, reagent bottles 1080 may be swapped and/or new reagents added while slides 1045 are being processed. In some embodiments, new slides 1045 may be introduced for processing in a slide drawer 1040 that is currently unused, or reagent bottles 1080 introduced and/of removed, while slides 1045 in another slide drawer 1040 are being processed. Processing on such new slides 1045 introduced into stainer 1000 may begin even while processing on other slides previously presented to the stainer is in progress. In some embodiments, steps 1120 through 1135 may be repeated until all slides 1045 have been processed.

It should be noted that although steps 1120 to 1135 are performed sequentially with respect to a single slide, stainer 1000 may perform the steps concurrently on different slides. For example, an operator may be entering slide data, while a slide rack 1065 is being loaded and slides on another slide rack 1065 are undergoing processing.

In step 1140, the system may be shut down. In some embodiments, during shutdown processing tanks may be drained and hazardous waste purged into appropriate containers. Additionally, all processing tanks and fluid conduits may be cleaned and flushed, heating elements turned off, valves depressurized, and all drawers and doors closed. Finally, in step 1150, the system may be powered off.

In some embodiments, at steps 1115 through 1140 in exemplary overall process flow 1100, a System Log 1160 may be generated to keep track and maintain a log with details of events at each step, as shown in FIG. 1B. For example, details of system initialization such as the results of any system diagnostic tests may be stored in the log generated during step 1115. In some embodiments, the system log may be used to verify proper system functioning, pinpoint process errors, or used for quality assurance purposes. In some embodiments, the logs for each step depicted in FIG. 1B may also be stored separately or, associated with stainer objects such as slides 1045, or reagent bottles 1080. For example, actions performed on an individual slide 1045 may be recorded in individual slide logs, which describe every action undertaken on the slide 1045.

Figure 1D:
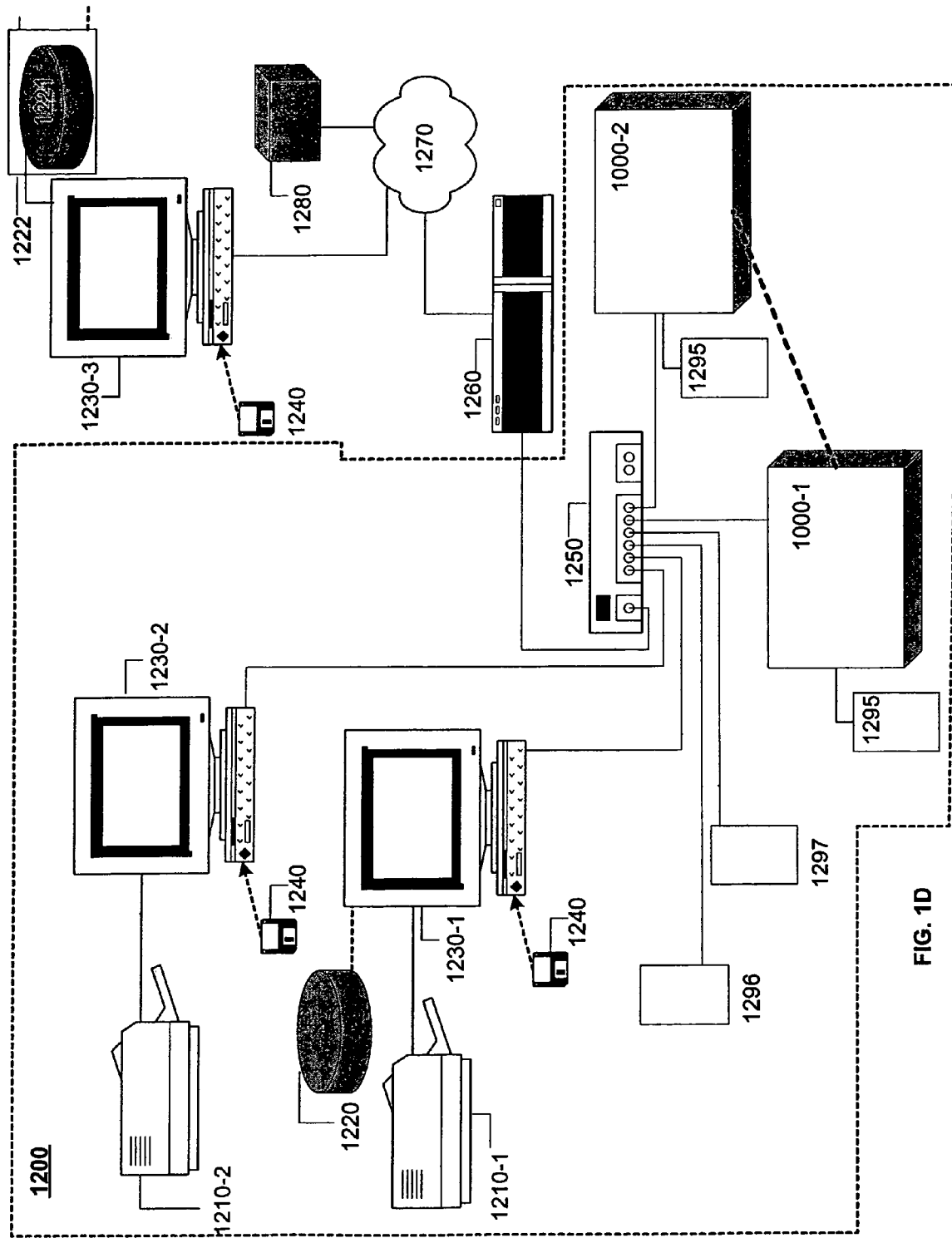
FIG. 1D illustrates an exemplary system for the automatic pre-treatment and processing of biological samples.
Figure 1E:
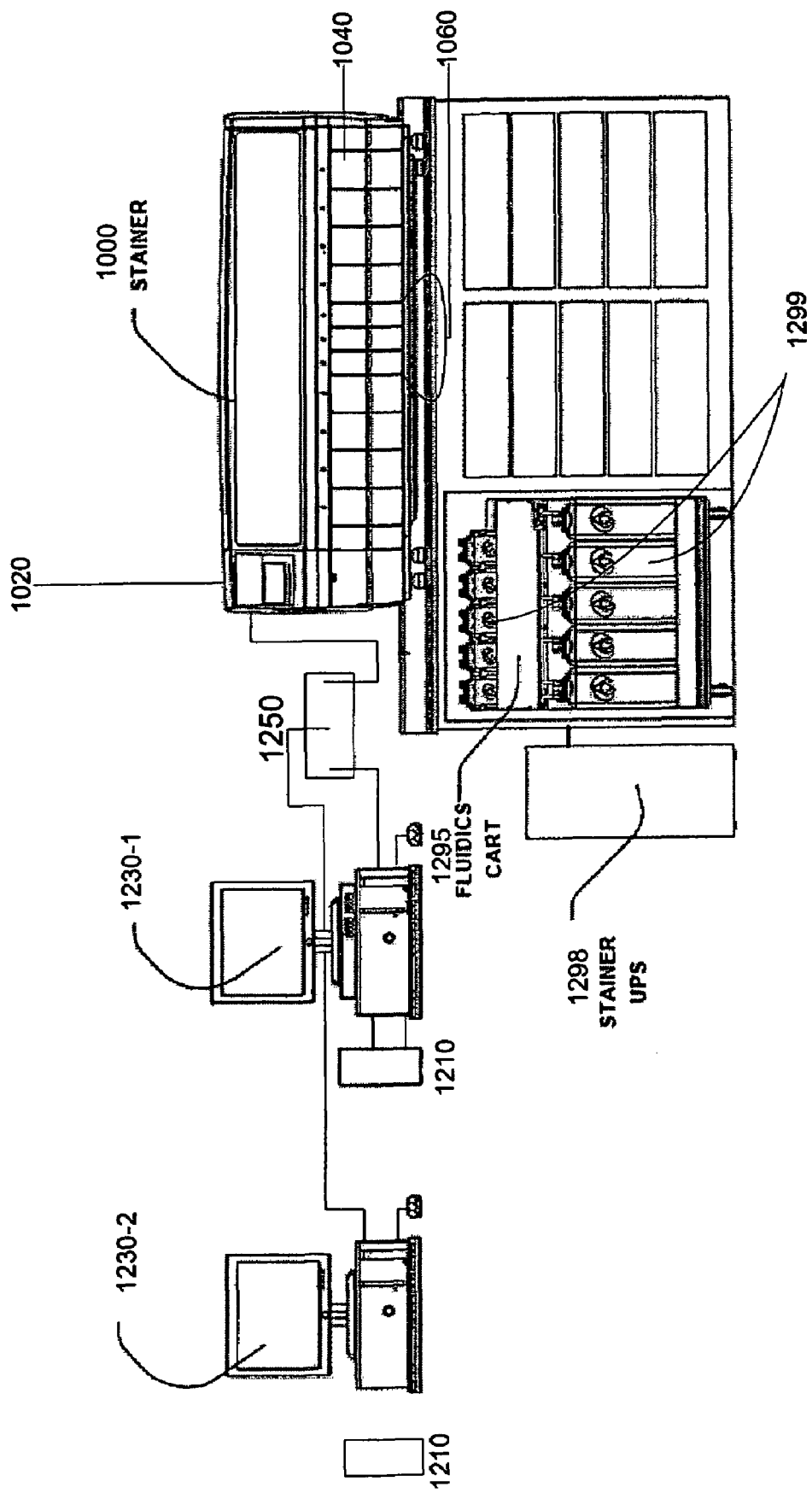
FIG. 1E shows an exemplary system for the automatic pre-treatment and processing of biological samples.

FIG. 1D illustrates an exemplary system 1200 for the automatic pre-treatment of biological samples. FIG. 1E also shows an exemplary system for automatic pretreatment of biological samples. A description of embodiments of a system for the automatic pretreatment of biological samples will now be made with reference to FIGS. 1D and 1E.

As shown in FIG. 1D, exemplary system 1200 can consist of one or more stainers 1000, such as exemplary stainer 1000-1 and 1000-2 with coupled bulk fluid carts 1295 containing bulk fluids used by the stainers. In some embodiments, additional stainers may be added to exemplary system 1200 as shown by the dashed line depicted in FIG. 1D between stainers 1000-1 and 1000-2. As shown in FIG. 1E, each stainer 1000 makes use of a number of bulk fluids to perform the pretreatment and staining tasks. In some embodiments, these fluids can be stored externally in containers 1299 in fluid cart 1295. In some embodiments, a fluid level sensor may be provided with each fluid container 1299 on a fluidics cart 1295 and read periodically by the coupled stainer 1000. In some embodiments, power may be supplied to each stainer 1000 through an Uninterruptible Power System (UPS) 1298, which may also be monitored by its coupled stainer 1000 to detect power-line fluctuations, or an impending loss of power.

In some embodiments, the stainers, such as exemplary stainers 1000-1 and 1000-2 may be networked in LAN 1223 and may communicate with other system components using network hub 1250. In some embodiments, stainers 1000 may contain embedded computing systems that allow software, firmware, and other program code to be stored, updated, compiled, and executed on the stainer. In some embodiments these programs may be able to interact and exchange data and control information with programs running on computing devices 1230-1 and 1230-2. In some embodiments, information may be exchanged between computing device 1230-1 and laboratory devices 1296 and 1297. In some embodiments, data may also be exchanged between laboratory devices 1296 and 1297 and database 1220.

Network hub 1250 may also provide a network connection to a Wide Area Network ("WAN") 1270 through network bridge 1260. In some embodiments, WAN 1270 can be the Internet. In some embodiments, the network connection to network hub 1250 may be wireless. In some embodiments, the wireless networking function may allow network hub 1250 to support the IEEE 802.11b and/or IEEE 802.11g and/or other wireless networking protocols, and serve as a Wireless Access Point (WAP). In some embodiments, communication between the stainers 1000 and/or with remote users 1280 through WAN 1270 may also occur using standard communications protocols such as TCP/IP, or any other communications protocol. In some embodiments, a remote user or remote device 1280 may query or communicate with any stainer 1000 through WAN 1270. In some embodiments, communication between stainers 1000 and/or communication over WAN 1270 may be encrypted.

In some embodiments of system 1200, stainers 1000 may also be coupled to one or more computing devices 1230 containing removable media drives capable of reading removable media 1240. Removable media 1240 may be a floppy disk, CD-ROM, DVD-ROM, DVD+RW, DVD-RW, or any other computer readable media. In some embodiments, computing devices 1230 may contain network and communication ports including, but not limited to, USB, Ethernet, Serial, and/or Parallel ports to allow communication with stainers 1000 and WAN 1270 through network hub 1250 and/or network bridge 1260 using appropriate communication devices, methodologies, and communication protocols. In some embodiments, computing device 1230 may also contain one or more of processors, memory, hard disks, graphics cards, and display and data entry devices. Examples of computing device 1230 include PCs, Workstations, Laptops, Handhelds, or any other mobile computing devices capable of being used in system 1200.

In some embodiments, computing device 1230-1 may be able to run software, such as a server, that coordinates the actions of the individual stainers 1000, obtains status of stainers 1000, and obtains and updates slide and process related information. Computing device 1230-1 may also be coupled to printer 1210-1 and database 1220. In some embodiments, database 1220 may contain system related information including stainer, patient, slide, treatment protocol, fluid and/or reagent related information. In some embodiments, computing device 1230-1 may query stainers 1000-1 and/or 1000-2 for status or other information and update database 1220. In some embodiments, a system log such as system log 1160 may be generated by stainers 1000-1 and 1000-2 and stored in database 1220. In some embodiments, printer 1210-1 coupled to computing device 1230-1 may also be used to print reports generated by computing device 1230-1. In some embodiments, stainer 1000 may back-up stainer, process and slide related information on storage media on computing device 1230-1.

In some embodiments, computing device 1230-2 may run software to allow users to enter data related to system 1200 into database 1220. In some embodiments, software running on computing device 1220-2 may allow users to configure and manage stainers 1000-1 and 1000-2. In some embodiments, users may enter data including identification data for slides 1045, reagent bottles 1080, and bulk fluid containers 1299 using software running on computing device 1230-2. In some embodiments, printer 1210-2 coupled to computing device 1220-2 may be used to print the slide, bulk fluid container, and/or reagent container labels.

In some embodiments, portions of programs or data related to the control and/or monitoring of stainers 1000 may reside on removable drive 1240. In some embodiments, programs running on computing device 1230-2 may provide stainer, slide, and process related information to users using an appropriate GUI. In some embodiments, users may be able to control the actions of one or more of stainers 1000 using programs running on computing device 1230-2.

In some embodiments, computing device 1230-3 may also run other laboratory information systems (LIS) 1222. LIS 1222 may use, store, and update data in database 1221 and also request information from stainer related applications running on computing device 1230-1 or from the stainers 1000 directly. In some embodiments, LIS 1222 running on computing device 1230-3 may store patient records and other lab related data. In some embodiments, a user may import patient data and slide orders into the System Manager from LIS 1222 through an intermediate interface called an "LIS Agent." In some embodiments, the LIS Agent may facilitate the exchange of data between the stainer 1000 and related software systems, software running on computing devices 1230-1 and 1230-2, and database 1220, on one hand and LIS 1222, on the other hand. In some embodiments, the LIS Agent may include software that provides a bidirectional interface to receive and send data to other software such as software running on stainers 1000, computing devices 1230, or laboratory devices 1296 or 1297. In some embodiments software running on computing device 1230-1 could include the LIS Agent as a module.

For example, information about reagent and/or bulk fluid usage could be analyzed by software running on computing device 1230-1 or 1230-2 and supplies ordered using LIS 1222 through the LIS Agent whenever the inventory level falls below a certain threshold. In some embodiments, re-ordering of supplies through LIS Agent may take place according to a prearranged subscription plan. In some embodiments, software running on computing device 1230-1 or 1230-2 may track diagnostic messages and/or error codes from stainers 1000 and automatically schedule service through the LIS Agent. In some embodiments, software running on computing device 1230-1 or 1230-2 may use stainer and slide related information to perform accounting functions, including the generation of invoices and reports. In some embodiments, software running on computing device 1230-1 or 1230-2 may use stainer and slide related information stored in database 1220 to generate cost and usage statistics relating to the operation of the stainers. In some embodiments, invoices and reports generated by software running on computing device 1230-1 or 1230-2 may be sent to LIS 1222 through the LIS agent. It should be noted that system 1200 is exemplary only and additional stainers, computers, lab devices, and other components may be added to the system in order to perform methods and achieve objects and functionality of the system.

Figure 1F:
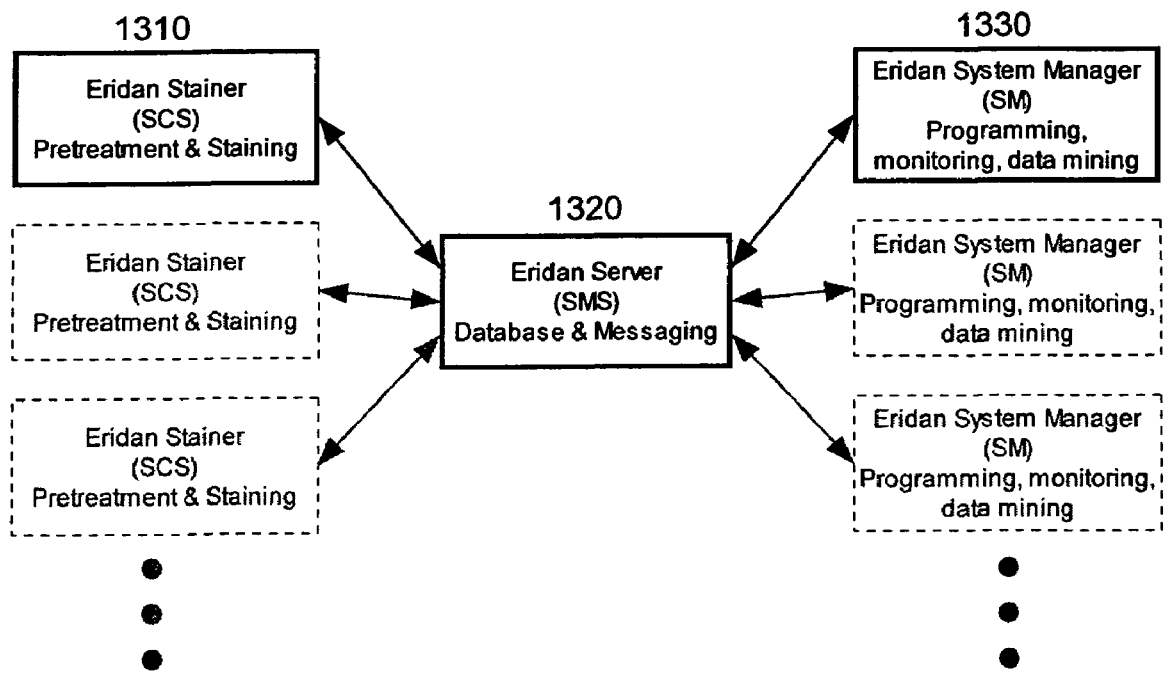
FIG. 1F illustrates exemplary software architecture for a system for automatic pre-treatment and processing of biological samples.

FIG. 1F illustrates exemplary software architecture for a system for automatic pre-treatment of biological samples. The architecture shown in FIG. 1F is exemplary and for descriptive purposes only and other configurations of the software may be used to achieve the same or similar functions. As shown in FIG. 1F, exemplary software architecture 1300 for a system for the automatic pre-treatment of biological samples may include Stainer Control Software ("SCS") 1310, System Manager Server ("SMS") 1320, and System Manager 1330 (SM). In some embodiments, multiple instances of SCS 1310, each running on individual stainers, may interact with multiple instances of SM 1330 through SMS 1320.

In some embodiments, SCS 1310 may be resident on and run directly stainer 1000 using its embedded computer system. In some embodiments, SMS 1320 may be resident and executed on exemplary computing device 1230-1 and maintain and update database 1220. In some embodiments, SM 1330 may be resident and executed on computing device 1230-2. In some embodiments, SMS 1320 and SM 1330 may be resident on different computing devices. At any point in time, multiple instances of SM 1330 may be active and interact with database 1220 through SMS 1320. SCS 1310 controls the staining instrument hardware on associated stainer 1000 so that the hardware may perform the operations of pre-treating and staining of slides 1045 that are introduced into the machine. In some embodiments, SCS 1310 software may communicate with SMS 1320 over TCP/IP on system LAN 1223 in order to obtain information about slides 1045 and reagents on stainers 1000.

In some embodiments slide programming of a slide 1045 may be done using SM 1330. Slide programming includes associating a treatment protocol with a slide 1045 and affixing an electronically readable label to the slide. Once a slide 1045 is electronically scanned and recognized by stainer 1000 its treatment protocol information is downloaded from SMS 1320 and, if the fluids for the treatment protocol are present, the stainer 1000 can automatically process the slide. In some embodiments, SCS 1310 controls the function of stainer 1000 and monitors level sensors associated with bulk fluid containers 1299 in bulk fluid cart 1295 to determine if enough fluid is available to complete certain tasks.

In some embodiments, SCS 1310 also supports a full simulation mode and can be run on a computer without any actual stainer hardware present. In this mode SCS 1310 simulates stainer hardware actions accurately and produces final results that are similar to results achieved using actual stainer hardware. In some embodiments, an accelerated simulation capability is also provided. The accelerated simulation capability, which uses time compression techniques, permits the debugging, validation, and performance tuning of stainer hardware and processes in a few minutes. The debugging, validation, or performance tuning processes would normally take several hours for each run on a conventional stainer. In some embodiments, SCS 1310 may run in simulation mode while executing on a stainer 1000 but without exercising any stainer hardware (other than the embedded computing system) or using any fluid or reagents. The simulation capability may also be used by the adaptive scheduler to determine optimal operation.

In some embodiments, SCS 1310 may perform some or all of the actions in steps 1115 and 1130, as related in the description of overall process flowchart 1100. When slide processing in a particular drawer is started, SCS 1310 locks the slide drawer 1040. In some embodiments, once staining has been completed the slide rack 1065 can be elevated to the load position and the slide rack 1065 can be marked complete. In some embodiments, the operator may be notified visually and aurally that the slide rack 1065 has completed and the slide drawer 1040 is unlocked to permit the operator to remove the rack.

In some embodiments, SCS 1310 uses a non-deterministic scheduling system to allow different staining processes to happen in parallel within different slide drawers 1040. The scheduling subsystem of SCS 1310 may continuously evaluate tasks to be performed, and makes decisions about the order of tasks based on priority. If errors occur during processing, for example if a reagent is not available an operator can be alerted. In some embodiments, SCS 1310 may direct the application of a buffer to the slide 1045 to prevent spoilage of the sample while an operator loads the reagent. SCS 1310 may also be run in a utility mode that allows technicians and operators to perform routine maintenance on the machine.

In some embodiments, SMS 1320 may serve as a data handling and processing center for the SM 1330 and SCS 1310. In some embodiments, SMS 1320 may communicate with SCS 1310 and SM 1330, handle database interaction, and perform support functions for each instance of SM 1330 and SCS 1310. In some embodiments, SMS 1320 may handle all SCS and SM data and messaging communications. In some embodiments, SMS 1320 can accept requests from SM 1330 and send out status reports in response. Additionally, SMS 1320 can also receive requests from SCS 1310 and send out status reports in response. In some embodiments, SMS 1320 may connect to and control a database system, such as database system 1220, in order to satisfy the incoming requests. To facilitate diagnostics, SMS 1320 may act as an agent, proxy, or intermediary for support connections to all instances of SCS 1310 and SM 1330 that are coupled to SMS 1320. In some embodiments, SMS 1320 may run on a computing device 1230-1, which in some instances may be a server.

In some embodiments, data and configuration parameters that affect the operation of the entire system may be maintained under the control of SMS 1320. In some embodiments, SMS 1320 may have an associated backup and restore utility that allows for automatic backups. In some embodiments, SMS 1320 may also automatically backup its database to hard disks on any or all of stainers 1000, when stainers 1000 are operating. Accordingly, in the event of catastrophic failure of SMS 1320, one of its components, or of its database, a ready backup can be made available thus limiting any down-time of the laboratory. In addition, stainer 1000 may use its copy of (backed up) database 1220 to complete the processing of slides already in stainer 1000 at the time of the failure. In some embodiments, SMS 1320 may automatically search LAN 1223 and auto-discover stainers 1000. In some embodiments, different TCP/IP ports may he used to segregate control, status, and diagnostic messages.

SM 1330 may also run on one of computing devices 1230. In some embodiments, SM 1330 may provide functionality for slide programming. For example, users may input one or more of patient demographic information, block information like tissue type and preparation, and treatment protocol related information into one or more records that may be stored in a database, such as exemplary database 1220. In some embodiments, SM 1330 may also provide an interface to add and edit other auxiliary information such as Tissue Types, Tissue Preparations, Reagent Compatibility, Users, and user-customizable fields.

In some embodiments, SM 1330 may also have a stainer-monitoring window showing a list of stainers 1000 and general status information, with options to allow a user to retrieve more detailed information about the status of stainers. For example, detailed slide status views may show slides pending, slides in a particular stainer, and slides that have completed the staining process and have been removed from machines. In some embodiments, SM 1330 may generate detailed reports related to slide processing, case history, and reagent usage in response to operator requests.

In some embodiments, SM 1330 may provide an interface to program and edit treatment protocols and detection systems. Treatment protocols define a complete sequence of steps to process a slide, whereas detection systems are templates that are complete except for the primary antibody and enzyme block. Additionally, SM 1330 may allow for the management of reagents, including reagent inventory, reagent usage, and reagent properties such as incompatibility, expiration date, and reagent category. Custom reagents, specified by users, can be added to the reagent list. In addition, embodiments of SM 1330 may allow the specification of "just-in-time" mixing of reagents, for reagents with a very short shelf life.

Figure 2A:
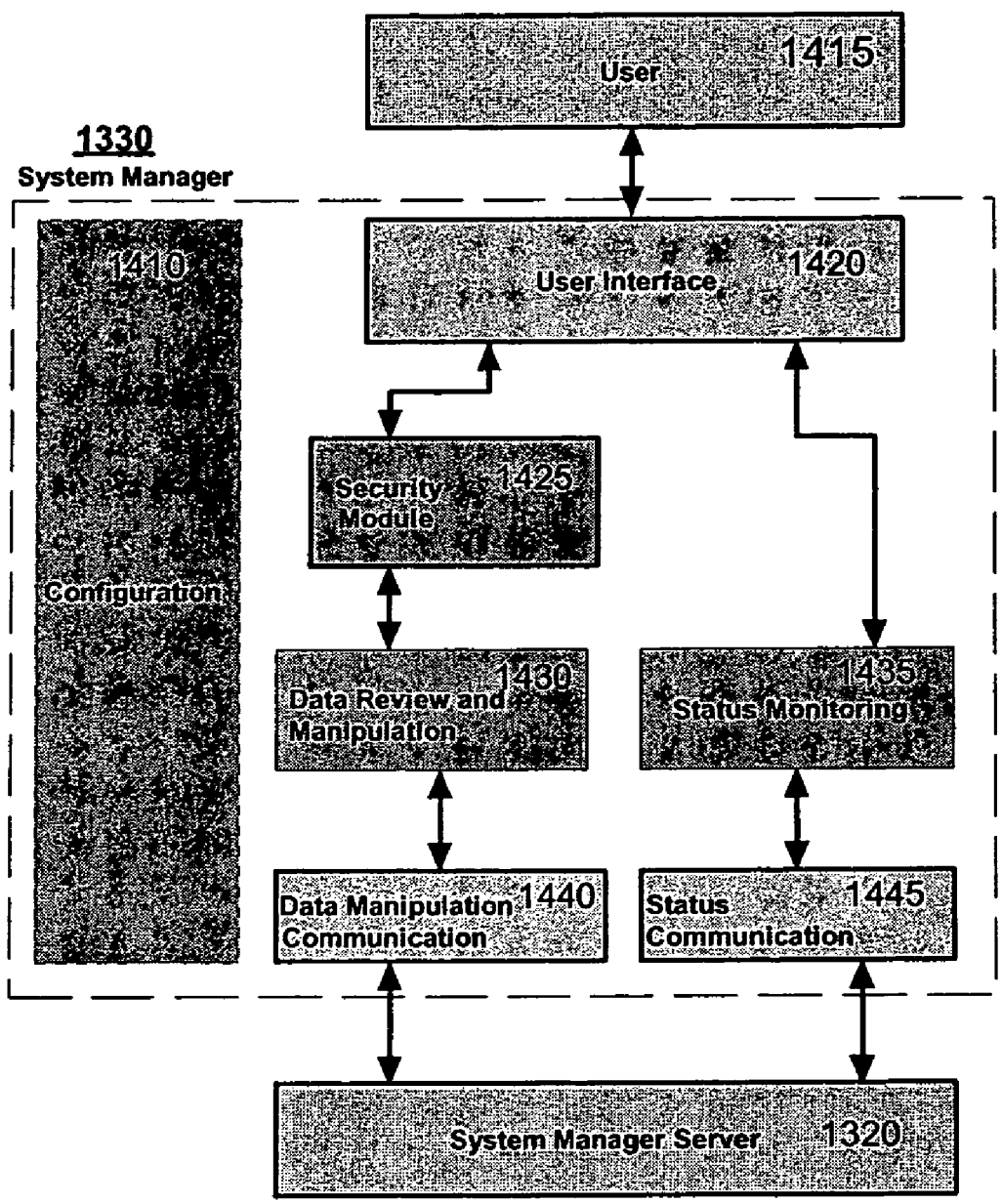
FIG. 2A illustrates exemplary software architecture for the System Manager.

FIG. 2A illustrates exemplary software architecture 1400 for the system manager 1330. Users 1415 may interact with SM 1330 through a user interface 1420, which may include menu screens and other features to help users to log in, request information, enter commands, change configuration parameters, update status information, and/or navigate through the system. In some embodiments, SM 1330 communicates with SMS 1320 using a status communication module 1445.

In some embodiments, status monitoring module 1435 allows users 1415 to request status information from stainers 1000 through user interface 1420, such as whether a stainer 1000 is active, operating normally, or has requested service or time-critical attention. Status communication module 1445 provides communication functionality to transmit such requests to stainers. Additionally, status communication module 1445 provides functionality to inform stainer 1000 through SCS 1310 about system configuration changes. In some embodiments, SMS 1320 may relay requests and responses between status communication module 1445 and SCS 1310. In some embodiments, SMS 1320 may perform additional processing on requests and responses prior to relaying the information to its destination. In some embodiments, the functionality of status monitoring module 1435 may be restricted to status communications of a general nature where information may be exchanged without regard to confidentiality, security, accessibility, and/or privacy issues.

In some embodiments, user 1415 may invoke a separate data review and manipulation module 1430 to request data from the stainers 1000 or SMS 1320 using user interface 1420 through security module 1425. For example, users may request a list of slides 1045 that have been programmed and labeled by the user, but have not appeared on any stainer 1000; a list of stainers 1000 that are being served by SMS 1320; a list of slides 1045 that are being processed by a stainer 1000; a list of slides 1045 that have completed the prescribed staining protocol and have been removed from stainer 1000; all information about a particular slide 1045 including case demographic information, slide ID, location, and estimated completion time; a list of all reagents on a specified stainer; status information on a specified reagent, such as expiration date, location, volume, and when placed on stainer 1000; as well as other information.

In some embodiments, security module 1425 offers a one-call function to determine if currently a logged in user 1415 has the appropriate privileges to invoke a particular function. Additionally, in order to accurately correlate user activities with tasks performed, security module 1425 may be provide with a "named user" functionality in which user actions are logged using user login information. In some embodiments, users may also be assigned to a named group and security privileges can be allocated and maintained based on the named group. Membership in a group may confer upon and limit a user to the privileges of that group.

An administrator-level user may be assigned full privileges to create users, assign users to groups, reset passwords, and set global system parameters using system configuration module 1410. Administrator-level users may also set access parameters for sensitive data or protected functions. A function may be deemed protected if modification of its configuration, or of data related to the function, may adversely affect the operation of software; or if data related to or accessible through the function is to be protected from some users. For example, patient privacy laws may require that only certain users be granted access to sensitive patient information. In some embodiments, security module 1425 may call a check access function before allowing users access to protected functions.

Figure 2B:
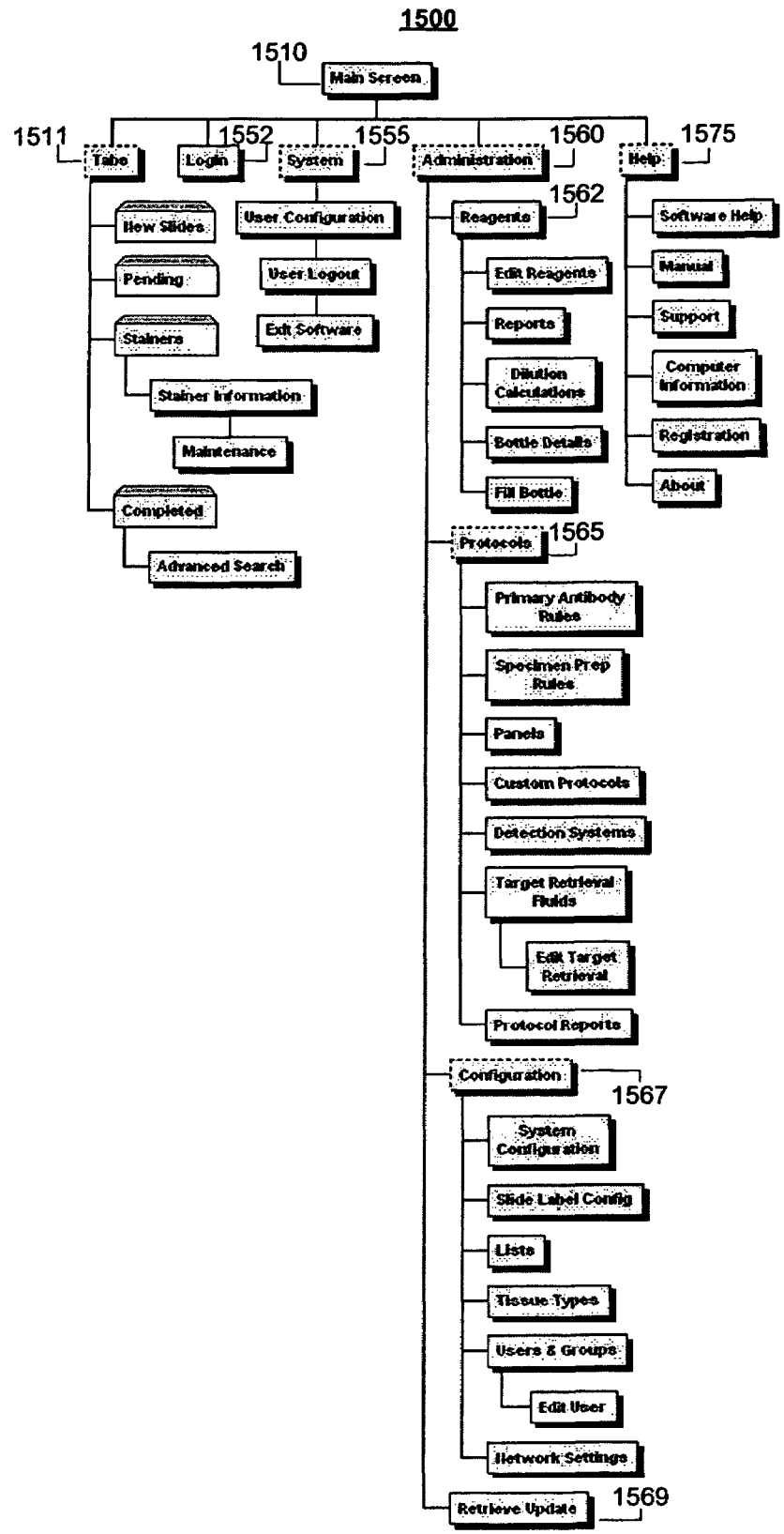
FIG. 2B shows an exemplary menu hierarchy listing some functionality provided by the System Manager.

FIG. 2B shows an exemplary menu hierarchy 1500 listing some functionality provided by the System Manager 1330 through User Interface 1415. In some embodiments, menu choices available to users may be provided through icons, tabs, drop down or pull down menus, or using various GUIs. As shown in FIG. 2B, a user may navigate from Main Screen 1510 through top level menus including tabs menu 1511, login menu 1552, system menu 1555, administration menu 1560, and help menu 1575.

In some embodiments, main screen 1510 displays other windows when a user selects a menu item, and also displays icons or tabs for discrete windows that implement portions of the workflow. For example, tabs may be provided to access screens that allow user interaction with process information relating to new slides, pending slides, stainers, and completed slides. In some embodiments, a container window is created within which other windows may be displayed. For example, main screen 1510 may be a container that holds the individual tab windows, so that individual tab windows are child-windows and displayed within the parent main screen container. In some embodiments, main screen also allows application startup and initialization. In some embodiments, on application startup a configuration file may be accessed and the system configuration parameters may be read from the file. For example, network configuration parameters, which indicate how to connect to the SMS 1320, may be read from a configuration file.

In some embodiments, tab menu 1511 may be provided in the form of a set of tabs along an edge of a GUI window. Clicking on a tab can allow users to view the underlying information. For example, users who select the new slides tab may be shown a data entry interface to enter information about a new slide and the pending slide tab can show pending slides 1045, which have been entered into the system but have not been processed by stainers. In some embodiments, portions of main screen 1510 and lower level screens may be hidden from a user or otherwise disabled by security module 1425, if the user does not have the privileges for access functions provided on that screen. In some embodiments, a user profile for each user may be stored in database 1220 that allows the user's GUI preferences to be restored whenever the user logs in to any computer 1230 running an instance of SM 1330.

Login screen 1552 may provide log in related functions such as allowing users to log in and to set login scripts and a login environment. In some embodiments, system menu 1555 may allow a user to set display or GUI options, change the user's password, and to log out from SM 1330. In some embodiments, help menu 1575 may allow a user to get assistance using the software, including accessing a software manual, searching for terms, and/or by connecting to online help that may be provided remotely. In some embodiments, an administration menu 1560 may allow a user with appropriate privileges to create, retrieve, or alter information pertaining to reagents through reagent menu 1562. For example, a user may enter a new reagent into the system.

In some embodiments, a treatment protocol menu 1565 allows a user to specify rules including, for example, rules for primary antibodies, specimen preparation, target retrieval fluids, and custom treatment protocols. For example, a user may define the fluids, quantities, and temperature for a certain target retrieval process. In some embodiments, the primary antibody rules menu allows users to display and edit the treatment protocol rules for primary antibodies. Configuration menu 1567 permits configuration of system parameters, including slide label configuration; adding or changing users, groups, and user profiles; and changing or updating network settings. For example, slide label configuration allows the format of information printed on machine-readable labels that are affixed to slides 1045 to be specified. In some embodiments, a retrieve update menu 1569 allows users to retrieve any software updates to the SM or other system components.

In some embodiments, user actions such as the creation of a new slide record may cause a database to be updated through SMS 1320. In some embodiments, user actions may be logged for traceability and accounting purposes. In some embodiments, a "wizard" providing a fast and easy way to perform commonly executed tasks may be provided.

Figure 2C:
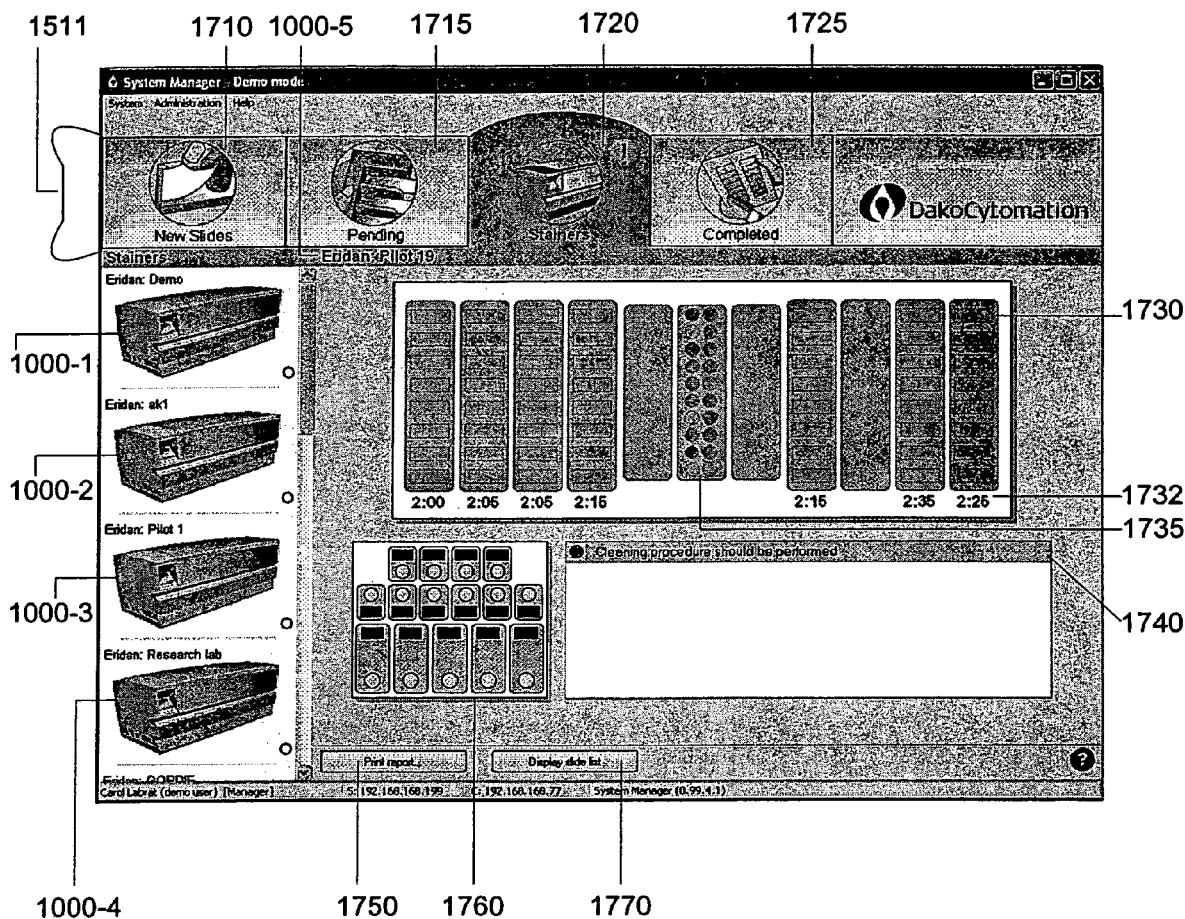
FIG. 2C shows an exemplary user screen for the System Manager.

FIG. 2C shows an exemplary user screen 1700 for the System Manager 1330. Tabs Menu 1511 appears at the top of the screen allowing users to select between tabs for: New Slides 1710, Pending 1715, Stainers 1720, and Completed 1725. As shown in FIG. 3B, Stainers Tab 1720 has been selected and various stainers, such as 1000-1-1000-4 that are part of LAN 1223 are shown on the left hand panel of the screen. Users may select any one of the individual stainers 1000 shown in the left hand panel to obtain additional information about the stainer. Exemplary user screen 1700 indicates that stainer 1000-5, named "Pilot 19" has been selected by the user and details of stainer 1000-5 appear on the screen. The status of slides 1045 on a slide rack 1065 in stainer 1000-5 is shown by columns with icons for the individual slides 1045, as in exemplary column 1730. In some embodiments, icons for slides 1045 may be color coded to indicate their status within a stainer 1000. A slide rack column without slide icons indicates that corresponding slide rack 1065 is empty. At the bottom of each column, a counter 1732 displays the elapsed time on each non-empty rack.

User Interface 1700, as shown in FIG. 2C, also contains a reagent display column 1735, which shows icons for reagent bottles 1080 in stainer 1000-5. A reagent display column without icons for reagent bottles 1080 indicates that the corresponding reagent rack 1060 is empty. In some embodiments, the icons may be color coded to indicate whether reagent bottle 1080 is full, empty or is to be replaced. Fluid display panel 1760 shows the status of various bulk fluid containers 1299 on stainer 1000-5. Dialog box 1740 displays messages related to stainer 1000 including alerts, warnings, or status related information to the operator. Print report button 1750 allows the operator to print various reports pertaining to stainer 1000, slide 1045, reagent bottle 1080, or bulk fluid container 1299 status. Display slide list button 1770 allows details of individual slides 1045 to be displayed. Selection of one of the tabs in tab menu 1511 can cause user interface screens for the option chosen to appear. It should be noted that the screen shown is exemplary only and other configurations of screens and user interfaces are possible.

Figure 3A:
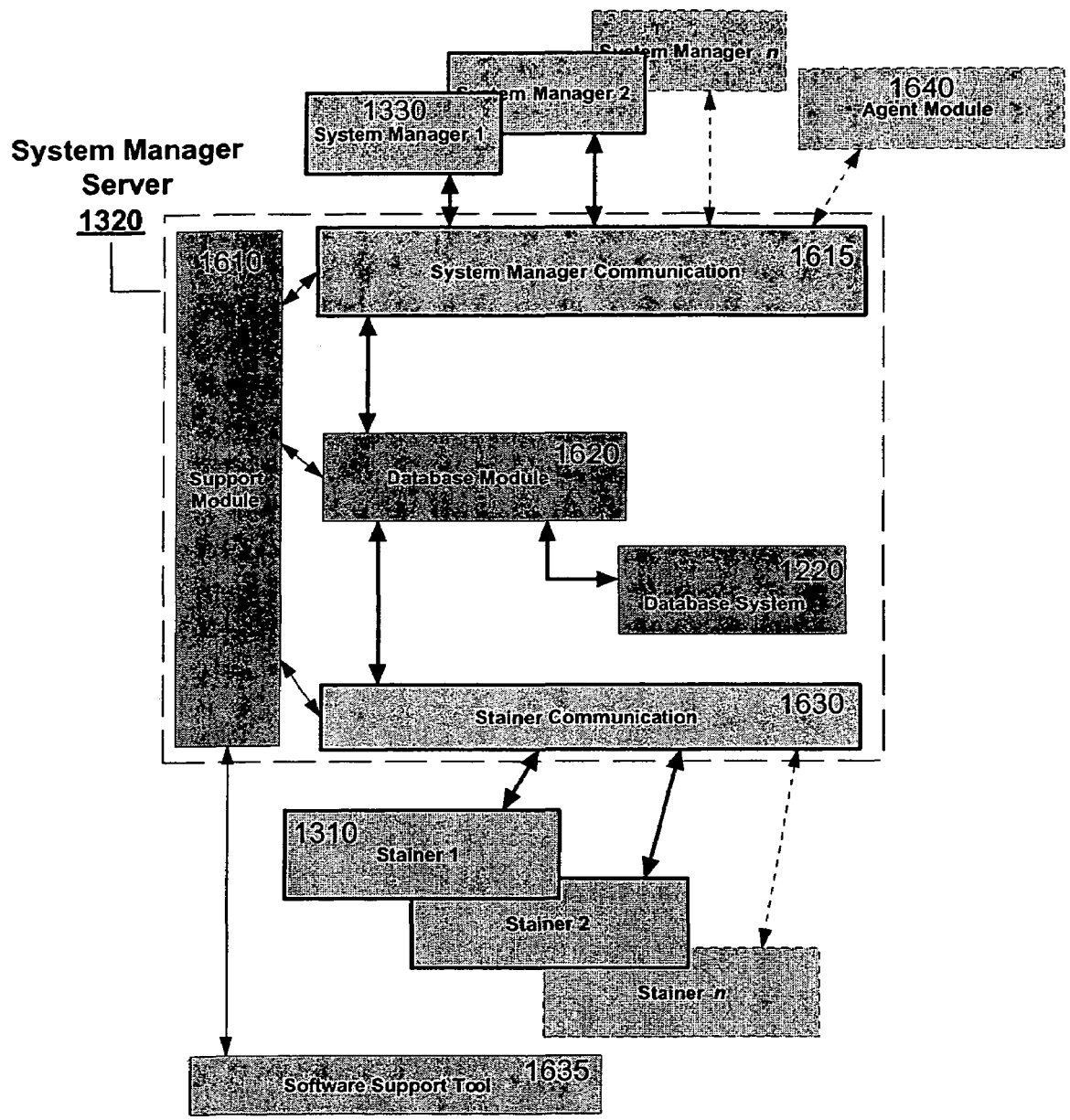
FIG. 3A illustrates exemplary software architecture for the System Manager Server.
Figure 3B:
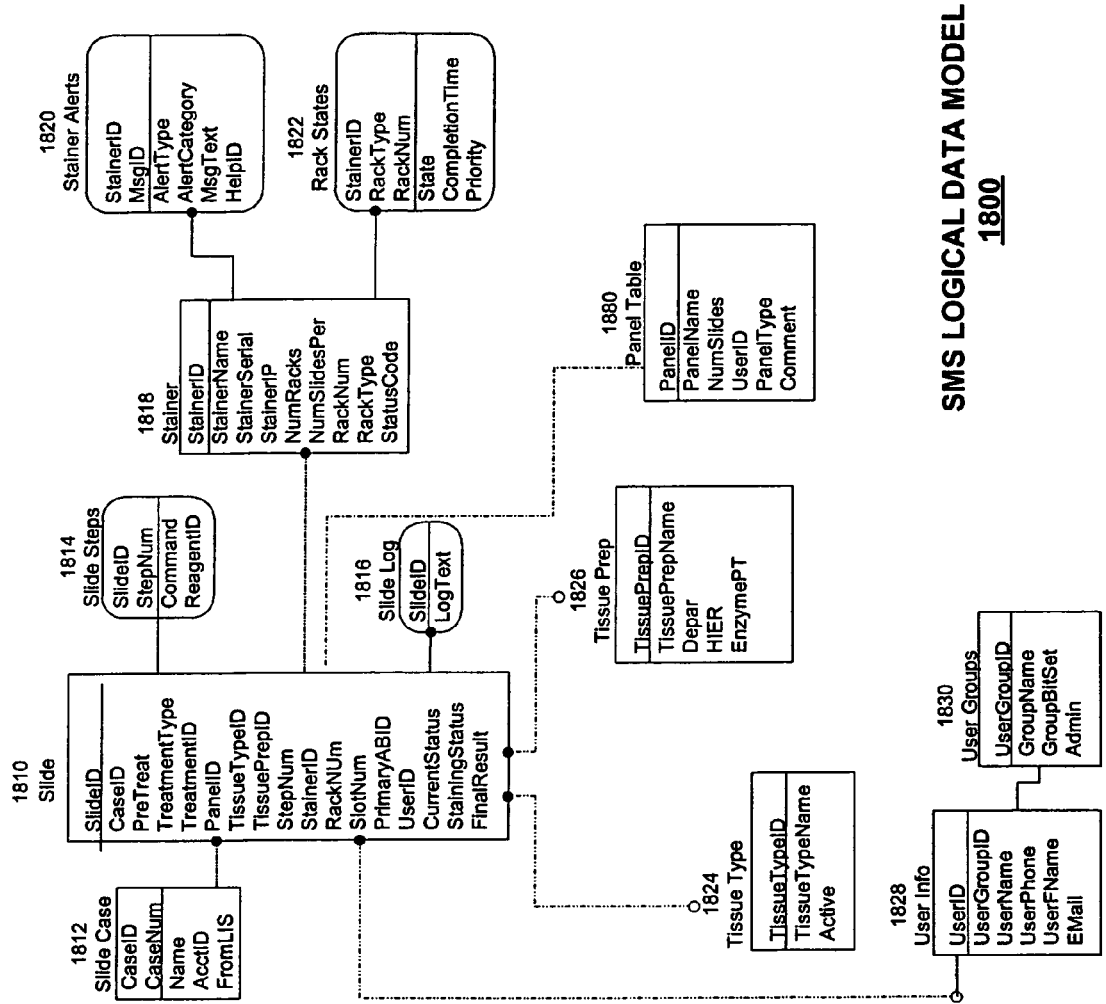
FIG. 3B shows an outline of a logical data model for the System Manager Server.

FIG. 3A illustrates exemplary software architecture 1600 for system manager server 1320. As shown in FIG. 3A, exemplary SMS 1320 includes a system manager communication module 1615 for communication with SM 1330 and a stainer communication module 1630 for communication with SCS 1310. In some embodiments, SMS 1320 performs data handling and processing for the SM 1330 and SCS 1310, and may also process and handle data and messaging communications between SCS 1310 and SM 1330. In some embodiments, SMS 1320 can accept inputs from SM 1330 and/or SCS 1310 and output status reports in response. In some embodiments, SMS 1320 can also connect to and control database system 1220 including maintaining database system 1220 and performing any other database functions.

In some embodiments, SMS 1320 may run as an operating system service. A service application is designed to be always available and provides services to other applications, which may access the provided services over a network such as LAN 1223. For example, on Microsoft Windows based operating systems, SMS 1320 can run as a Window XP Service application so that users need not be logged into Windows XP for the SMS 1320 to be operational. In addition, as shown in FIG. 1F, multiple instances of SM 1330 and SCS 1310 may interact with a single SMS 1320 and its associated database system.

System manager communication module 1615 and stainer communication module 1630 can communicate with multiple individual instances of SM 1330 and SCS 1310 respectively. In some embodiments, instances of SM 1330 and SCS 1310 running on stainers 1000 and computing devices respectively that are part of LAN 1223 can communicate with SMS 1320 through system manager communication module 1615 and stainer communication module 1630 respectively. For example, stainer communication module 1630 may retrieve Slide Detail Data, Slide Protocol data, and/or Global Stainer Configuration data from database system 1220 using database module 1620 and send the data to stainer 1000 in response to a request from stainer 1000. System manager communication module 1615 may also process and forward a request for Stainer Status, Slide Status, Stainer Error or Exception Conditions, and/or Slide Log data from SM 1330 to a stainer 1000, process and relay the response of stainer 1000 back to SM 1330, and update appropriate records in database system 1220 using database module 1620.

Database module 1620 can respond to requests to retrieve and to store data pertaining to slide 1045, reagent bottle 1080, status, and other data. Database module 1620 has information about the logical organization of data tables and queries to fulfill requests for data storage or retrieval from database system 1220. In some embodiments, the data may reside in a Microsoft Access database format, or in another commercial database system format. In some embodiments, such as in a Windows 2000 or Windows XP implementation of SMS 1320, the operating system may support Active Data Objects thus providing native support for the Access database format. In some embodiments, User Interfaces to SMS 1320, as well as all database tables in database system 1220 that provide or deal with user accessed or updated information may be localized to support local languages and/or data formats. In some embodiments, certain data tables may include pre-assigned data such as reagent and treatment protocol names.

In some embodiments, messages exchanged between system manager communication module 1615 and SM 1330 and stainer communication module 1630 and SCS 1310 may be encrypted over LAN 1223. In some embodiments, the exchanged messages can be plain text internal to the modules to facilitate debugging of network communications. In some embodiments, all database transactions may be encrypted to maintain privacy, confidentiality, and security of information in the database. In some embodiments, a log of all data requested from and written to database system 1220 can be maintained.

In some embodiments, data and configuration parameters that affect the operation of the entire system can be maintained by SMS 1320. In some embodiments, SMS 1320 may have a backup and restore utility that can allow for automatic backups on a user-specified, predetermined, or default schedule. In some embodiments, SMS 1320 may search the LAN 1223, auto-discover stainers 1000 and make connection to discovered stainers 1000. In some embodiments, SMS 1320 can also allow stainers 1000 requesting access to connect to it. In some embodiments, different TCP/IP ports may be used to segregate control, status, and diagnostic messages.

In some embodiments, support module 1610 handles the initiation of outbound support connections to manufacturer or service provider support centers and acts as the proxy for support communications with the stainers 1000 and SM 1330. In some embodiments, support module 1610 may interact with a software support tool 1635. Software support tool may allow third party applications to access SMS 1320 via a predefined or standard interface. Support module 1610 permits both automated call out on a periodic basis as well as on-customer-demand call out for support. In some embodiments, a dial-up modem line to an Internet service provider or a direct network connection to the Internet may be used to access manufacturer or service provider support centers.

In some embodiments, support module 1610 and software support tool 1635 provide a general means for a facility operating one or more stainers 1000 to interact with the external world. By appropriately configuring support module 1610 and software support tool 1635, the operator of a stainer facility can receive support and/or exchange information securely and seamlessly with support centers, hospitals, customers, physicians, patients, and other related entities.

To alleviate security concerns, the support system can be configured to initiate support calls only from within the customer's site. This allows a support call to be placed from a facility without opening an inbound port in the facility's firewall. The existence of an inbound port in a network firewall may present a security hazard in some situations. Accordingly, some embodiments of the present invention allow support calls to be placed even in environments where only outbound network connection requests are allowed. Outbound network connection requests are generally more secure and are more likely to be supported by network managers. In some embodiments, all external network communications may be encrypted with a strong encryption algorithm.

In some embodiments, support module 1610 may act as a proxy, or an intermediary between a support technician (or automated support center modules) and end-use software, such as SCS 1310 or SM 1330. In some embodiments, support module 1610 may also directly respond to and/or relay certain commands to SCS 1310 or SM 1330, so that a support technician can also investigate support issues.

In some embodiments, when support module 1610 has connected to a support center, the support module may be asked to login to the support center using a previously provided or default customer number and indicate whether the request is a periodic or on-demand type. The support module can then accept commands from support center software or from a support technician via the support center. For example, in a periodic support call, the support center may issue commands to the support module to obtain system running operational information, including diagnostic files, system configuration information, system logs, and reagent usage statistics. In some embodiments, the transmission of patient-related or other private or protected data may not be allowed via automated support connections. As another example, the support center may transmit or make software updates ready for download by support module 1610.

In some embodiments, when a customer has initiated an on-demand support call, via a dialog on any client, the support module may wait until a support technician connects and is ready to initiate commands. For example, a customer who is receiving support from a technician over the phone may invoke the support module 1610 through an appropriate interface. When support module 1610 connects to the support center, the support technician or a support center software module can take command of the connection and may then issue commands to obtain more information about the SMS 1320 and other software components. When the support session is finished, the support center technician or software can issue a command for the support module to disconnect. In some embodiments, the support module may use an inactivity timer, which can cause the session to be terminated after a preset time length without activity.

Figure 3C:
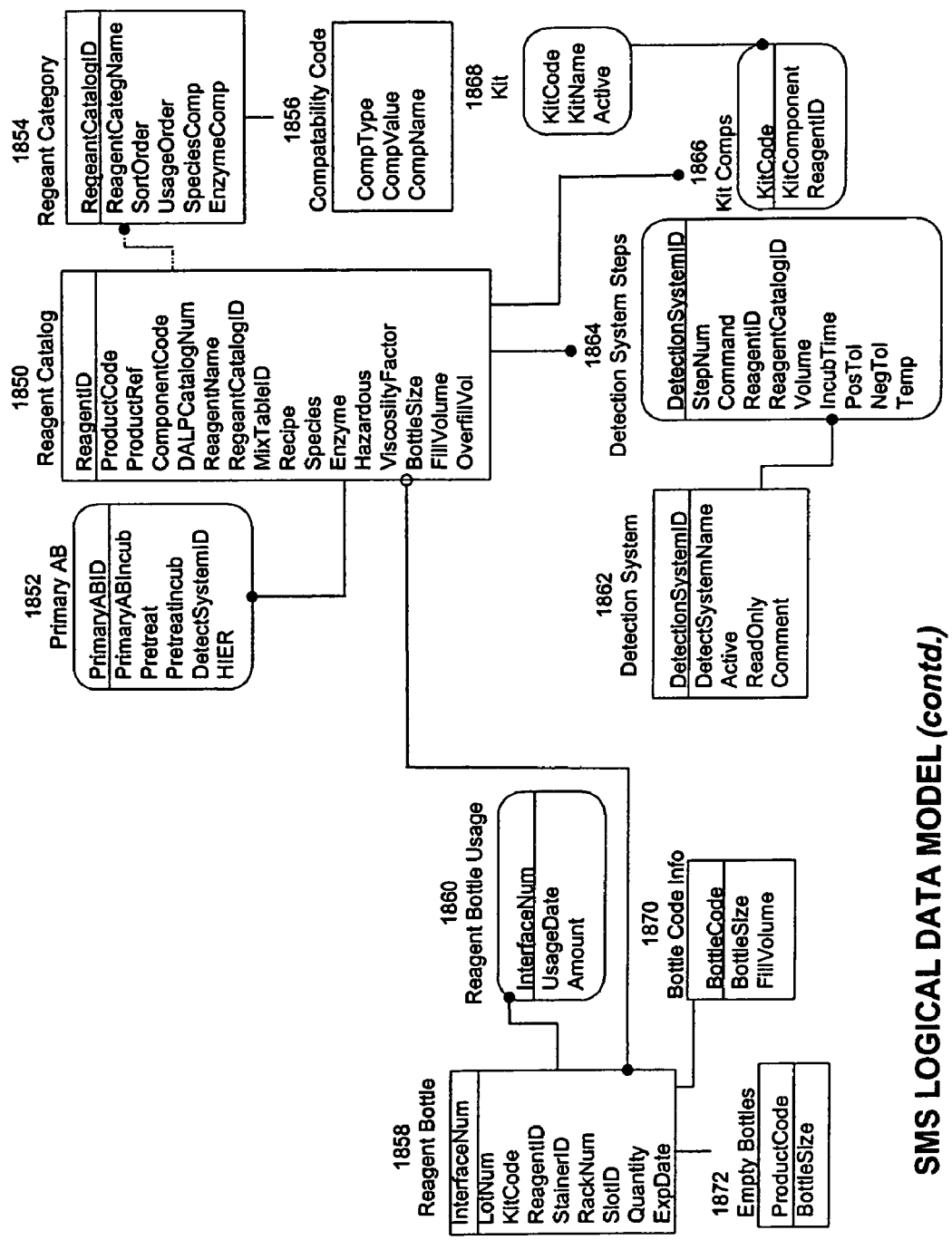
FIG. 3C shows an outline of a logical data model for the System Manager Server.

FIG. 3B and FIG. 3C show portions of an outline for an exemplary logical data model for System Manager Server 1320 showing some of the data tables, data fields, and data records. In some embodiments, data used by SMS 1320 may be normalized and organized as a relational database. In some embodiments, the structure of database 1220 used by SMS 1320 may be based on logical data model 1800. As shown in FIG. 3B and FIG. 3C, exemplary SMS Logical Data Model 1800 indicates the logical organization and inter-relationships between various data tables used by SMS 1320. It should be noted that the tables and organization depicted in FIGS. 3B and 3C are exemplary only and other tables, records and fields may be added or deleted, or the logical data model otherwise modified.

Exemplary Slide Table 1810 is indexed by primary key Slide ID, which uniquely identifies each slide 1045. Slide Table 1810 may also contain identifier CaseID, which is the index to a record in the Slide Case table 1812 that contains the case demographic information. Many slides 1045 on stainer 1000 may correspond to the same case. The FromLIS field in the Slide Case table 1812 can hold an indicator of whether the case information came from an LIS system 1222, or via an LIS Agent.

In some embodiments, the LIS Agent may act as an interface between SMS and external customer-supplied LIS software. In some embodiments of the present invention, the LIS Agent can perform actions analogous to SM 1330 in its capability to enter data into and retrieve data from SMS 1320 and its associated database. In some embodiments, the LIS Agent may be provided additional capabilities, including the capability to interact with the stainers 1000, and other components of system 1200. In some embodiments, LIS Agents may be customized to interact with specific LIS systems. In some embodiments, LIS Agents may also be used to interface to other laboratory instruments, such as exemplary instruments 1296 and/or 1297.

The PreTreat field indicates whether a slide 1045 is to undergo deparaffinization, target retrieval or other pretreatment steps. Treatment Type and Treatment ID fields contain links indicating the treatment type name for which this slide was programmed. For example, the Treatment Type field could refer to a standard test such as the HercepTest, CD30, or a custom named test. The Panel ID field is an index to Panel table 1880 and identifies the panel by which a slide 1045 was added. Panel table 1880 holds information on panels, which are groups of slides 1045 that can be added to stainer 1000 together. If a slide 1045 has a custom treatment protocol then the panel identified by PanelID, may only contain that slide 1045. Tissue Type ID field links to Tissue Type table 1824 and indicates the tissue type of a specimen. Tissue Type table 1824 is a lookup table for the various types of tissue samples that can be stained. In some embodiments, records in Tissue Type table 1824 may be initialized for standard tissue types, but end-users may add more tissue types.

A slide record in Slide Table 1810 may also contain a tissue preparation identifier ("TissuePrepID"), which is an index to Tissue Prep Table 1826. Tissue Preparation Table 1826 is a lookup table for various types of specimen preparations. In some embodiments, records in Tissue Prep table 1824 may be initialized for standard preparation types, but end-users may add more preparation routines. In Tissue Prep table 1824, a Depar field indicates if deparaffinization has been specified for the tissue sample, while the HIER field and the EnzymePT field indicate if target retrieval or enzyme pretreatment respectively have been specified.

In some embodiments, Slide Record 1810 may also contain a Primary Antibody ID field ("PrimaryABID"), which is an index to PrimaryAB Table 1852. Primary AB Table 1852 contains information about the standard incubation times for a primary antibody, as well as information about which detection system and target retrieval to use. In some embodiments, Primary AB Table 1852 contains a DetectionSystemID field, which is an index to Detection System Steps Table 1864. Detection System Steps Table 1864 has information regarding reagent details and command for each step of the treatment protocol associated with the primary antibody.

Slide Steps Table 1814, indexed by the Slide ID and StepNum fields, indicates the command and Reagent ID for each processing step of a particular slide. For example, the command field may hold a processing command such as "Dispense Reagent," where the reagent in question is identified by the contents of the Reagent ID field. The step number ("StepNum") field keeps track of the current step number. The event sequence at each step may be logged and written to SlideLog Table 1816. Slide Log Table 1816 holds the entire slide event log generated by a stainer. The slide log contains information about the type, quantity, and time of application of reagents.

Slide record 1810 may also include a Stainer ID, which is an index to Stainer Table 1818, which contains details about individual stainers. Stainer table 1818 holds information about stainers 1000 coupled to LAN 1223 for a System Manager 1330. In some embodiments, when a new stainer 1000 is added to LAN 1223, stainer 1000 may auto-discover SM 1330 and send out its serial number and IP address, which is recorded in the database by SMS 1320. Stainer Table 1818 includes information about the name of each stainer 1000, the IP address, the number of slide racks 1065 on the stainer 1000, number of slides 1045 in each slide rack 1065, rack type, and rack number ("RackNum"). In some embodiments, the contents of the Status Code field indicate the current status of stainer 1000, which could be one of running, idle, waiting for user intervention, error, or offline. Alerts generated by a stainer 1000 are stored in Stainer Alerts table 1820 and are indexed by Stainer ID and a unique message identifier ("MsgID") for each message generated. A help identifier field ("HelpID") holds an error code that can be looked up using the on-line help menu provided by System Manager 1330. In some embodiments, the contents of HelpID field may be used by a support center technician or an automatic debugging tool to detect and correct problems in offending stainer 1000.

Stainer ID, Rack Type, and RackNum are indexes to a Rack State Table that indicates the state of each slide rack 1065 including its priority and estimated completion time. Stainer ID, Rack Number, and Slot Number are used to indicate the precise location of the programmed slide 1045 once it is introduced into stainer 1000. When slide 1045 is introduced into stainer 1000, the label on slide 1045, which bears machine readable encoded information, can be read and the location of slide 1045 recorded by SMS 1320. In some embodiments, the location of the slide 1045 may be calculated from the location (for example, the X, Y, co-ordinates) of robotic head 1010 at the time when the slide label is initially read. SM 1330 may then query SMS 1320 to obtain the slide information from database 1220.

Slide record also contains a User ID field, which is an index to UserInfo Table 1828 and identifies the user that programmed the slide. In some embodiments, the system may automatically generate the data for a user, such as user name, user phone number and other fields based on information associated with a user's log-in record. User Groups Table, also indexed by UserID, contains information about the group to which a user belongs. In some embodiments, a user may be allowed or denied access to certain software function based on user group membership.

The Current Status field indicates if slide 1045 has been programmed (associated with a treatment protocol), if it has been placed in stainer 1000, if slide 1045 is in-process (the first step of the treatment protocol sequence has commenced), if processing has been completed but slide 1045 is still in stainer 1000, or if processing for slide 1045 has been completed and slide 1045 has been removed from stainer 1000. The Current Status field identifies the specific step in the process flow with which a slide 1045 is currently associated. The Final Result field indicates whether the slide 1045 was processed according to treatment protocol, or was spoiled. A slide 1045 is deemed spoiled if for some reason slide 1045 was not processed within the tolerances specified by the associated treatment protocol.

As shown in FIG. 3C, logical data model 1800 may also contain Reagent Bottle Table 1858. In some embodiments, reagents are added to stainer 1000 in machine-readable labeled reagent bottles 1080 that are placed in reagent rack 1060. The label on each reagent bottle 1080, on which information may be encoded, for example in the form of an Infoglyph™, includes a unique identifier corresponding to a bottle serial number that is stored in InterfaceNum. In some embodiments, the label may also contain information about the Bottle Size. In some embodiments, InterfaceNum may be include a bottle code that could serve as an index to Bottle Code Info Table 1870, which may contain information about bottle size and fill volume.

InterfaceNum also serves as an index to Reagent Bottle table 1858 and allows determination of the lot number ("LotNum") of reagent bottle 1080, kit identifier ("KitCode"), and reagent identifier ("ReagentID"). ReagentID is an index to Reagent Catalog Table 1850 from which additional information about the reagent contained in reagent bottle 1080 may be obtained. In some embodiments, when the label on reagent bottle 1080 in reagent rack 1060 is read, the position of Z Head 1010 on a stainer 1000 identified by StainerID may be used to calculate the slot position ("SlotID") and rack number ("RackNum") of reagent bottle 1080.

ReagentID, which is specified along with Command in Slide Steps Table 1814, identifies the reagent to be dispensed during the specified step StepNum. For the purposes of the database, reagents can include buffer, water, and air. Reagent Catalog Table 1850 identifies the specific reagent from the ReagentID index, by both the Reagent Name and by a Reagent Catalog ID fields. The combination of the fields Reagent Catalog ID and Reagent ID indicates whether the reagent to be used may be taken from a general reagent stock, or if the reagent is drawn from a specified kit.

When a kit is specified, the reagent in question belongs to the identified kit, to ensure the accuracy of test results. If a kit is to be used, the Reagent Catalog ID contains a "KitCode." The KitCode is an index to Kit Table 1868 and KitComps Table 1866, which contain details pertaining to the specified kit. As noted earlier, Reagent ID specifies the actual reagent (from the kit) to be used. If no kit is specified and the reagent may be taken from general reagent stock, then the Catalog ID and Reagent ID have identical values. Kit details, indexed by KitCode, are specified in Kit Table 1868 and Kit Comps Table 1866. Kit Comps Table 1866 specifies the components of each kit. In some embodiments, SMS 1320 and SCS 1310 have the capability of identifying a new kit and automatically generating and assigning a unique kit number to reagent bottles 1080 when they are first introduced in stainer 1000, thus ensuring that reagent bottles 1080 in the kit are utilized as a group.

When a reagent is aspirated for application to a slide, the Usage Date and Amount aspirated is updated in Reagent Bottle Usage Table 1860. Quantity field in Reagent Bottle Table 1858 is also updated. When the Quantity in Reagent Bottle Table 1858 is zero or below a certain useable threshold, the bottle is designated as empty. An Empty Bottles Table 1872 tracks empty bottles. In some embodiments, data in Empty Bottles table may be used to update lab inventory on LIS 1222 and an order may be placed automatically for additional reagents. In some embodiments, an operator may be alerted and asked to replace the reagent bottle.

Detection System Steps Table 1864 is indexed by DetectionSystemID, which also appears in the PrimaryAB Table 1852. A detection system can be generally used with a Primary Antibody reagent selection. Detection System Steps Table 1864 contains information about manufacturer supplied and user-defined detection systems including the actual treatment protocol steps as well as treatment protocol placeholder steps. Placeholder steps may be filled in with selected primary antibodies as well as enzyme pretreatment information where applicable. Thus, using the PrimaryABID field from a slide record, treatment protocol-related information may be obtained by using appropriate tables in database 1220. Detection System Table 1862 contains information about the detection system including its name, whether the system is currently active, and any comments related to the detection system.

In some embodiments, Reagent Category Table 1854 may be used to look up reagent classifications. Such categories could include Primary Antibody, Secondary Antibody, Labeled Polymer, Chromogen, and Counterstain and Reagent Category Table 1854 may be provided as part of database system 1220.

In some embodiments, Compatibility Table 1856 provides information related to the compatibility of reagents. For example, some reagents may only work with mouse antibodies, or with rabbit antibodies, while others may work with both types of antibodies. Compatibility Table 1856 provides information to indicate the compatibility or otherwise of reagents. In Compatibility Table 1856, CompType field indicates if the reagent compatibility value pertains to species or enzyme compatibility, whereas the CompValue field uniquely identifies a particular category of compatibility. For example, if the CompType field indicates species compatibility then the CompValue field could indicate a code for a mouse, or a rat.

In some embodiments, a Mix Table (not shown) may also be present that contains the quantity of constituent reagents to be mixed in order to produce a final mix reagent. In some embodiments, Mix Table may be provided to stainer 1000 for its mixing calculations.

The exemplary data model shown in FIG. 3B and FIG. 3C may be used to create tables in database system 1220 to provide information, including information for system administrators, users, system components, diagnostic and maintenance software, support personnel and software, LIS 1222 applications, and other in-house or third party applications that interact with system 1200. Other tables including tables for holding system configuration parameters, administrative information or to support other functions may be provided.

Figure 4A:
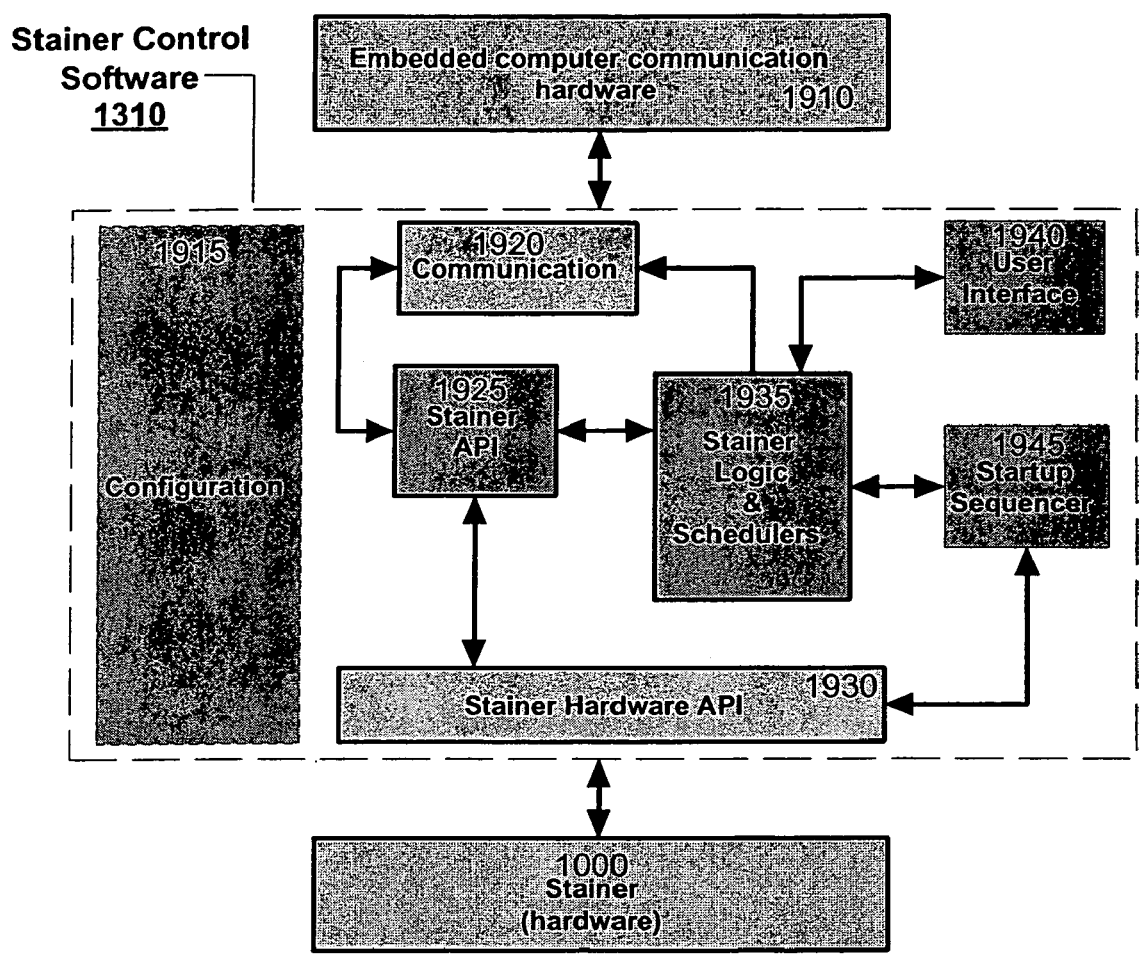
FIG. 4A illustrates software architecture for the Stainer Control Software.

FIG. 4A illustrates exemplary software architecture for the Stainer Control Software 1310. In some embodiments, SCS 1310 may run on a computing system embedded within stainer 1000 and control and coordinate the operations of individual stainer 1000 with other system components. In some embodiments, SCS 1310 may consist of a number of unique autonomous threads or sub-processes. Each thread performs specific tasks and manipulates a number of objects to control and monitor physical device states.

As shown in FIG. 4A, exemplary architecture for SCS 1310 includes communication module 1920, which interacts with embedded computer communication hardware 1910 on stainer 1000, in order to communicate with SMS 1320. In some embodiments, communication module 1920 also receives information and messages from stainer logic and schedulers module 1935 and may also exchange information with stainer API module 1925. In some embodiments, stainer API module 1925 provides an interface for control of stainer hardware at a high level. In some embodiments, stainer API 1925 can translate the high level commands it receives into a sequence of lower level stainer hardware API module calls in order to accomplish the objects of the received command.

Figure 4B:
FIG. 4B shows a block diagram of an exemplary stainer communications subsystem.

FIG. 4B shows a block diagram of an exemplary stainer communications subsystem. As shown in FIG. 4B embodiments of communication module 1920 may include communications component 2001 and computer communications and control component 2007. Communications component 2001 may include two communication interfaces, stainer-server communications interface 2002 for communication with SMS 1320 and diagnostic communications interface 2030 for diagnostic communication related to SCS internal component modules.

In some embodiments, stainer-server communications requests may be generated by internal processes within SCS 1310. Processes within SCS 1310 may queue communications requests within communications interface 2002, which monitors and transmits the requests to SMS 1320. When a response is received, communications interface 2002 sends the response to the appropriate process. Examples of stainer-server communication can include requests for the following: stainer setup information; registering a newly detected slide;

slide record information; slide log information; pending slide information; reagent information; reagent level status; rack queries; pretreatment information; deparaffinization information; target retrieval fluids list; list of all reagent kits; all reagents within a kit; list of all reagents; new reagent kit identifier information; list of bottle identifiers for a kit; and get server date-time.

Stainer-server communications may also include database update requests and/or commands, such as remove reagent rack; reject slide rack; mark slide spoiled; mark slide complete; mark slide drawer open; set target retrieval fluid; set target retrieval or deparaffinization state; update slide state; update reagent state; set slide drawer state; set reagent drawer state; set bulk fluids cart container state; request a simulated reagent bottle (for simulation purposes); reset slide information; set slide drop zone (zone where reagents drop onto a slide); update total processed slide count; add/update an alert; delete an alert; delete all alerts; set kit bottle identifiers; and backup configuration files.

The examples above are exemplary only and other commands and/or requests may be created and added. In some embodiments, SMS 1320 may query database 1220 to obtain the requested information. In some embodiments, database 1220 may be updated with information sent out by stainer 1000, or an operator using stainer 1000.

In some embodiments, diagnostic communications interface 2030 may allow external applications to obtain diagnostics information related to hardware and components on a stainer 1000, when such access has been granted by the system administrator. In some embodiments, the diagnostic interface facilitates a low-level interface where machine status can be queried and various diagnostic commands executed. Diagnostic interface 2030 may be used by a manufacturer or service provider to assist local users in diagnosing and/or correcting problems on stainer 1000, applying software updates and patches, providing technical support, and to ensure the smooth operation of system 1200. In some embodiments, a Software Support Tool ("SST") may be provided to facilitate interaction with stainer 1000 through diagnostic interface 2030.

In some embodiments, a communications protocol interface 2004 may provide functionality for communication protocols, such as the TCP/IP communications protocol, to effect communication with other system components. Port management sub-module 2008 may allow communication ports to be configured to send and/or receive specific types of messages and may direct messages to the appropriate communications port. In some embodiments, different TCP/IP ports may be used to segregate control, status, and diagnostic messages. Embodiments of communications component 2001 allow transactions to be cached and re-transmitted if a communications link has been lost. Accordingly, a system may process all failed, pending, and/or unsent communications requests once the link is restored. In some embodiments, communications component 2001 may be capable of automatic reconnection. In some embodiments, computer communications control sub-module 2007 contains communication hardware device drivers 2008 that control and direct communications hardware 1910 to take actions to effect the actual transmission of data.

In some embodiments, stainer API module 1925 consists of a group of functions and procedures that perform the process of pre-treating and staining slides 1045. In some embodiments, methods performed by Stainer API 1925 are high level in nature and may rely upon many lower level objects to perform their tasks. For example, stainer API may direct robot 1032 to aspirate a specific reagent. As a result, stainer hardware API 1930 may direct robot 1032 to probe washing station 1055, to allow probe 10 to be washed prior to reagent aspiration. The probe washing command in turn may translate a command into a sequence of even smaller steps performed by multiple individual components on stainer 1000.

Stainer hardware API module 1930 controls low-level functionality on various devices and components within stainer 1000. For example, stainer hardware API module 1930 may poll sensors to ensure that all reagent rack doors are closed prior to commencing operation on stainer 1000.

In some embodiments, both stainer API module 1925 and Stainer Hardware API 1930 can also simulate the actions of each of the devices in their control. For example, Stainer API 1930 may model the time taken by probe 10 to apply reagent to a slide, and/or the decrease in available volume of fluid in reagent container 1080. The completion time and/or buffer availability information may be sent quickly to communication module 1920, for onward transmission to SM 1330. The simulation of the actions of system components allows stainer API 1925 and stainer hardware API 1930 to operate in a simulation mode, where no physical actions are actually taken by system components. In some embodiments, stainer API 1925 can return results based on its simulation model to SMS 1320 and SM 1310, which may be unaware that stainer API 1925 is operating in a simulation mode and continue to perform their usual functions. In a simulation mode, the system may be debugged and new procedures tested quickly without risk to or use of system components and expensive reagents. In some embodiments, an accelerated simulation mode may be available, wherein an entire simulation run may be executed in a very short time.

In some embodiments, exemplary stainer logic and schedulers module 1935 contains the logic and decision criteria to trigger, initiate, suspend, report, or terminate actions performed by stainer 1000. In some embodiments, stainer logic and schedulers module 1935 also performs automated background tasks such as waste pull and monitoring. In some embodiments, logic for the control and coordination of robotic and fluidic schedulers in stainer 1000 may also be contained within this component. In some embodiments, robotic head 1032 on stainer 1000 is moved to ensure that reagents are applied to or removed from a slide 1045 substantially within the time period specified by a treatment protocol. In some embodiments, a robotic scheduler controls the movement of robotic head 1032 to ensure that treatment protocol-related constraints are met. In some embodiments, bulk fluids used by stainer 1000 are stored in containers 1299 on fluidics cart 1295 and can be delivered to processing tanks within stainer 1000 at appropriate points in time. In some embodiments, the conduits conveying the fluids to the processing tanks may be limited and shared by several fluid containers. Accordingly, the allocation of conduits is scheduled to ensure that all fluids are ready for delivery at an appropriate time, and that the conduits are adequately flushed to eliminate residues. In some embodiments, a fluidics scheduler controls the allocation of the conduits to fluids.

Exemplary configuration module 1915 holds configuration settings for stainer 1000 including device types, positions, speeds, accelerations, set points, etc. Other SCS modules may request operating parameters from configuration module 1915. For example, stainer logic and schedulers module 1935 may request the speed of robotic head 1032 from configuration module 1915 to calculate a viable schedule for movement of robotic head 1032.

Exemplary startup sequencer 1945 orchestrates stainer 1000 through a safe and orderly startup when it is powered on. In some embodiments, the system can enter a normal running mode after successful completion of the startup sequence. In some embodiments, startup sequencer 1945 may perform one or more of the following functions: system initialization including language selection; preparation of internal data structures and the GUI; checking the operating system and firmware versions and characteristics; locking all loaded drawers; checking and performing tests on motion controller hardware and electronic boards in the stainer; homing the robot; washing the probes; rinsing processing tanks; connecting to a specified System Manager Server 1320 or locating SMS 1320 on LAN 1223; synchronizing date and time with other system components; and starting the schedulers. In some embodiments, exemplary user interface module 1940 provides operational information updates to the built in LCD display and to accept operator input.

Figure 5A:
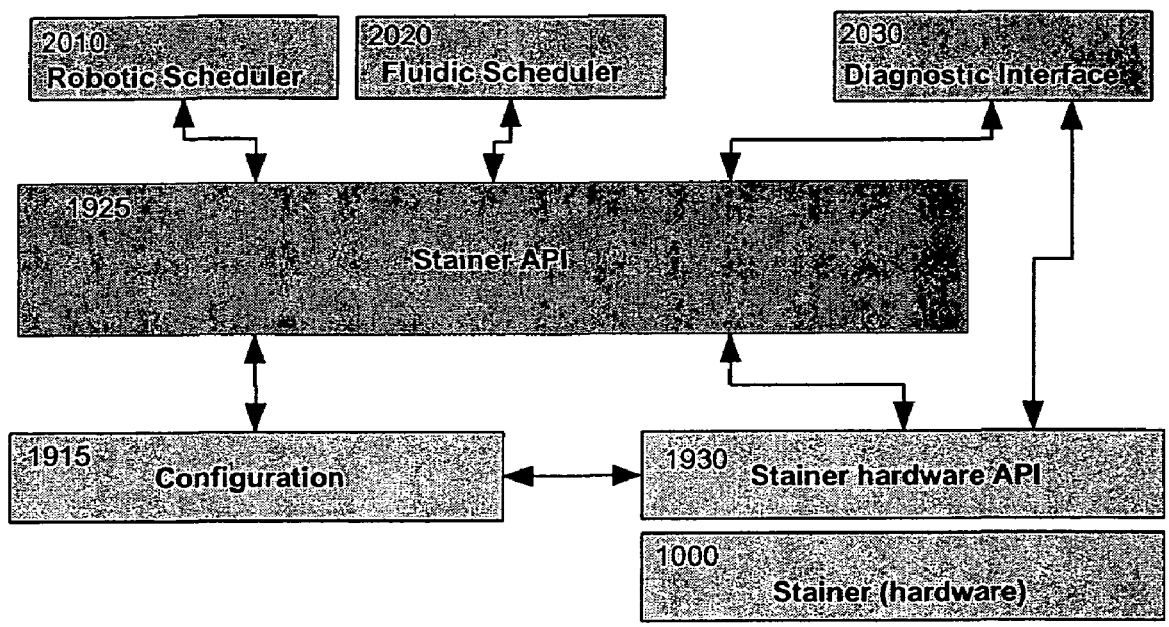
FIG. 5A shows a block diagram of an exemplary API for control of stainer hardware sub-systems.

FIG. 5A shows the interactions of an exemplary Stainer Applications Programming Interface ("API") 2000 for control of functions of stainer 1000. In some embodiments, stainer API 1925 provides a high-level system control and monitoring interface to perform operations for slide processing and pretreatment. In some embodiments, stainer API 1925 may serve as an interface for robotic scheduler 2010 and fluidic scheduler 2020 to invoke and exchange information with routines in diagnostic interface 2030.

In some embodiments, stainer API module 1925 provides a mechanism to access diagnostic interface 2030, which may be part of communications module 1920. Diagnostic interface 2030 facilitates access to hardware on stainer 1000, where machine and component status can be queried and various commands related to diagnostics executed. In some embodiments, diagnostic interface 2030 may exchange data and control information with support module 1610 to facilitate remote monitoring, diagnosis, and support of functions and operations of stainer 1000.

Robotic scheduler 2010 and fluidic scheduler 2020 work through stainer API 1925, which also handles all interfaces to the low level devices through stainer hardware API 1930. For example, in some embodiments, robotic scheduler 2010 may look ahead to determine the robotic head's next rendezvous (the location and point in time where the robotic head 1032 may be utilized next) and may elect to park the robotic head 1032 close to that location by issuing an appropriate command through stainer API 1925.

In some embodiments stainer API 1925 provides access to several routines and functions that are useful for operations relating to the processing and pretreatment of slides 1045. Some of these routines may invoke other routines provided by stainer hardware API 1930. In some embodiments, stainer API 1925 may provide an image acquisition and glyph decoding routine to detect the slides 1045 and decode information on the slides 1045. The image acquisition and glyph decoding routine causes glyphs on labels affixed to slides 1045 or reagents to be read and decoded. In some embodiments, data read from the labels may be sent to SMS 1320 along with slide or reagent location information, and an appropriate slide or reagent record in database 1220 may be updated. In some embodiments, image acquisition and glyph decoding routine may cause a picture of the slide 1045 to be taken by a camera under Z Head 1010, and the image may be stored as part of the slide or reagent record. In some embodiments, the image taken by the camera may be processed using image processing routines to extract information from the glyph, or to determine if a slide or reagent is present.

In some embodiments, for slides 1045 to be stained, slide rack 1065 is lowered until the slides 1045 are resting on platforms. Embodiments of stainer API 1925 may also provide an elevator control function to unlatch and lower slides 1045 to a staining or pretreatment position. Elevator control function may also allow slide rack 1065 to be raised to a latch position in preparation for the opening of a drawer. During normal staining operations SCS 1310 may control temperature and humidity and ensure operator safety in part by locking a front cabinet door on the stainer. Access to a locking function through stainer API 1925 may be provided to lock the front cabinet door. In some embodiments, stainer API 1925 may also provide access to routines to control and stabilize the temperature of a slide 1045 during staining, and to control the temperature of reagent containers in reagent racks. In some embodiments, slides 1045 are tipped vertically to enter the pretreatment processing tank. Embodiments of stainer API 1925 may provide a routine to tip slides 1045 to a vertical position. Embodiments of stainer API 1925 may also provide access to routines for filling, emptying, and heating processing tanks associated with each slide drawer 1040.

In some embodiments stainer API 1925 may also provide access to routines to air blow a slide, or to rinse slides 1045 with buffers or water. Routines accessed through stainer API 1925 may themselves invoke other routines. For example, a slide rinse routine may invoke functions to move the robot to a start rinse position over a particular slide; activate the rinse tool and water pump; move the robot to an end rinse position; and retract the rinse tool. In some embodiments, a buffer rinse allows slide samples to be overlaid with a buffer, which prevents sample deterioration or degradation. In some embodiments, a buffer rinse may be used on slides 1045 between pretreatment and staining, or when a reagent is unavailable, or when the reagent cannot be applied to the slide 1045 within the time allotted by a treatment protocol. Applying buffer to a slide sample preserves the sample until resources such as a reagent or robot 1032 for the next operation are available.

Stainer API 1925 may also provide access to reagent aspiration and dispense routines, wherein a specified amount of reagent may be aspirated from a reagent bottle or the system mixer into probe 10. In some embodiments, robotic scheduler 2010 may be presented with a series of slide dispense tasks, which it prioritizes and sorts. Robotic Scheduler 2010 may then access the reagent aspiration and dispense routine through stainer API 1925 to perform the specified aspiration and to dispense the specified reagent amount from probe 10 onto a slide 1045 or into the system mixer. In some embodiments, the reagent aspiration and dispense routine may in turn call an on-demand reagent mixing routine, which allows a reagent to be created on demand by mixing its constituent reagents in a system mixer. In some embodiments, after the reagent has been mixed, aspirated, and dispensed, the reagent aspiration and dispense routine may cause the mixer to be rinsed, emptied, and dried.

Routines to empty all bottles that belong to a reagent kit when the kit has been designated as empty are also accessible through stainer API 1925. In some embodiments, when any bottle in a kit has been designated "empty," all bottles belonging to the kit are replaced. A kit may be seen logically as a discrete integrated unit, so that operations such as accepting a kit or discarding a kit are performed on the entire kit. Accordingly, in some embodiments, when a bottle within a kit no longer contains a minimum aspiration amount of reagent, the bottle and all bottles belonging to the kit are marked as empty. To prevent usage of reagents remaining in other bottles, the system may be directed to empty all bottles belonging to the kit. Reagents aspirated for the purpose of emptying bottles in a kit may be dumped into waste containers. After each reagent is dispensed on to a slide, reagent probe 10 is washed to prevent carry over from one reagent to the next. Embodiments of stainer API 1925 may also provide access to a probe wash routine to move the robot to probe wash station 1055, lower probe 10 into probe wash station 1055, wash the probe 10 using de-ionized water in probe wash station 1055, and dispose of wash waste.

Stainer API 1925 provides routines to perform the exemplary operations described and other additional operations. Operations performed in response to invocation of stainer API 1925 routines may request and use parameters from configuration module 1915. In some situations, a single operation may also involve calls to a number of individual hardware interface routines using stainer hardware API 1930.

Figure 5B:
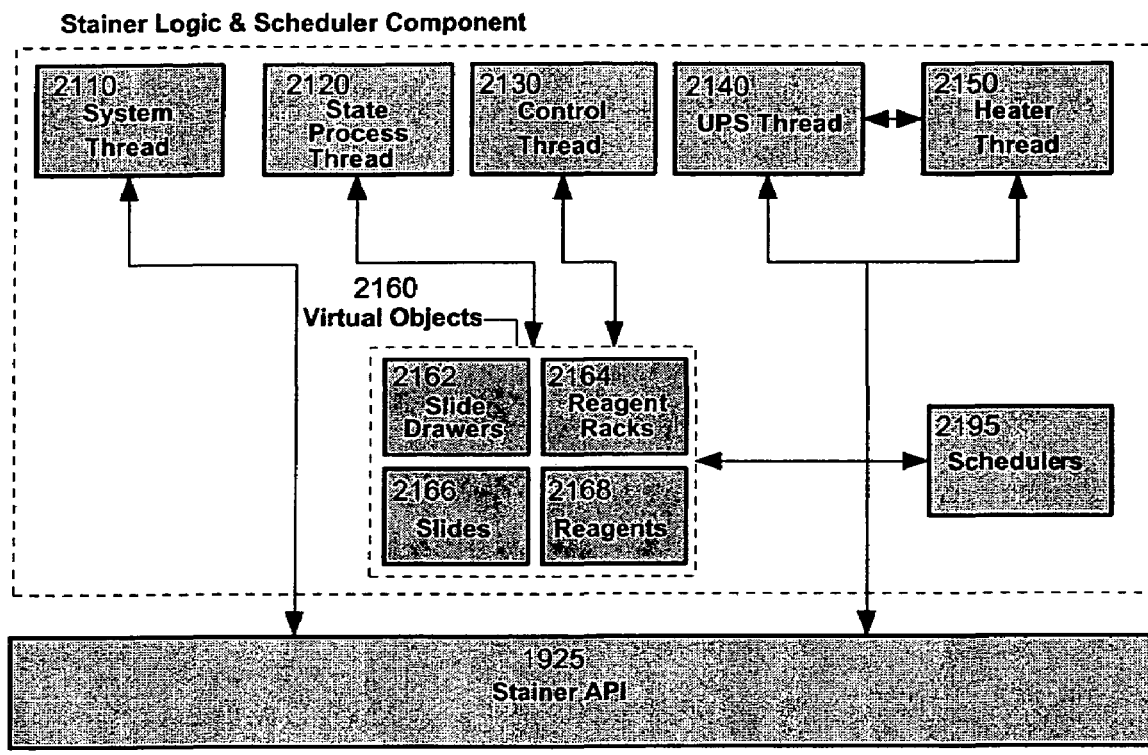
FIG. 5B shows a block diagram of an exemplary stainer logic and schedulers module for control of stainer program threads

FIG. 5B shows a block diagram of exemplary stainer logic and schedulers module 1935 for control of stainer program threads. The various exemplary threads operate on objects including slide drawers object 2162, reagent racks object 2164, slides object 2166, and reagents object 2168. It should be noted that the program threads shown are exemplary only and that other program threads may be added or the program thread structure and logic modified according to some embodiments of the present invention.

In some embodiments, the state of each object, which may correspond to the state of an underlying physical object, is maintained in a field within a data structure and may be controlled by state process thread 2120. Device drivers that interface with a physical object may be responsible for updating the virtual object corresponding to the physical object. For example, a device driver may poll a sensor on a slide drawer 1040, determine that it is open, and make a request to update the status of the slide drawer object. Device drivers are also responsible for executing actions on physical objects that may be desired by SCS components. For example, slide drawers 1040 may be locked prior to processing a request to read glyphs on slide objects 2166. Accordingly, a stainer API 1925 call to read glyphs may result in multiple stainer hardware API 1930 calls, for example to lock slide drawers 1040, move robot 1032, read, and decode glyphs etc. Stainer hardware API 1930 calls may in turn invoke device driver routines that interact with hardware components on stainer 1000 to effect the physical action. For example, a slide drawer driver may instruct slide drawer hardware to lock a slide drawer 1040.

In some embodiments, slide drawers and reagent racks may rely upon the state process thread 2120 to perform steps in operations triggered by operator actions such as opening or closing a drawer, or inserting or removing a reagent rack. When a slide drawer 1040 is opened a field within a data structure associated with the slide drawer object 2162 may be updated to indicate that the slide drawer 1040 is open. In some embodiments, the field indicating the state of the object may also be held within a record for the object in database 1220. For example, state data information pertaining to slide object 2166 may be held in a record within slide table 1810 and could include current process step number as per the treatment protocol associated with the slide. Information to perform operations may also be passed to schedulers 2195, which may include robotic scheduler 2010 and fluidic scheduler 2020. In some embodiments, schedulers 2195 may run as separate threads.

In some embodiments, system thread 2110 provides automatic background processing for waste pull, container level, and electronic board communications and status monitoring. System thread 2110 manages and processes all waste pull requests and ensures that different systems requesting waste pulls get adequate time. In some embodiments, system thread 2110 also monitors all sensors on containers 1299 on fluidics cart 1295, and provides information about fluid level states on containers 1299 to other stainer logic sub-components and to the stainer GUI 1940. Devices that are monitored by the system thread 2110 include all on-board communications and the front door interlock controller. In some embodiments, System Thread 2110 also has the ability to log various sensor conditions at periodic intervals.

In some embodiments, upon launching, system thread 2110 loads a list of all input and output addresses and/or ports and initializes sensors. System thread 2110 may then enter a continuous loop. In some embodiments, on every iteration of the loop, system thread 2110 processes waste pull requests, handles priority waste pulls, monitors input-output ports and on-board communications, and reads sensors on containers 1299 on fluidics cart 1295. In some embodiments, readings of the cart sensors may be averaged over a time period to diminish the effect of fluid motion.

In some embodiments, state process thread 2120 processes event driven states for the slide drawers, reagent drawers, slides 1045, and reagents. In some embodiments, state process thread 2120 periodically calls each slide drawer object 2162, reagent rack object 2164, slide object 2166, and reagent object 2168 to process any pending events, and may accept a value returned from each process call. The value returned from the process call is used to trigger actions using control thread 2130. In some embodiments, each slide drawer object 2162 and each reagent rack object 2164 may operate as an autonomous process that is independent from processes for other drawers and racks. In some embodiments, upon initialization state process thread 2120 loads specified objects into a list before entering a continuous loop. In some embodiments, state process thread 2120 may process states for all of the objects in a list, during every iteration of the loop. If an object returns a code requesting allocation during iteration, state process thread 2120 may request control thread 2130 to execute on the allocation. For example, a reagent specified for a particular treatment protocol step may be allocated to a slide 1045 based on a request to control thread 2130 by state process thread 2120. Allocation establishes a logical connection between the allocated object and the requesting object and may be one of a sequence of steps performed before physical actions corresponding to the allocation are manifested in a stainer.

In some embodiments, control thread 2130 handles reagent allocation executions, stainer GUI 1940 updates and interactions, and provides an interface to frequently accessed objects. In some embodiments, control thread 2130 handles all reagent allocation requests and performs a periodic reallocation. In some embodiments, control thread 2130 also supplies data to user interface 1940 and triggers all user interface updates. For example, user actions on a stainer panel 1020 are recorded by user interface 1940 and passed back to control thread 2130, which makes the change in the specified object. Upon initialization control thread 2130 loads lists of objects and enters a continuous loop. On each loop iteration, control thread 2130 checks for allocation requests and processes the allocation requests. For example, if a reagent allocation request has been made, control thread 2130 allocates the reagent appropriately, and the request may be passed to Schedulers 2195 for prioritization and scheduling. In addition, on each iteration of the loop control thread 2130 may also update GUI objects with the actual states of the real objects in the system and vice versa.

In some embodiments, UPS thread 2140 connects to and monitors any coupled Uninterruptible Power Supplies (UPS) 1298 for power failures. In some embodiments, UPS thread 2140 also handles timing considerations when the line power fails and notifies other logic sub-components when it is time to shutdown heaters and/or stainer 1000 itself. In some embodiments, UPS thread 2140 connects to and periodically monitors a coupled UPS 1298 for line status information. If UPS 1298 reports that line power has failed, the UPS thread 2140 can start monitoring UPS 1298 battery power and can direct the shutdown of processing tank heaters and stainer 1000 itself when the UPS 1298 battery power falls to a critical level. In some embodiments, a log entry may be made just prior to shutdown. On startup, UPS thread 2140 may direct UPS objects to connect to any coupled UPS 1298 and the connections are continuously monitored.

In some embodiments, heater thread 2150 provides a single point interface for all slide drawer processing tank heaters. In some embodiments, the single point interface provided by heater thread 2150 is used in the event that UPS thread 2140 detects a line power loss in order to provide a single shutdown point for all heaters. In some embodiments, all processing tank heater enable and disable requests are fed through heater thread 2140. Upon startup, heater thread 2140 fills its internal lists with the actual heater input/output enable addresses and initializes data structures and flags before entering a continuous loop. In some embodiments, external processes desiring to enable or disable a heater may access processing tank heater enable flags provided by heater thread 2140. On each iteration heater thread 2140 turns on those processing tank heaters that have their flag enabled, and turns off those processing tank heaters whose flags are not enabled. In some embodiments, heater thread 2140 may also be used to effect allocation of limited power resources coupled to stainer 1000 to heaters to load balance the demand on power resources effected by heating tasks.

Figure 6A:
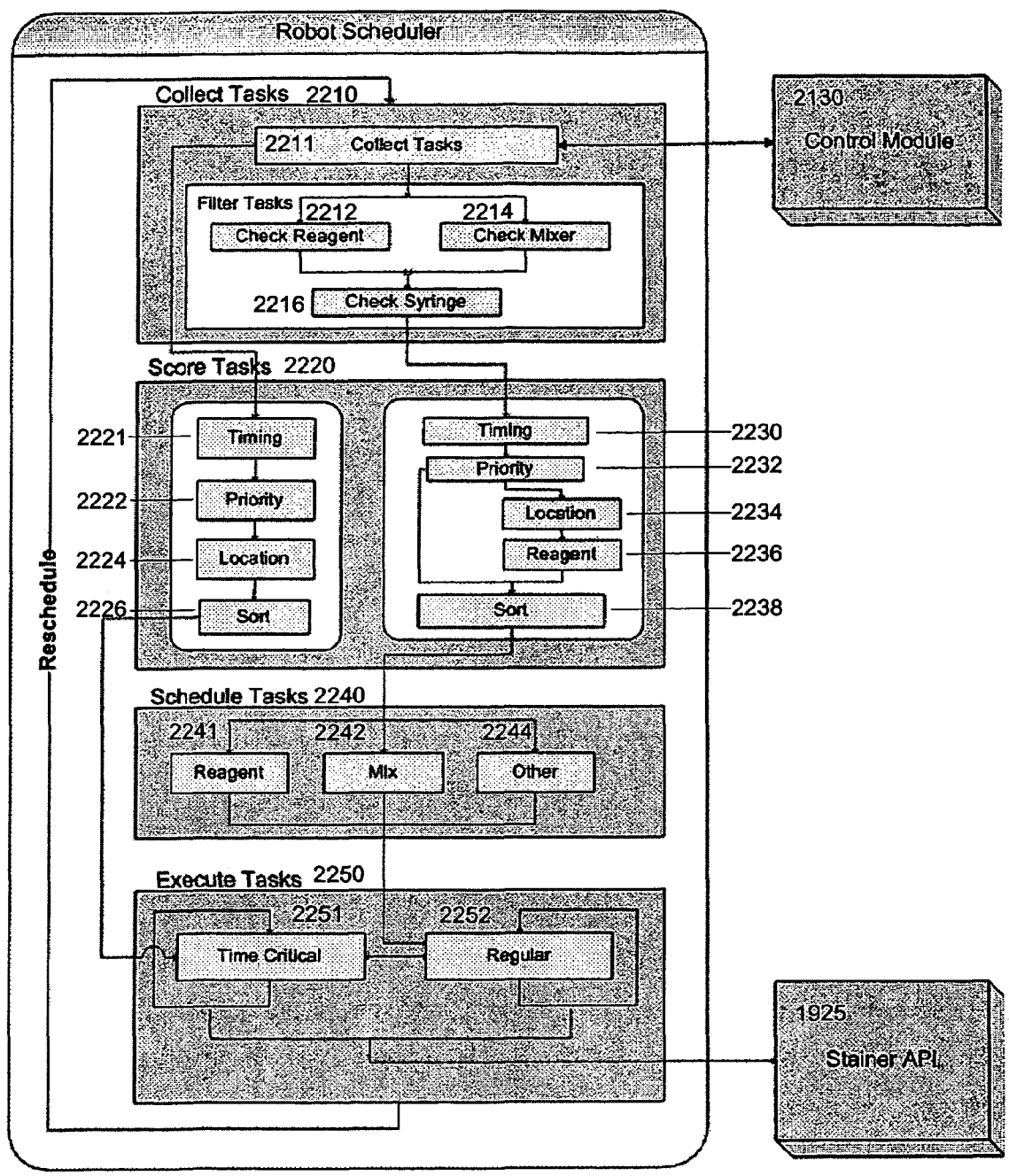
FIG. 6A shows a block diagram of an exemplary robot scheduler.

FIG. 6A shows a block diagram showing interactions between components of an exemplary robot scheduler 2010. The SCS schedulers, including robotic scheduler 2010 and fluidics scheduler 2020, are responsible for conducting staining (robot) operations and pre-treatment (fluidics) operations on stainer 1000. In some embodiments, robot scheduler 2010 may use a dynamic algorithm that continually readjusts the staining tasks that are executed, based on system changes, user actions, and a continuous feedback loop. Embodiments of fluidics scheduler 2020 may also use a dynamic algorithm capable of continually monitoring system changes and scheduling new pretreatment tasks as they are requested. Features provided by the dynamic, self-adjusting scheduling algorithm facilitate the continuous processing of slides. In some embodiments, robotic scheduler 2010 and fluidic scheduler 2020 are instantiated as autonomous threads on stainer 1000 startup and continuously operate to control actions of stainer 1000.

In some embodiments, robot scheduler 2010 manages the coordination of robot 1032 actions, including aspiration and mixing of reagents, for the staining of each slide 1045 within the dynamic environment in stainer 1000. Robot scheduler 2010 analyzes impending steps for each slide, as defined by the treatment protocol for the slide, then intersperses the steps across all slides 1045 and scores (prioritizes) them. In some embodiments, stainer 1000 may contain multiple slide drawers, each of which can contain several slides 1045, and each of these slides 1045 may have its own individual treatment protocol necessitating an individually tailored pretreatment and/or reagent application schedule. From the viewpoint of robotic scheduler 2010 actions are performed on each of the slides 1045 in stainer 1000 within a specified period of time, and in a specific sequence.

In some embodiments, robot scheduler 2010 ensures that robot 1032 has enough time to rinse probe 10, aspirate and/or mix reagents, travel to the location of a slide 1045, and apply the reagent to slide 1045. This sequence of tasks is repeatedly performed for each slide 1045 present in the stainer. Robot scheduler 2010 therefore looks ahead in time for a certain period, and prioritizes or scores tasks that are performed in that period. If robot scheduler 2010 determines that a task may be performed at a later time, the task may be pushed down and re-scored during the next period. In some embodiments, robot scheduler 2010 can work on the highest scored task first and then proceed to other tasks in order of priority. In some embodiments, the highest scored task may be the most time critical task. In some embodiments, if robot scheduler 2010 determines that robot 1032 does not have sufficient time to aspirate and apply reagent to a slide 1045, a buffer may be applied to slide 1045 to preserve the sample and the task marked to be re-scored during the next period.

In some embodiments, the speed at which robot 1032 can perform actions and number of slide slots provided in stainer 1000 are matched to ensure that the spoiling of slide samples on account of treatment protocol violations is extremely rare or non-existent. In the unlikely event that robot 1032 is unable to perform its actions within the specified period or incubation tolerance for a treatment protocol step (for example, due to a transient mechanical problem), the violation is logged, but processing of slides 1045 is continued. When the processing of slides 1045 in a slide rack 1065 containing spoiled slide 1045 has been completed, a qualified technician can review the log to determine the nature and seriousness of the treatment protocol step tolerance violation, and also view the resulting stained sample to determine if the results are acceptable.

In some embodiments, robot scheduler 2010 can continually monitor all system events and re-adjust schedules in response to any changing events to allow all slides 1045 to complete properly. In some embodiments, scoring and scheduling may be performed in accordance with algorithms described below. In some embodiments, robot scheduler 2010 and fluidics scheduler 2020 may operate to maximize throughput of stainer 1000, as measured by the total number of slides 1045 successfully processed in a given period of time. In some embodiments, robot scheduler 2010 may recompute schedules to respond to dynamic changes in the load of stainer 1000 such as may occur when new slide racks are loaded and rack priorities are changed. In some embodiments, robot scheduler 2010 may handle expected and unexpected failures and errors by trying to isolate affected subsystems and save slides 1045 from spoiling.

As shown in FIG. 6A, embodiments of robotic scheduler 2010 may include collect tasks module 2210, score tasks module 2220, schedule tasks module 2240, and execute tasks module 2250. In some embodiments, collect task module 2210 interfaces with control thread 2130 to obtain a list of all pending robot tasks. Robot tasks include all tasks that utilize robot 1032 or tools associated with the robot, such as reading a reagent label using the camera, tipping a slide, or dispensing reagent on a slide 1045 using syringe pump 1015 and probe 10. In some embodiments, tasks that are to be performed within the next time interval are identified and collected while all the others are filtered out.

In some embodiments, score tasks module 2220 calculates a numerical score for each collected task based on several predefined categories, such as rack priority, incubation expiration time, or reagent availability. In addition, each category may be ranked by its relative importance. Once scored, the tasks are sorted in descending order of task scores, so that high scoring tasks are prioritized and appear at the top of the sorted list.

In some embodiments, schedule tasks module 2240 selects and groups tasks to be performed in the next time interval, and generates additional tasks for the syringe pump 1015, probe 10, or mixer 1050 subsystems in the context of their current state. In some embodiments, schedule tasks module 2240 may optimize the slide staining process by reducing idle delays. In some embodiments schedule tasks module 2240 may operate to increase responsiveness and flexibility so that tasks may be re-scheduled under the dynamically changing conditions. Execute tasks module 2250 interfaces with the Stainer API module 1925 to physically execute scheduled tasks. In some embodiments, execute tasks module 2250 may preempt scheduled tasks with other time-critical tasks due for immediate execution.

In collect task routine 2211, a list of all currently pending robot tasks gathered from the top of each subsystem queue is obtained from control thread 2130. In some embodiments, objects 2160 may be associated with slides 1045, slide drawers, reagents, and reagent racks: For example, slide object 2166 pertaining to a slide 1045 may include queues of pending tasks associated with the slide. Likewise, slide drawer object 2162, reagent object 2168, and reagent rack object 2164 may include queues of pending tasks associated with slide drawers, reagents, and reagents racks respectively. In some embodiments, queues may be implemented as first-in first-out lists. For example a slide queue might contain a task to dispense reagent, and a slide drawer queue might contain a task to read all slide labels in the rack.

In some embodiments, check reagent routine 2212, check mixer routine 2214, and check syringe routine 2216 are used to filter out tasks associated with reagents, mixers, and syringes respectively, where prerequisites for the tasks are lacking. Thus, tasks whose prerequisites cannot be satisfied because of reagent, syringe, or mixer unavailability are filtered out. For example, if reagent A is not present in reagent rack 1060 then a task requiring reagent A may be filtered out. Filtering ensures that the list of tasks submitted for scoring, sorting, and scheduling are those that can run to completion if scheduled. In some embodiments, data associated with a task could include the task's earliest execution time, latest execution time, task command, and task status.

In some embodiments, collect task routine 2211 may classify tasks as time-critical or regular tasks. Time-critical tasks may execute at specific times and have tight tolerances. Regular tasks are not time-critical and their tolerances are considerably more generous. In some embodiments, collect task routine 2211 may also create, use and update lists of time critical and regular tasks available for scheduling. In some embodiments, buffer and water rinse tasks may be classified as time-critical. A buffer rinse protects samples on slide 1045 from drying out therefore applying or re-applying a buffer rinse at specified intervals is considered time-critical. Accordingly, if a buffer solution on slide 1045 is near its expiration time and there is insufficient time for dispensation of the next reagent, a new buffer rinse task may be created.

In some embodiments, score tasks module 2220 calculates a numerical score that is used to prioritize potentially executable tasks for execution. In some embodiments, tasks submitted for scoring are analyzed taking into account the type of each task (e.g. rinse or dispense), their spatial properties such as slide location, temporal properties such as reagent incubation period expiration, other properties such as rack priority, and properties relating to system or subsystem state such as the reagent currently in a syringe.

In some embodiments, task and subsystem properties are classified into separate scoring categories with individual importance rankings. For example, for buffer and water rinse tasks the earliest and latest time of rinse application with respect to current system time may be accorded a high weight, the user selectable rack priority may be weighted normal, and the location of a slide 1045 in stainer 1000 may be accorded a low weight. In some embodiments, the high, normal, and low weights correspond to actual numerical values from which a score may be calculated. For example, to score rinse tasks with respect to reagent incubation time, a scoring routine may compute different scores based on whether the earliest rinse time for the sample has passed. Thus, before the earliest rinse time the newly computed sub-score may be given by:

$$NewSubScore = \frac{CurrentSubScore}{2} - \frac{EarliestRinseTime - CurrentTime}{NormalizingFactor}$$

whereas, after the earliest rinse time has passed, the newly computed sub-score may be given by:

$$NewSubScore = CurrentSubScore - \frac{EarliestRinseTime - CurrentTime}{NormalizingFactor}$$

As can be seen from the example above the priority of the rinse task may be significantly higher after the earliest rinse time has passed.

In the scoring process multiple sub-scores from the categories relevant to each type of task are weighed by their relative ranking and combined into a single composite numerical score for each task. For example, in some embodiments, timing routine 2230, priority routine 2232 (which, includes location routine 2234), and reagent routine 2236 may calculate sub-scores related to the various task properties. The overall score obtained by combining the weighted individual sub-scores ultimately determines when the task can be scheduled and executed in relation to other competing tasks. For example, an overall score may be computed using the following equation.

OverallScore=(SubScore1*WeightingFactor1)+ . . . + (SubScoreN*WeightingFactorN)

It should be noted that the computations above are exemplary only and other functions, including step functions, quadratic or higher order functions, or combinations of superimposed functions may also be used to compute the sub-scores and overall score. In some embodiments, the effect of the scores on stainer 1000 may be modeled using the simulation capabilities of Stainer API Module 1925 and Stainer Hardware API 1930 prior to actual use.

In some embodiments, time-critical tasks are not passed through any filters, they are immediately advanced to scoring module 2220 using timing routine 2221, priority routine 2222, and location routine 2224 and an overall score calculated. In some embodiments, the overall scores are sorted using sort routine 2226 and the prioritized task list immediately advanced to execute routine 2251 within execute module 2250. In some embodiments, the scoring of time-critical tasks may be based primarily on the execution time of each task. For example, time critical buffer and water rinse tasks may be scored using a different set of categories and the sub-scores may be weighed differently. Thus, for time-critical tasks, the earliest time of rinse application with respect to current run time may be accorded a high priority.

Sorting routine 2238 sorts tasks based on their overall scores and submits the prioritized task list for scheduling. In some embodiments, scheduler tasks module 2240 examines the sorted list of tasks and schedules actual tasks and generates any prerequisite tasks. In some embodiments, scheduler tasks module 2240 may process the sorted task list starting at the highest scoring task but then select one which can be executed immediately or whose preparatory tasks are capable of immediate commencement. In some embodiments, tasks directed to common functions may be grouped together using reagent routine 2241, mixing routine 2242, or other routines 2244 to minimize the generation and execution of additional tasks. For example, a reagent dispense task may use the syringe, use a specified quantity of a reagent of specific type, and may specify that probe 10 be washed and the reagent aspirated before dispensing can take place. In some embodiments, preparatory tasks may be performed just in time in order to minimize potential delays such as waiting for the correct reagent or mix. Performing preparatory tasks just in time also avoids locking the scheduler into a specific sequence of actions ahead of time. In some embodiments, just in time scheduling may rely on a prediction of how long each task may take to execute. In some embodiments, parameters affecting task durations may be determined at the time of calibrating stainer 1000 and stored in memory.

In some embodiments, execute task module 2250 executes time-critical and regular tasks using time-critical routine 2251 and regular routine 2252. In some embodiments, scheduled tasks submitted for execution may be turned into lower level commands issued to stainer 1000 to perform physical actions. In some embodiments, translation of high level tasks to lower level tasks may be accomplished by calling appropriate functions within stainer API module 1925, which may encapsulate and abstract lower level functionality. In some embodiments, the scheduled execution of a regular task can be preempted at any time, if a time-critical task requests an immediate execution.

Figure 6B:
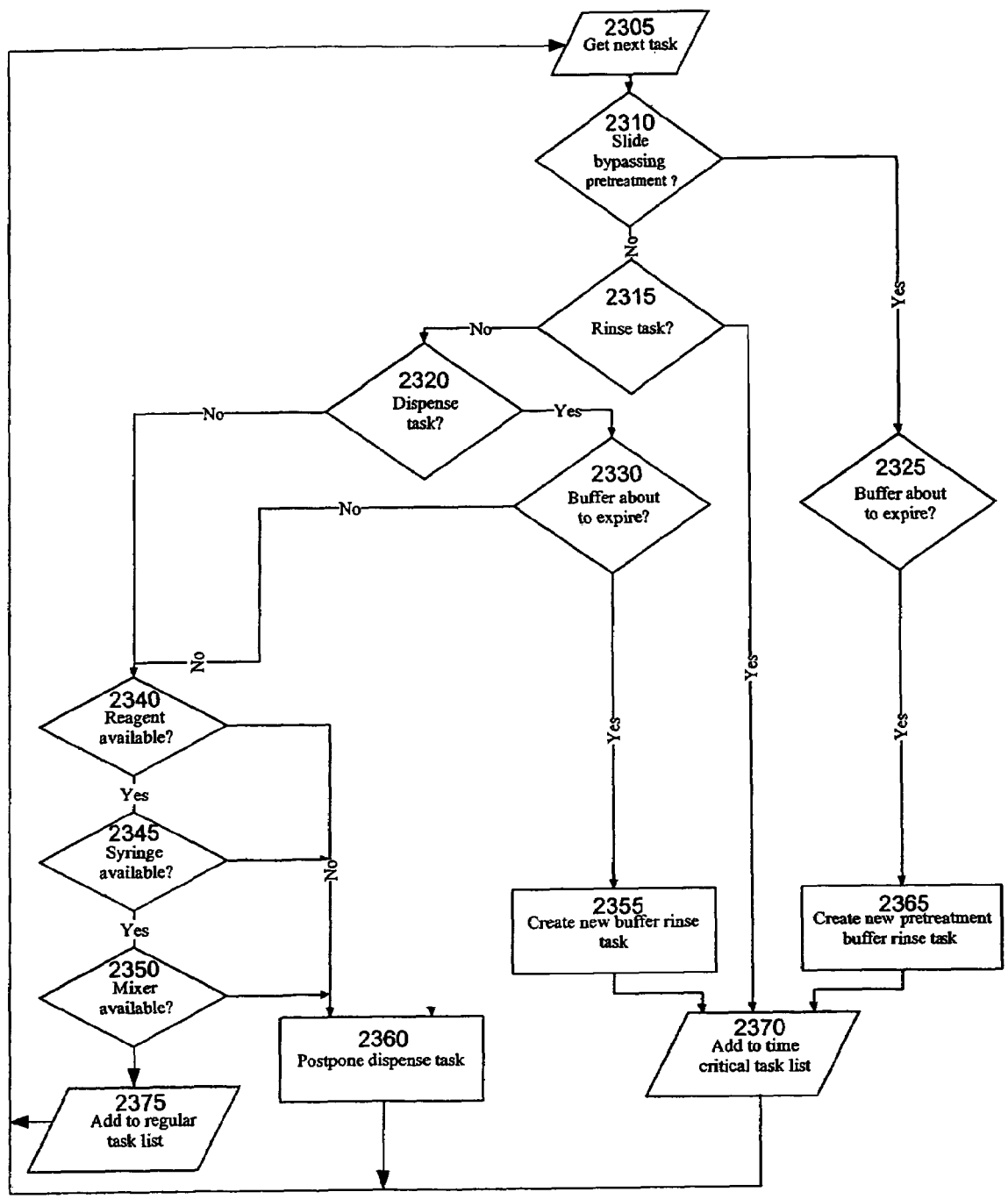
FIG. 6B shows a flowchart of an exemplary method for determining regular and time-critical task lists for a robotic head.

FIG. 6B shows a flowchart of an exemplary method for determining regular and time-critical task lists. As shown in FIG. 6B, the algorithm loops continuously and the next task is processed in step 2305. In step 2310, the task is examined to check whether it pertains to a slide 1045 bypassing pretreatment. In step 2325, the task may be further examined to check whether it pertains to a buffer about to expire and, if this is the case, then a new buffer rinse task is created in step 2365 and the buffer rinse task is classified as time-critical in step 2370. If the task is not a slide 1045 bypassing pretreatment then it is examined in step 2315 to determine if it is a rinse task. If the task is a rinse task then is classified as time-critical in step 2370.

In some embodiments, if the task is not a rinse task, then in step 2320 it is examined to determine whether it is a dispense task. If in step 2330, the dispense task is determined to relate to a sample whose buffer is about to expire and for which reagent may not be applied in time then, in step 2355 a new buffer rinse task is created and the buffer rinse task is classified as time-critical in step 2370. If the dispense task does not pertain to a sample whose buffer is about to expire then reagent availability is determined in step 2340, followed by syringe 1015 availability in step 2345 and mixer 1050 availability in step 2350. If all of these objects are available (or, if the mixer 1050 is not used by the task) then the task is added to the regular task list in step 2375. If any of the objects is unavailable then the task is postponed, in step 2360. Once a task has been processed, the algorithm returns to step 2305 to process the next task on the sorted list.

Figure 6C:
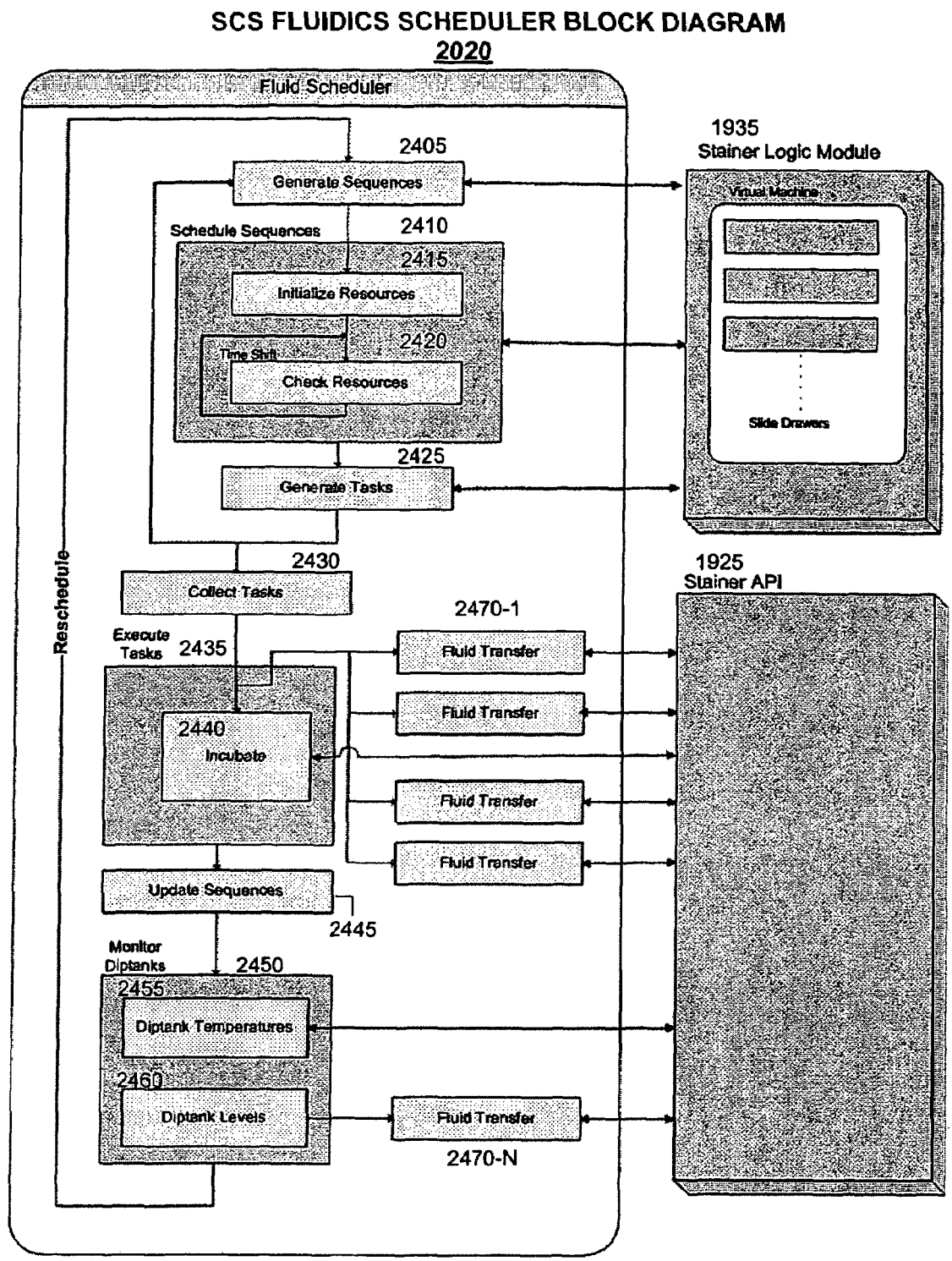
FIG. 6C shows a block diagram of an exemplary fluidics scheduler.

FIG. 6C shows a block diagram of an exemplary Fluidics Scheduler 2020. In some embodiments, fluidics scheduler 2020 may be an autonomous process and implemented as one or more threads, which run in a continuous loop within the context of SCS 1310. In some embodiments, a fluidics scheduler thread may run independently but may query other components for the data to create schedules and to coordinate task execution related to the schedules. In some embodiments, stainer 1000 may have a limited set of conduits to convey fluids to and from the bulk fluids cart, or to remove waste from the stainer. Additionally, conduits and chambers within stainer 1000 may be periodically flushed to ensure that there is no reagent or fluid cross-contamination. Embodiments of fluidics scheduler 2020 operate to ensure that the conduits are available to fluids in a manner that ensures that fluids can be delivered to or removed from appropriate locations in stainer 1000 at appropriate points in time. Fluidics scheduler 2020 allows the time-sharing of conduit resources to facilitate various operations performed by stainer 1000.

In some embodiments, the fluidics subsystem may have multiple conduits each of which may be controlled by multiple individual valves and pumps. Accordingly, fluidics scheduler may create and implement schedules permitting multiple actions to be taken in parallel, such as directing fluids along different fluid paths simultaneously. In some embodiments, individual control systems associated with the conduits may be inherently parallel. For example, a valve may stop the flow of fluid in one conduit, while another conduit is simultaneously removing waste fluid from the stainer. Therefore, in some embodiments, fluidics scheduler 2020 may direct the execution of individual actions by coordinating a dynamic collection of autonomous threads, each responsible for executing distinct individual tasks.

In some embodiments, a single run through fluidics scheduler 2020 may consist of checking each slide drawer object 2162 for a pending pretreatment request, generating a sequence of fluidics actions for each such request, and then directing the execution of any sequenced action when its scheduled time has arrived. Fluidics scheduler 2020 may then loop back and repeat the cycle above.

In some embodiments, slide drawer object 2162 may provide information related to a slide drawer 1040 including drawer identification information, drawer state, drawer pretreatment related information, drawer pretreatment sequence, drawer deparaffinization treatment protocol steps, drawer target retrieval treatment protocol steps, pending tasks, and processing tank fluid level which may be used by fluidics scheduler 2020 in making scheduling decisions. In some embodiments, a schedule may include task related information such as an identifier, task originator, task command, task status, source and destination containers, fluid type, task start time, and duration. In some embodiments, fluidics scheduler 2020 may use a list of shared fluidics resources, and interface with stainer API module 1925 and stainer logic and schedulers module 1935. In some embodiments, exemplary task commands could include pause, fill processing tank, empty processing tank, incubate in processing tank, heat processing tank, cool processing tank, flush processing tank, replenish processing tank and wait in processing tank. In some embodiments, commands may be executed by appropriate calls to stainer API module 1925. Each command may perform numerous lower level individual steps to carry out the command. For example, an empty processing tank command requiring a fluid transfer, may cause valves to be opened, the pump to be started, the pump stopped when fluid transfer has completed, and the valves closed when the action has terminated.

To illustrate the operation of fluidics scheduler 2020 an exemplary sequence of operations is described. For example, when a rack of slides is newly loaded into stainer 1000 and determined to require deparaffinization, fluidics scheduler 2020 obtains the treatment protocol steps and uses them to generate a comprehensive sequence of fluidics states. Accordingly, a five minute incubation of slides 1045 in a processing tank filled with solvent fluid may be part of a sequence. The incubation step is mapped into three distinct fluidics states: filling the processing tank from a solvent bottle, incubating the slides 1045 for the specified five minute duration and draining the processing tank contents. During the period when the two fluid transfer phases are in progress, other processing tanks cannot use the conduit that is being used to effect the fluid transfer. However, the processing tanks may make use of any free conduits to perform other fluidic transfers. In some embodiments, some conduits may have dedicated functions. For example, one conduit may be dedicated for solvents, another for alcohol, and a third for water. Other resources such as the processing tank heating system, which may be used during the five minute incubation period, are nonexclusive-use resources. Thus, a number of processing tanks may be heated simultaneously. After sequences have been generated resource conflicts are resolved to create a schedule. In some embodiments, fluidics scheduler may ensure that the pretreatment process is not interrupted after it has been commenced.

As shown in FIG. 6C, exemplary fluidics scheduler 2020 includes generate sequences module 2405, schedule sequences module 2410, generate tasks module 2425, collect tasks module 2430, execute tasks module 2435, update sequences module 2440, and monitor processing tanks module 2450. In some embodiments, execute tasks module 2435 in exemplary fluidics scheduler 2020 may also generate several fluid transfer task execution threads 2470-1 through 2470-N to direct the performance of tasks scheduled for execution.

In some embodiments, generate sequences module 2405 interfaces with stainer logic and schedulers module 1935 and examines active slide drawer objects 2162 to determine whether there are pending requests for pretreatment or processing tank rinse. If a pending request exists then generate sequences module 2405 may use the appropriate treatment protocol to generate a sequence of steps for scheduling and execution. In some embodiments, the sequence of steps may relate to deparaffinization and/or target retrieval. An exemplary sequence of steps generated by generate sequences module 2405 may include information such as steps related to processing tank filling and draining, processing tank rinses, whether slides 1045 are tipped during the process, and the resources for each step in order to provide the scheduler with sufficient information to make decisions. An exemplary sequence may include steps such as: fill processing tank with target retrieval fluid; turn on the processing tank heater and heat for I minutes; turn off heater and cool for J minutes; drain processing tank to waste; fill processing tank with water; incubate in water for K minutes; and drain processing tank to waste.

In some embodiments, schedule sequences module 2410 schedules drawer pretreatment sequences in order to optimize the use of shared fluidics resources. In some embodiments, schedule sequences module 2410 may develop a schedule in order to reduce the duration of pretreatment phase for each drawer. Sequences may be run in parallel if they use different resources, or use the same resources at different time intervals. In some embodiments, currently executing fluidics sequences may get priority with respect to claims on shared resources.

In some embodiments, utilization factors may be associated with each resource. When a resource may be shared its utilization factor is increased proportionately upon every allocation. When a resource is exclusive its utilization factor is 1 (100% utilization) whenever it is allocated. In some embodiments, each shared resource requested by the scheduled sequence may be checked at critical points by calculating its total utilization factor. In some embodiments, if a resource allocation would cause the utilization factor for a resource to exceed 100% at any point in time, the sequence being scheduled may be time shifted to resolve the conflict. Schedule sequence module operates iteratively and is based in part upon time at which pretreatment requests were made by each drawer.

In some embodiments, schedule sequences module 2410 obtains all sequences already scheduled and in progress. Next, shared resource data is initialized by initialize resources routine 2415 based on the sequences already in progress. In some embodiments, each new sequence submitted for scheduling is examined for any shared resource conflicts by checking each resource using check resource routine 2420 iteratively. If another conflict is found, the sequence is time shifted again by an appropriate amount and all shared resources are rechecked. The process continues until a conflict free schedule is generated. In some embodiments, time shift amounts are calculated precisely to coincide with the points in time at which the utilization factors of the shared resources change. In some embodiments, shared fluidics resources could include fluidics paths (including bottle and processing tank valves, routing valves, pumps, and conduits), processing tanks, and heaters. In some embodiments, the scheduling process is repeated for each newly generated sequence.

In some embodiments, generate tasks module 2425 generates executable tasks from newly scheduled sequences. In some embodiments, generate tasks module 2425 translates the sequence for each newly scheduled drawer from a format suitable for scheduling into a list of tasks with a format suitable for execution. The output of generate tasks module 2425 could include actual task commands, a scheduled start time, a fluid id, and source and destination information.

In some embodiments, collect tasks module 2430 creates a list of ready-to-execute pretreatment tasks for all active slide drawer objects 2162. In some embodiments, all slide drawer objects and their associated fluidics tasks may be monitored to identify ready-to-execute tasks, which are those tasks whose scheduled time has arrived.

Execute tasks module 2435 can execute scheduled tasks. Fluid transfer tasks can be executed indirectly by interfacing with stainer API module 1925 via dynamic task execution threads direct the performance of physical actions on valves and pumps. Other tasks, such as incubation, may be executed directly by starting their countdown timers. In some embodiments, task execution module may spawn several individual fluid transfer task execution threads 2470-1 through 2470-N that may execute in parallel to direct simultaneous fluid transfers along different paths. In some embodiments, each task submitted for execution is examined. For non-transfer tasks, where physical actions are not taken, the start of a new state may be recorded. In some embodiments, for tasks with physical actions, the applicable function in stainer API module 1925 may be invoked. In some embodiments, to execute a fluid transfers, task execution module may dynamically launch an appropriately initialized task execution thread. Each task execution thread can cause performance of lower-level actions by calling an appropriate function in stainer API module 1925.

In some embodiments fluidics transfer functions provided by stainer API module 1925 may have a set of locks to prevent more than one task execution thread from gaining access to exclusive resources such as valves and pumps.

In some embodiments, task execution threads 2470-1 through 2470-N may each execute a fluidics transfer thus allowing multiple simultaneous or overlapping fluidics transfers in stainer 1000. In some embodiments, threads 2470-1 through 2470-N may directly interact with stainer API module 1925 to perform any lower level actions. Errors caused by equipment failure, or other external events encountered while executing an API function may also be handled by task execution threads 2470-1 through 2470-N. In some embodiments, errors may be handled by retrying the fluid transfers, pausing, or halting further processing tank processing, or disabling the processing tank.

In some embodiments, update sequences module 2445 monitors timers, such as incubation timers in stainer 1000, records the completion of non-fluid transfer tasks, updates tasks and sequences as they complete, and detects conditions for rescheduling. When tasks complete, the task sequences for the drawers that originated the completed tasks are updated to reflect the actual machine state so that completed tasks are not repeatedly performed. Accordingly, update sequences module 2445 examines all currently executing tasks and updates the originating sequence to reflect completed tasks. In some situations, a task that cannot be completed because of abnormal conditions may be rescheduled.

In some embodiments, exemplary monitor processing tanks module 2450 executes non-scheduled, periodic actions and tasks such as monitoring processing tank levels and temperatures, and replenishing evaporated target retrieval fluid with de-ionized water to prevent slides 1045 from drying. In some embodiments, deviations from the acceptable incubation tolerances may be logged by monitor processing tanks module 2450. In some embodiments, the level of target retrieval fluid in the processing tanks undergoing heating is also periodically monitored. For example, when the level of de-ionized water in a processing tank drops due to evaporation, it is replenished with more de-ionized water in order to prevent slides 1045 from drying out. In some embodiments, the transfer of de-ionized water to the processing tank may be accomplished through a task thread, which may interface with stainer API 1925.

Figure 6D:
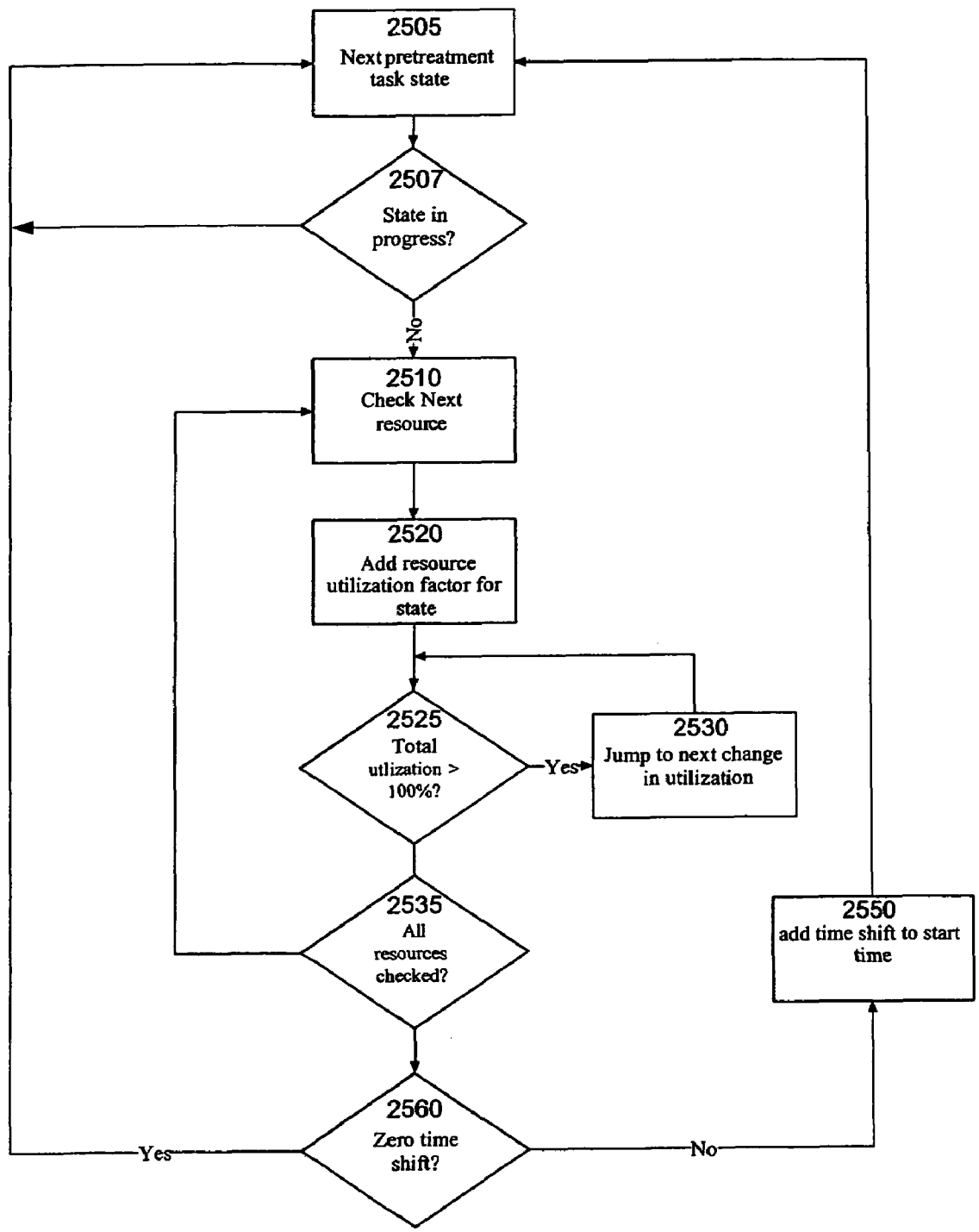
FIG. 6D shows a flowchart of an exemplary method for scheduling and allocating resources for a fluidics scheduler.

FIG. 6D shows a flowchart 2500 of an exemplary algorithm for scheduling and allocating resources for fluidics scheduler 2020. In some embodiments, task pretreatment states are checked in step 2505. States that have already been performed or that are currently in progress are skipped. If a task pretreatment state indicates that the task is not in progress, then each shared resource requested by that task is checked iteratively. The proportion of the next resource used by the task is calculated in step 2510 and added to the utilization factor of the resource in step 2520. If the utilization factor now exceeds 100% in step 2525, then in step 2530 the allocation of the resource is re-scheduled for the next point in time at which the resource utilization factor changes. Steps 2525 and 2530 are repeated until the allocation of the resource can be scheduled without conflict according to some embodiments of the algorithm. If the resource has been scheduled without conflict then steps 2510 through 2535 are repeated until all resources have been allocated. If the allocation of the resources has not caused a time shift in the original start time of the task then the algorithm returns to step 2505 to process the next task. If a time shift to task start time has occurred as a result of resource conflicts, then in step 2550 the task start time is updated to reflect the time shift and the algorithm returns to step 2505 to process the next task In some embodiments, system thread 2110, state process thread 2120, control thread 2130, robotic scheduler 2020, fluidic scheduler 2030, heater thread 214Q, UPS thread 2150 and objects described above may be elements of stainer logic component 1935.

Figure 7:
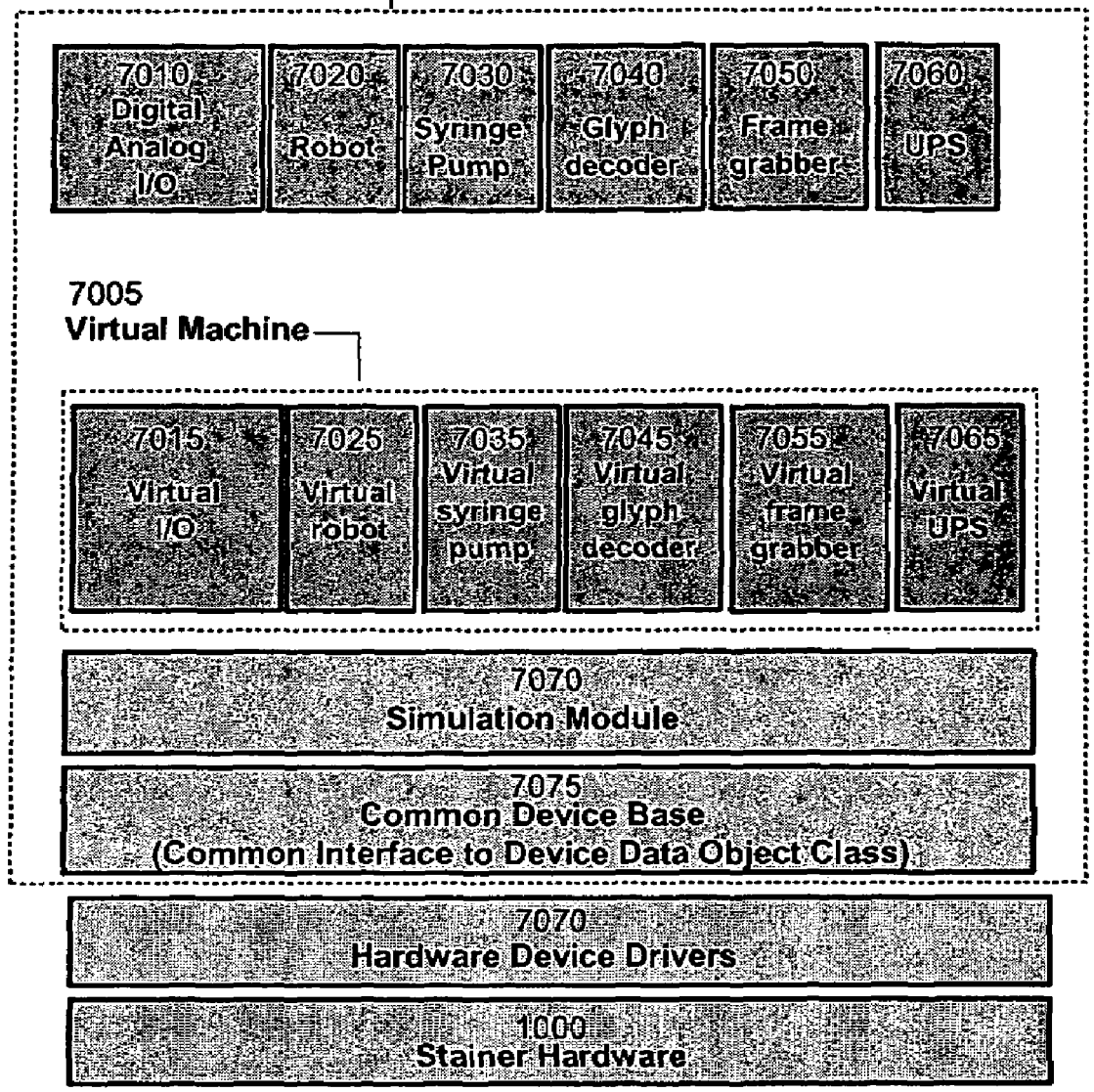
FIG. 7 shows a block diagram of an exemplary applications programming interface ("API") for control of stainer hardware functions.

FIG. 7 shows a block diagram of an exemplary API 7000 for control of hardware sub-systems on stainer 1000. Stainer hardware API may provide an interface to actual hardware components on stainer 1000 that execute the physical tasks. Embodiments of stainer hardware API 1925 provide a common device base interface 7075 and an object architecture that permits device decoupling. Common device base interface 7075 allows external modules to view all hardware devices as sharing some common functionality. For example, from the viewpoint of an external module all devices may be seen to support a "LoadParameters" method, by which devices may load configuration defaults. Device decoupling ensures that software system functionality is unaffected by changes to hardware types and that the effect of any hardware changes is localized and limited to lower level components. Actual physical control over hardware on stainer 1000 is exercised by several hardware device drivers 7080. Thus, a call to stainer hardware API 1930 may result in several device driver invocations to instruct hardware components on stainer 1000 to take actions in consonance with parameters supplied to the call to stainer hardware API 1930.

In some embodiments, stainer hardware API 1930 effects control over real world hardware by using actual device API objects that are tied to the underlying hardware. For example, exemplary stainer hardware API 1930 may include objects related to the implementation of functionality such as digital and analog I/O object 7010, robot object 7020, syringe pump object 7030, glyph decoder object 7040, frame grabber object 7050, and UPS object 7060. A device object may contain data reflecting the state of the underlying hardware, and a functional interface indicating and allowing access to the underlying hardware. For example, robot object 7010 may hold data indicating the current position of robot 1032. In addition, robot object 7010 may provide access to a "move_to(X,Y,Z)" function, which, if invoked, would culminate in robot 1032 moving to the position represented by the co-ordinates (X,Y,Z).

In some embodiments, stainer hardware API 1930 also uses a virtual device object for each actual device API object to provide a mechanism to interface with and support multiple types of hardware device types at run-time, by creating the correct derived object for the actual hardware device type in use. At run-time, a call to stainer hardware API 1930 is translated to the actual hardware device type call using the interface specified by the virtual device object for that device type. Accordingly, exemplary stainer API 1925 may include virtual device objects such as virtual digital and analog I/O 7015, virtual robot 7025, virtual syringe pump 7035, virtual glyph decoder 7045, virtual frame grabber 7055, and virtual UPS 7065. In some embodiments, the objects above and others (not shown) may be part of virtual machine 7005.

If SCS 1310 is in a simulation mode, then the device call is intelligently simulated prior to the actual hardware call, using simulation module 7070. In some embodiments, actual hardware is not exercised in simulation mode; instead simulation module 7070 may return parameters to calling routines based on the underlying hardware that would normally have executed the actions of the API call. In some embodiments, all API calls are routed both to the simulator and to the actual device so that simulation module 7070 can assist in diagnosing hardware behavior.

In some embodiments, digital and analog I/O object 7010 and associated virtual digital & analog I/O object 7015 provide an interface to read or set system input and/or output facilitating control and monitoring of various devices in the system. An instance of the appropriate digital and analog I/O object may be created for each input and/or output present in the system. Access to an input or output may be provided through a digital/analog I/O object. In some embodiments, a master controller may handle the sending of digital and analog data to various boards in the system. In some embodiments, routines may be provided to control access to individual inputs and outputs, verify values written to, or read from an input or output, and to return the name and location of a specific input or output.

In some embodiments, robot object 7020 and virtual robot object 7025 may facilitate control of robot motion related functions, such as the motion of exemplary robot 1032. Virtual robot object 7025 may define a minimal interface to facilitate control of robot motion related functions. If different kinds of robots are supported then one of these objects is created for each robot type. The decision on which one to use is controlled by configuration and selected at load time. In some embodiments, robot object 7020 may provide control of robot movement in all three directions and of the air blower coupled to the robot.

In some embodiments, syringe pump object 7030 provides an interface to access and control the syringe pump, such as exemplary syringe pump 1015, which facilitates the moving of reagents from reagent bottles 1080 onto the slides 1045 being processed. Virtual syringe pump object 7035 may define a minimal interface for access and control of the syringe pump. If different kinds of syringe pump devices are supported then an object instance is created for each type of syringe pump, and the correct object may be selected and instantiated at run time when accessing and loading system configuration parameters.

In some embodiments, glyph decoder object 7040 provides an interface for decoding glyph type encodings, including InfoGlyphs™. Glyph decoding is the process of decoding the glyph in an image that may have been taken by a camera mounted on robot 1032 and acquired by a frame grabber. In some embodiments, after an image has been acquired using the frame grabber, the image is scanned and decoded by glyph decoder object 7040. In some embodiments, decoding may be accomplished by sending image data to a decode library. In some embodiments, the decode library may be furnished by a third party provider. In some embodiments, the image may be filtered before it is sent to the library. In some embodiments, filtering may compensate for the effects of vibration, robot motion and other environmental factors. In some embodiments, any data decoded from the glyph image is returned to the calling process. Virtual glyph decoder object 7045 defines a minimal interface for decoding glyph type encodings. If different kinds of glyph decoders are supported then an object instance is created for each type of glyph decoder.

In some embodiments, frame grabber object 7050 provides an interface to access and control the image acquisition system. In some embodiments, frame grabber object may provide an interface to a sensory hardware board that can acquire images from the camera located on the robot head 1032. In some embodiments, frame grabber hardware may be configured to return images of a given size and format. In some embodiments, an acquired image may be stored in a bit-mapped format in previously allocated frame-buffer memory and made available to the calling routine. In some embodiments, the acquired images may be checked to prevent duplicates. In some embodiments, virtual object 7055 may define a minimal interface. If different kinds of frame grabbers are supported then an object instance is created for each type of frame grabber.

In some embodiments, UPS object 7070 provides an interface to access and control the system UPS 1298 to determine if a power fail state has occurred, to monitor line parameters, and to handle various timing parameters for power reduction, shutdown and user alerts. Virtual UPS object 7075 may define a minimal interface. If different kinds of UPS devices 1298 are supported then an object instance is created for each type of UPS.

Figure 8A:
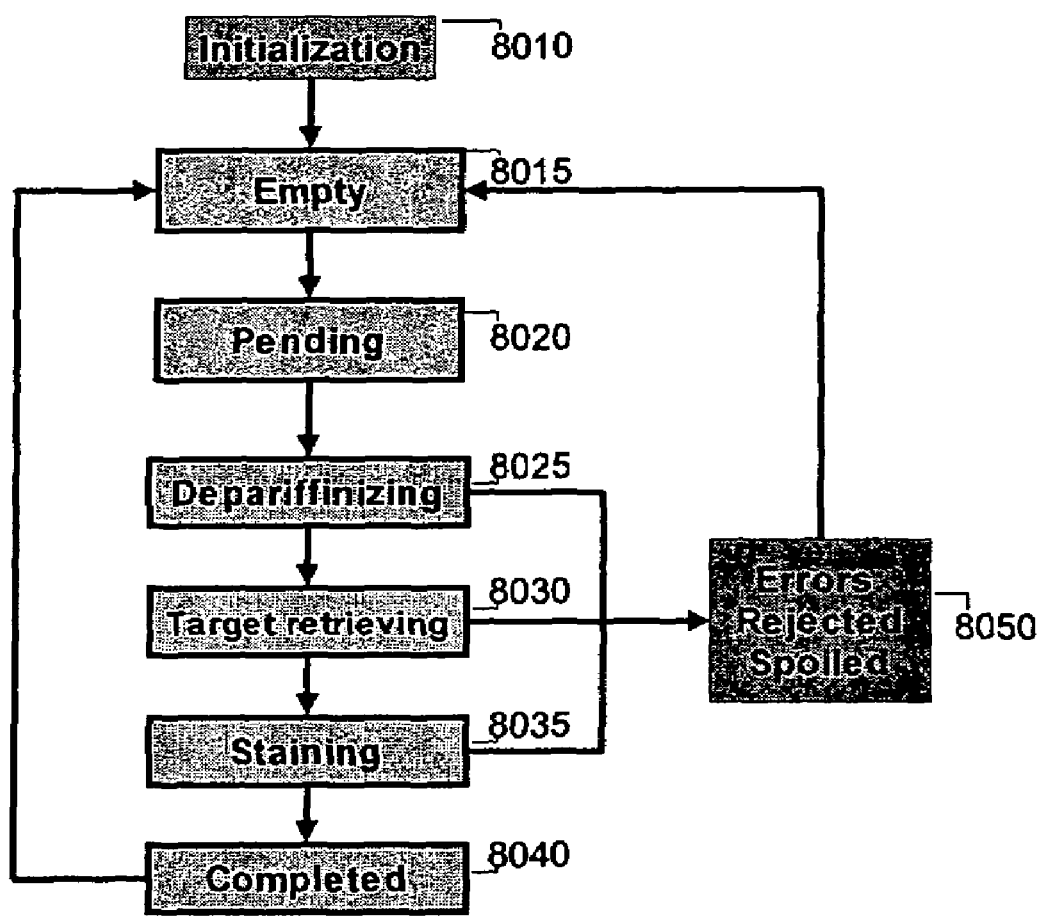
FIG. 8A shows a state transition diagram tracking slide state transitions for an exemplary state process thread.

FIG. 8A shows a state transition diagram tracking slide state transitions for exemplary state process thread 2120. As shown in FIG. 8A, upon initialization in step 8010, state process thread 2120 loads specified slide objects 2166 into a list and enters a continuous loop. During each iteration of the loop, state process thread 2120 may transition multiple slide objects 2166 from One state to another to reflect the processing status of the underlying slides 1045. Accordingly, the state of slide object 2166 may move from state empty 8015, which reflects that no slide is present, to state pending 8020 when a slide 1045 is introduced into the rack. After processing has started, a slide 1045 may move to deparaffinizing state 8025, followed by target retrieving state 8030, and staining state 8035. During any of these states, if a slide 1045 requests fluids or reagents to be allocated, control thread 2130 is informed so that additional actions may be commenced. After staining is complete, the slide 1045 moves to completed state 8040. In some embodiments, each state may have sub-states to reflect individual processes within the states. Treatment protocol errors result in a slide 1045 ending in a final spoiled state 8050. In some embodiments, a slide 1045 spoiled due to treatment protocol errors may continue to move through states normally but may be marked spoiled only at the conclusion of the staining process. Continuing to process a slide 1045 normally allows an operator to make an informed decision regarding the slide sample based on a visual inspection, the actual final state of the slide 1045, the slide log, and the seriousness of the reported deviation from treatment protocol.

Figure 8B:
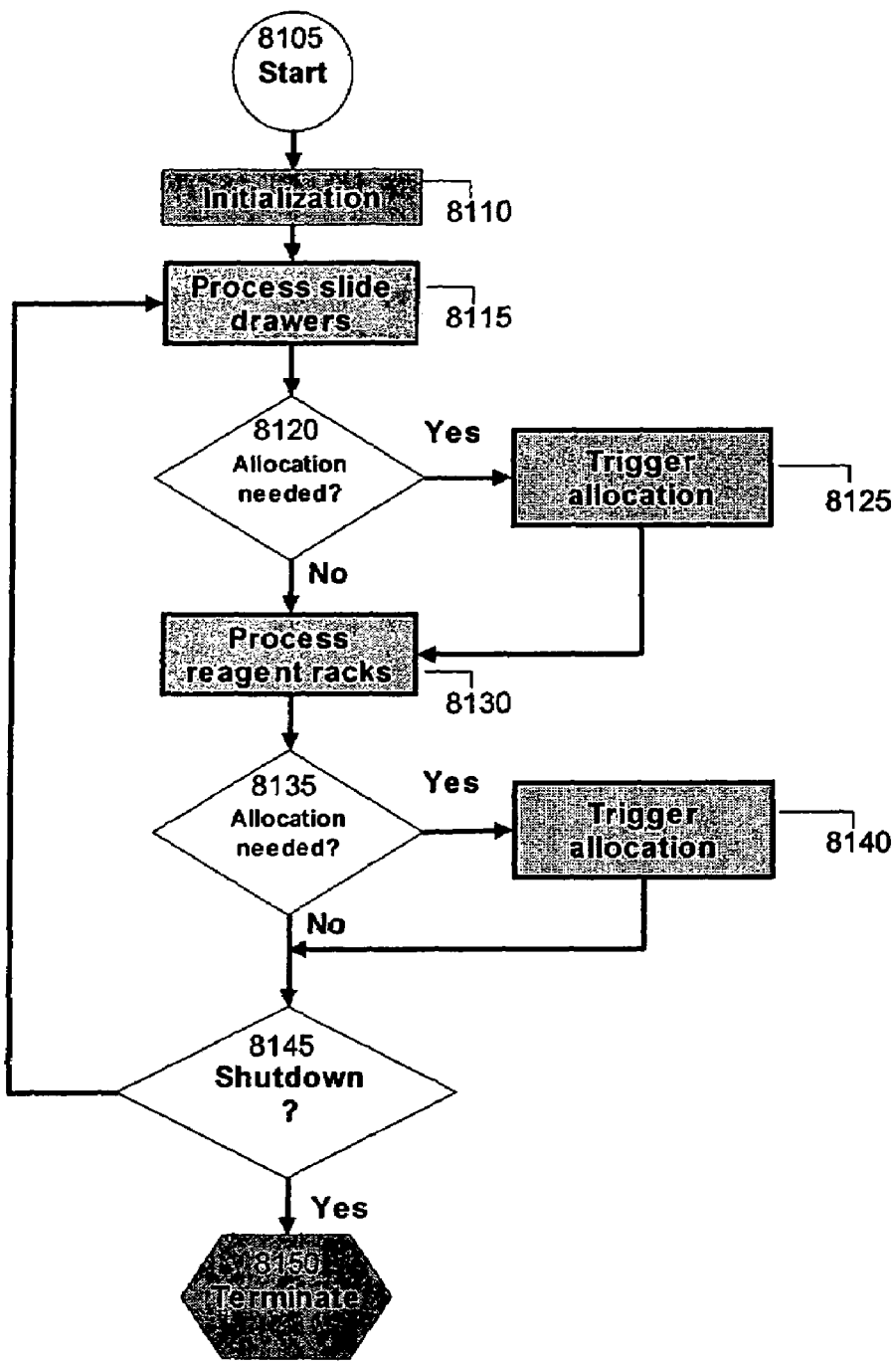
FIG. 8B shows a flowchart for a state process thread instance showing steps in an exemplary method for slide drawer and reagent rack processing.

FIG. 8B shows a flowchart 8100 for a state process thread instance showing steps in an exemplary method for slide drawer and reagent rack processing. In some embodiments, exemplary state process thread 2120 may be a part of stainer logic and schedulers module 1935. As shown in FIG. 8B, state process thread 2120 may start in step 8105. In step 8110, state process thread 2120 may go through an initialization routine during which it loads slide drawer objects 2162 and reagent rack objects 2164 into lists.

In some embodiments, state process thread 2120 may enter a continuous loop following the initialization step during which it periodically processes pending events associated with the loaded slide drawer 2162 and reagent rack objects 2164. For example, in step 8115, exemplary state process thread 2120 may examine slide drawer objects for pending events. If a resource allocation request, such as a pretreatment fluid request, associated with a slide drawer object 2162 is pending in step 8120, then state process thread 2120 may trigger the allocation in step 8125 using control thread 2130. Next, in step 8130 state process thread 2120 may examine reagent rack objects 2164 for pending events. If a resource allocation request, such as a read glyph request, associated with a reagent rack object 2164 is pending in step 8135, then state process thread 2120 may trigger the allocation of the resource in step 8140 using control thread 2130. In some embodiments, the processing of each slide drawer object 2162 and each reagent rack object 2164 may be an autonomous process that is independent from processes for other drawers and racks. If a shutdown is requested in step 8145, the state process thread 2120 terminates in step 8150, otherwise it may return to step 8110 for the next iteration of the loop.

Figure 9:
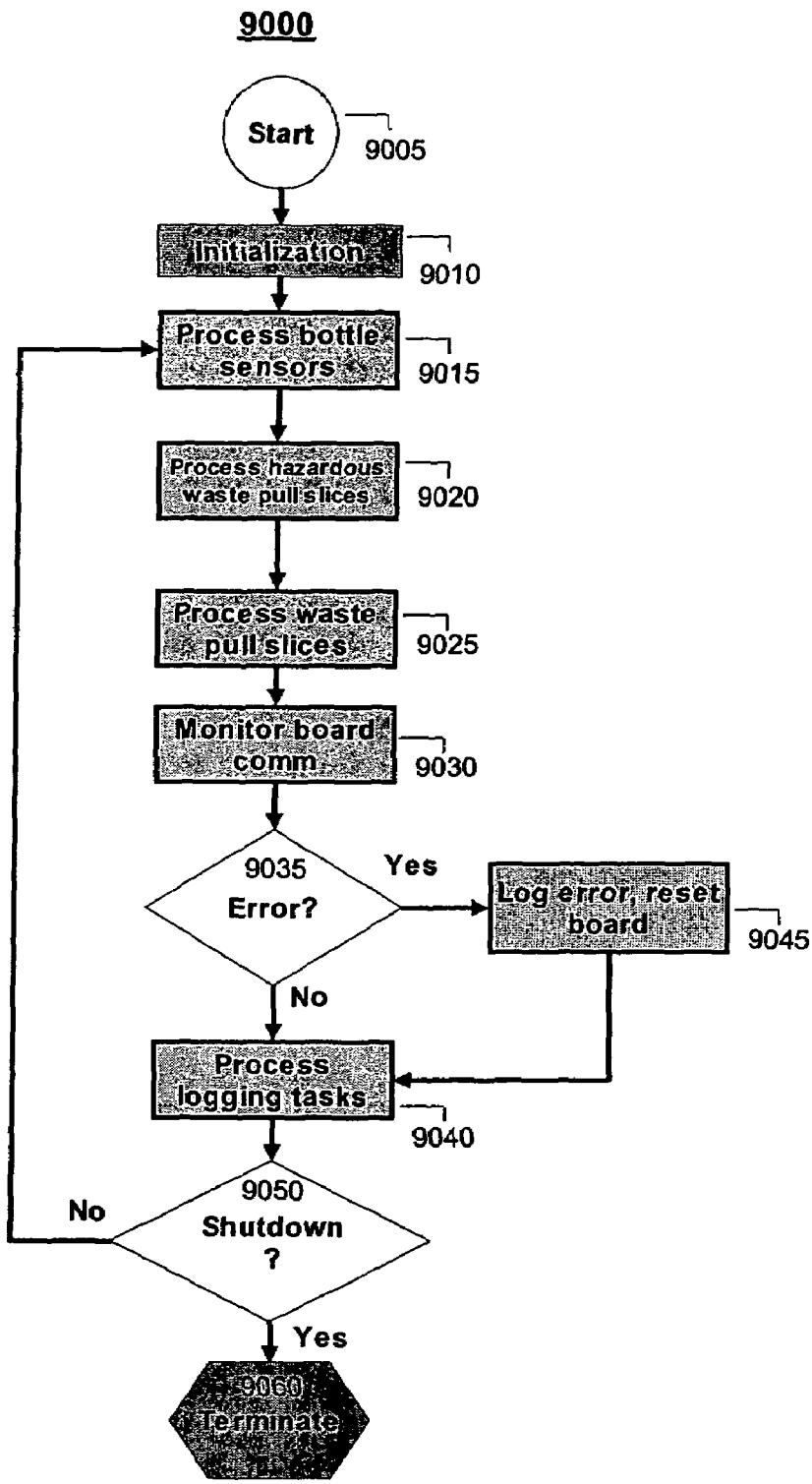
FIG. 9 shows a flowchart for a control thread instance showing steps in an exemplary method for container and waste-processing.

FIG. 9 shows a flowchart for a control thread instance showing steps in an exemplary method for container and waste-processing. In some embodiments, upon starting in step 9005, system thread 2110 proceeds to initialization step 9010 where it loads a list of all input and output addresses and/or ports and initializes sensors. In some embodiments, system thread 2110 may then enter a continuous loop. On each loop iteration, system thread 2110 processes: bottle sensors in step 9015; hazardous waste pull requests in step 9020; waste pull requests in step 9025; monitors input-output ports and on-board communications in step 9030; and processes logging tasks in step 9040.

In some embodiments, in step 9015, system thread 2110 monitors all sensors on containers 1299 on fluidics cart 1295, and provides information about fluid level states on container 1299 to other sub-components of stainer logic module 1935 and to the stainer GUI 1940. In some embodiments, the readings of the bottle sensors may be averaged over a time period to diminish the effect of fluid motion and obtain a more accurate fluid level reading.

In step 9020, hazardous waste pull requests are processed. Hazardous waste pull involves the removal of hazardous waste from stainer processing tanks followed by deposition of the waste into hazardous waste containers in the fluidics cart. In step 9025, normal (non-hazardous) waste requests are processed. In some embodiments, system thread 2110 manages and processes all waste pull requests and ensures that different systems requesting waste pulls get adequate time.

In step 9030, the system thread 2110 also monitors all system boards for loss of communication. In step 9035, if an error such as a communication loss is detected, then the error condition may be logged and the board reset in step 9045. In some embodiments, in step 9040, system thread 2110 may log various sensor conditions at periodic intervals. If system thread detects a shutdown request in step 9050, then the thread terminates in step 9060, otherwise it returns to step 9015 for the next iteration of the loop. In some embodiments, system thread 2110 may run in the background while performing waste pull, container level monitoring, and electronic board communications and status monitoring functions.

Figure 10:
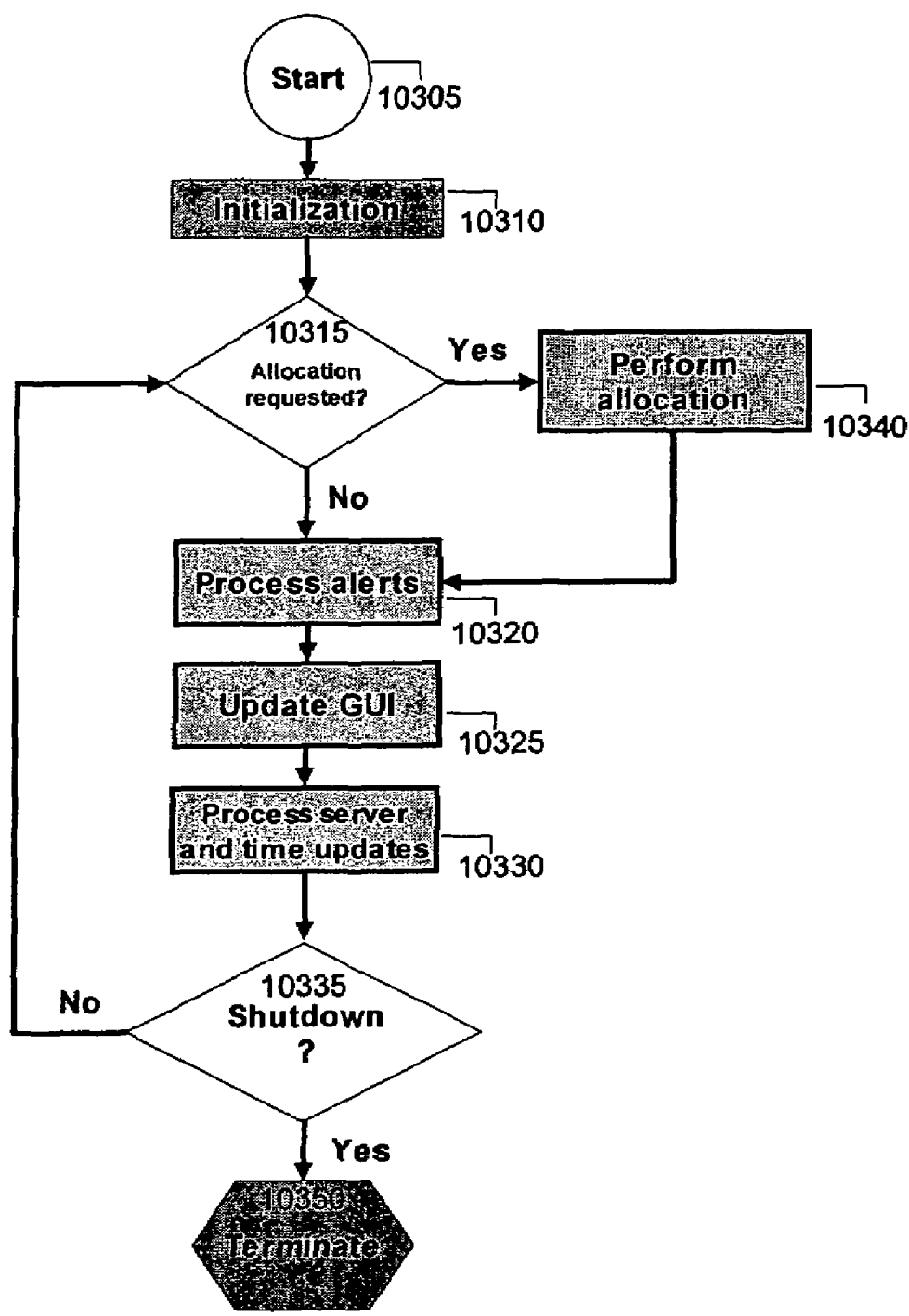
FIG. 10 shows a flowchart for a control thread instance showing steps in an exemplary method for graphical user interface ("GUI") and alert processing according to some embodiments of the present invention.

FIG. 10 shows a flowchart 10000 for a control thread instance showing steps in an exemplary method for Graphical User Interface ("GUI") and alert processing according to some embodiments of the present invention. In some embodiments, control thread 2130 handles reagent allocation, stainer GUI updates and interactions, and server and time updates.

In some embodiments, control thread 2130 starts in step 10305 and performs initialization routines in step 10310 before entering a continuous loop. In some embodiments, initialization routines may include loading lists of objects. On each loop iteration, control thread 2130 checks for requests associated with the objects and processes the requests.

In step 10315, control thread 2130 may check for pending allocation requests. For example, a pending reagent allocation may have been triggered by state process thread 2120 in response to a pending request associated with a slide object 2166. If an allocation request is pending, the allocation may be performed in step 10340. Control thread 2130 can then check for alert requests in step 320 and may update the GUI accordingly in step 10325. In step 10330, server and time updates can be processed. If a shutdown request is detected in step 10335, then in step 10350 control thread 2140 terminates and performs termination related tasks, otherwise it proceeds to step 10315 where it commences another iteration.

Figure 11:
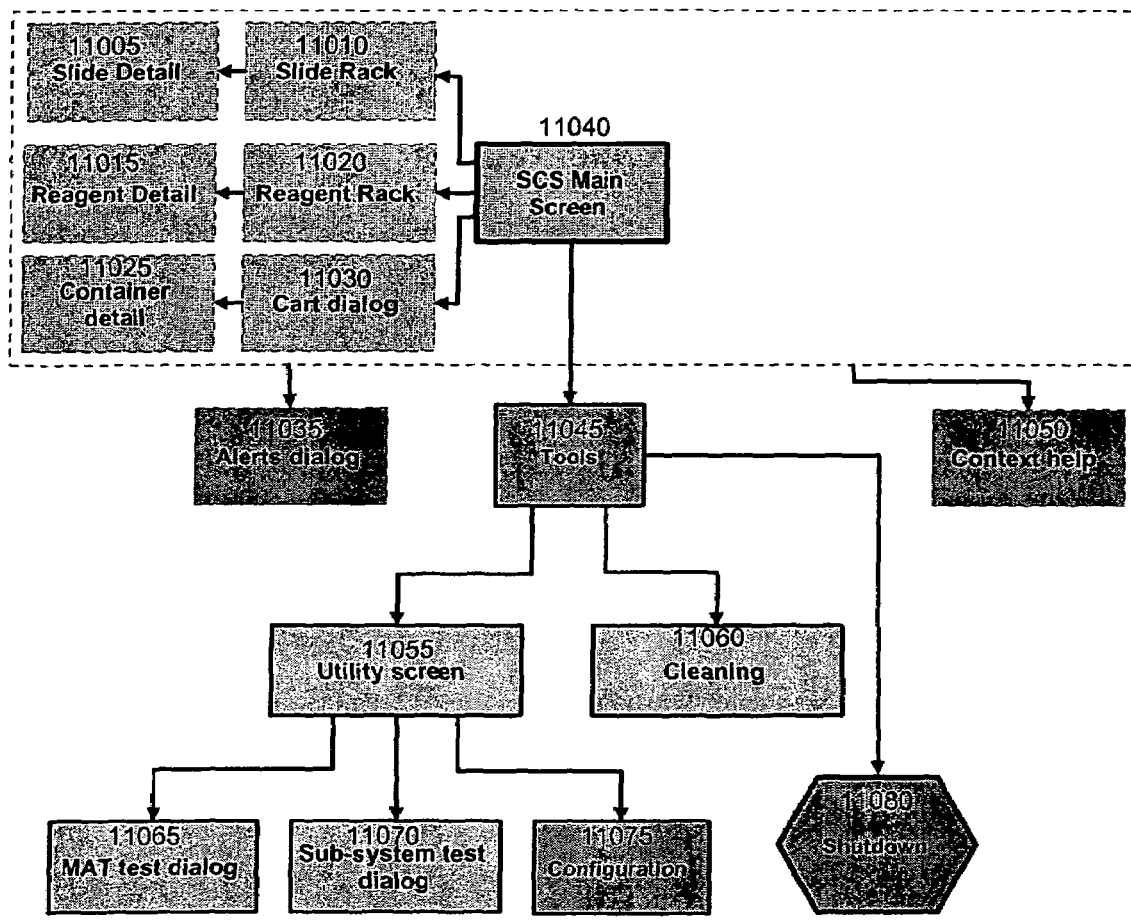
FIG. 11 illustrates an exemplary GUI screen hierarchy for a stainer control software module.

FIG. 11 illustrates an exemplary GUI screen hierarchy 11000 for the Stainer Control Software 1310 according to some embodiments of the present invention. Each stainer, such as exemplary stainer 1000, can have SCS main screen 11040 from which a user may navigate to other screens. In some embodiments, SCS main screen 11040 may provide a snapshot of the status of stainer 1000. For example, SCS main screen 11040 may provide a graphical depiction of slide racks 1065, reagent racks 1060, and fluid cart 1295 with colors used to display the status of slides 1045, reagents in reagent bottles 1080, and fluid containers 1299. In some embodiments, an estimated remaining process time may be displayed for each rack that is currently in use. In some embodiments, the SCS main screen may be automatically returned to from other sub-screens after a defined period of user input inactivity.

In some embodiments, each graphical icon may act as an entry point to a more detailed lower level screen. Thus, SCS main screen 11040 may allow a user access to slide rack screen 11010, which in turn links to slide detail screen 11005. In some embodiments, slide rack screen 11010 may display an individual slide rack 1065 and provide a user with additional options to obtain details of slide rack 1065 or to access slide detail screen 11005.

SCS main screen 11040 may also provide a link to reagent rack screen 11020, which in turn links to reagent detail screen 11015. Reagent rack screen 11020 may display details of reagent racks and provide a user with additional options to obtain details of reagent rack 1060 or to access reagent detail screen 11015. In some embodiments, cart dialog screen 11030, which provides access to container detail screen 11025, may be accessed from SCS main screen 11040. Cart dialog screen 11030 may display details of the fluidics cart and provide a user with additional options to obtain fluidics cart related details or to access container detail screen 11025.

SCS main screen 11040, slide rack screen 11010, slide detail screen 11005, reagent rack screen 11020, reagent detail screen 11015, cart dialog screen 11030, and container detail screen 11025 may represent typical screens that can be accessed by SCS operators during normal operation of stainer 1000. In some embodiments, SCS main screen 11040 receives GUI updates from control thread 2130. As slide object 2166, slide drawer object 2162, reagent object 2168, and reagent racks object 2164 change states, the GUI corresponding to SCS main screen 11040 can be updated to display the current state.

Tools screen 11045 provides access to utility screen 11055, which allows access to a MAT test dialog screen 11065, subsystem test dialog screen 11070, and stainer configuration screen 11075. In some embodiments, screens below tools screen 11045 provide access to stainer related diagnostic, configuration, test, cleaning and administrative functions, and may be utilized when stainer 1000 is in an idle mode. In some embodiments, an operator may be requested to enter a tool access password to gain access to dialogs and screens below tools screen 11045. In some embodiments, successful access to tools screen 11045 and lower level screens may take stainer 1000 out of a normal run mode and place it in an idle state in preparation for further user commands. Tools screen 11045 also provides access to a stainer cleaning menu 11060 and a shutdown screen 11080. In some embodiments, alert screen 11035 may be a pop-up screen that may pop-up or flash whenever stainer 1000 issues an operator alert. In some embodiments, at every screen, a context sensitive help screen 11050 allows an operator to access help relevant to the function that the operator is performing.

Figure 12:
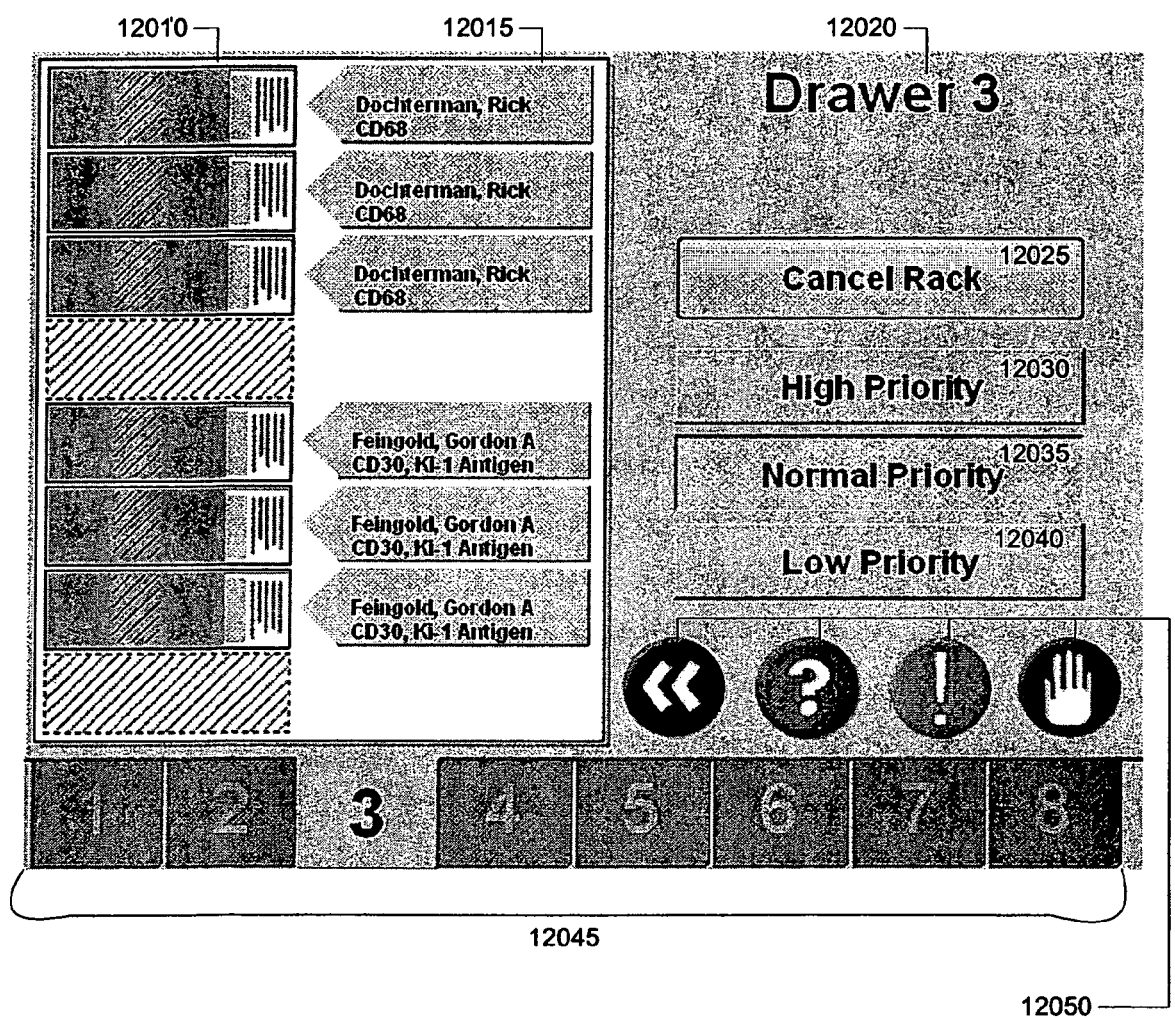
FIG. 12 shows an exemplary slide rack dialog screen according to some embodiments of the present invention.

FIG. 12 shows exemplary slide rack dialog screen 11010 according to some embodiments of the present invention. As shown in FIG. 12, slide rack dialog screen displays iconic representations 12010 for slides 1045 in one of the slide racks

12045. An exemplary label 12020 indicates that the slides 1045 displayed in FIG. 12 belong to slide rack 3. In some embodiments, the slide icons may be color coded to indicate slide status and shaded areas without an icon may indicate empty rack positions. Details of each slide 1045 are shown in slide detail area 12015 and additional details about a particular slide 1045 may be obtained by selecting that slide. Slide rack dialog screen 11010 provides an operator with options to: cancel a rack of slides 12025; set slides to high priority 12030; set slides to normal priority 12035; or set slides to low priority 12040.

In some embodiments, a set of icons 12050 provide access to other screens from any screen in a stainer. For example, the wrench icon provides access to tools screen 11045; the question mark icon provides access to context sensitive help screen 11050 for slide rack dialog screen 11010; an exclamation icon provide access to Alerts dialog screen 11035; and a hand icon provides access to a stainer stop dialog screen if stainer 1000 is currently actively processing slides. In some embodiments, standard GUI components, such as those available in Microsoft Windows, may be used to display the information held in slide object 2166, reagent object 2168, slide drawer object 2162, and reagent rack object 2164. In some embodiments, stainer 1000 may provide a touch screen on the front panel from which a user may access the various screens.

Figure 13:
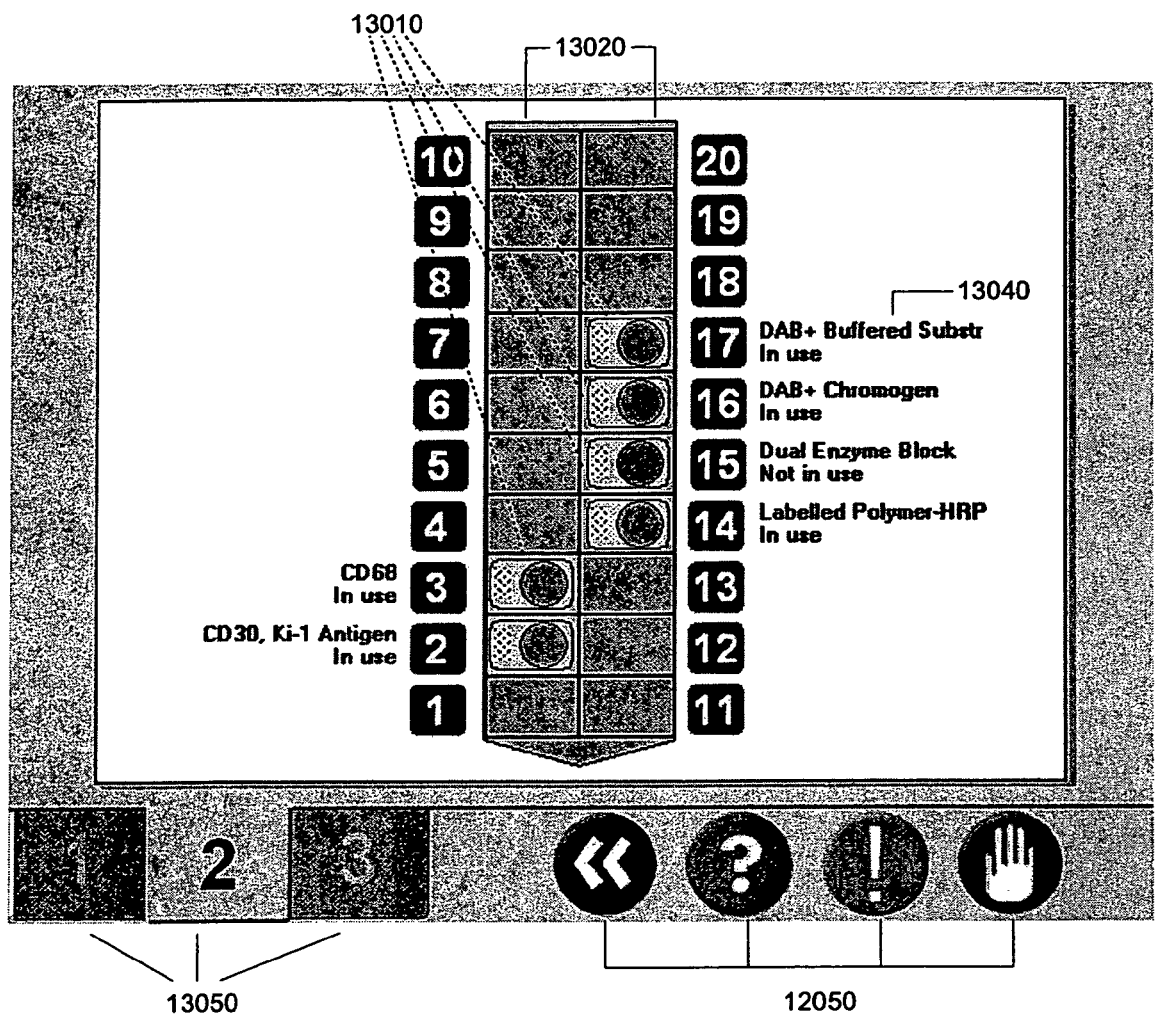
FIG. 13 shows an exemplary reagent rack dialog screen according to some embodiments of the present invention.

FIG. 13 shows an exemplary reagent rack dialog screen 11020 according to some embodiments of the present invention. As shown in FIG. 13, reagent rack dialog screen 11020 displays an icon 13020 indicating the status of one of reagent racks 13050. For example, FIG. 13 shows details for reagent rack 2. Additionally, icons for individual reagent bottles 13010 may indicate the status of individual bottles on reagent rack 1060 and may provide an access point for an operator to get reagent bottle details. In some embodiments, the icons for the bottles may be color coded to indicate the bottle status. In some embodiments, details 13040 of the content of each bottle in the reagent rack 1060 may be displayed. Icon set 12050 may provide access to other screens for stainer 1000.

Figure 14:
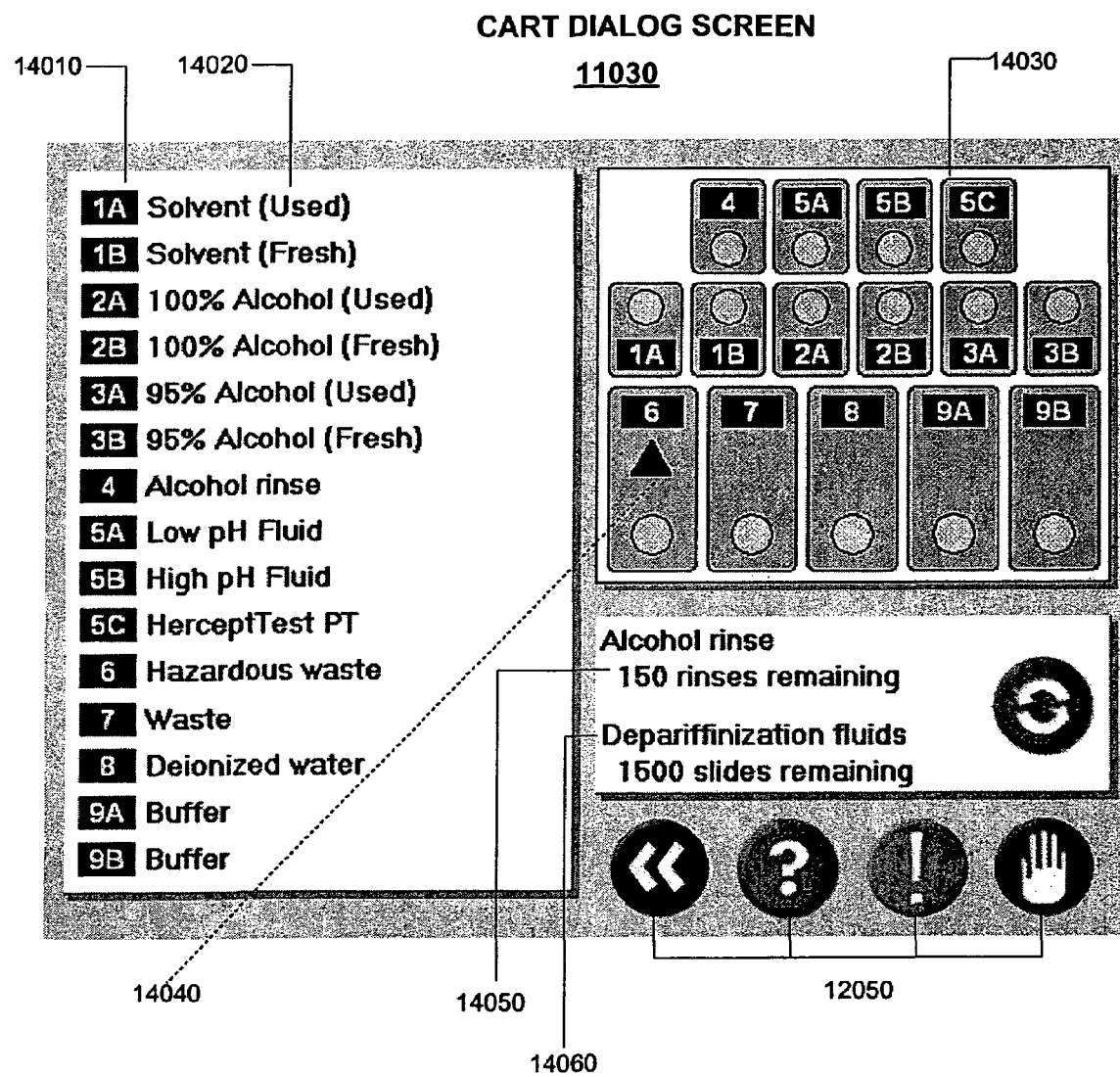
FIG. 14 shows an exemplary cart dialog screen according to some embodiments of the present invention.

FIG. 14 shows an exemplary cart dialog screen 11030 according to some embodiments of the present invention. As shown in FIG. 14, cart dialog screen 11030 may display icons for containers 14030 on the fluidics cart. In some embodiments, a hazardous materials icon 14040 may flag a particular container 1299 on fluidics cart 1295 as containing hazardous materials. In some embodiments, for each container 1299 in fluidics cart 1295 container position indicator 14010 and description 14020 details the contents of the container. In some embodiments, a dialog box containing messages 14050 and 14060 may provide an operator with information regarding the quantity of fluid remaining.

An improved method and apparatus for pre-treatment of biological samples have been disclosed and described according to some preferred exemplary embodiments. Those skilled in the art can now appreciate, from the foregoing description, that the broad techniques of the embodiments of the present invention can be implemented in a variety of forms. Therefore, while the embodiments of this invention have been described in connection with particular examples thereof, the true scope of the embodiments of the present invention should not be so limited since many variations and equivalents of the method and the apparatus may be carried out without departing from the scope of the invention.

Further, methods described herein according to embodiments of the invention may conveniently be implemented using program modules, hardware modules, or a combination of program and hardware modules. Such modules, when executed, may perform the steps and features disclosed herein, including those disclosed with reference to the exemplary flow charts shown in the figures. The operations, stages, and procedures described above and illustrated in the accompanying drawings are sufficiently disclosed to permit one of ordinary skill in the art to practice the invention. Moreover, there are many computing elements, programming languages and tools, and operating systems that may be used in practicing embodiments of the instant invention and, therefore, no detailed computer program could be provided that would be applicable to these many different systems. Each user of a particular system will be aware of the language, hardware, and tools that which are most useful for that user's needs and purposes.

The above-noted features and aspects of the present invention may be implemented in various environments. Such environments and related applications may be specially constructed for performing the various processes and operations of the invention, or they may include a general-purpose system or computing platform selectively activated or reconfigured by program code to provide the functionality.

Embodiments of the present invention also relate to computer readable media that include program instructions or program code for performing various computer-implemented operations based on the methods and processes of embodiments of the invention. The program instructions may be those specially designed and constructed for the purposes of the invention, or they may be of the kind well known and available to those having skill in the computer software arts. Examples of program instructions include, for example, machine code, such as produced by a compiler, and files containing a high-level code that can be executed by the computer using an interpreter.

Other embodiments of the invention will be apparent to those skilled in the art from consideration of the specification and practice of the embodiments of the invention disclosed herein. It is intended that the specification and examples be considered as exemplary only, with a true scope and spirit of the invention being indicated by the following claims. As such, the invention is limited only by the following claims.

What is claimed is:

1. A method for processing slides, comprising:
    introducing one or more new slides into one of a plurality of stainers;
    obtaining slide identification information for at least one of the one or more new slides;
    obtaining a treatment protocol sequence for the at least one of the one or more new slides from a centralized database associated with the plurality of stainers using the slide identification information;
    determining if an adequate quantity of reagents to be used in the treatment protocol sequence is available on the one of the plurality of stainers; and
    processing at the one of the plurality of stainers the at least one of the one or more new slides according to commands in a command list corresponding to the treatment protocol sequence for the at least one of the one or more new slides.

2. The method of claim 1, wherein the one or more new slides are introduced into the one of the plurality of stainers concurrent with the processing of any old slides previously presented to the one of the plurality of stainers.

3. The method of claim 1, wherein obtaining slide identification information for the at least one of the one or more new slides comprises reading a label containing the encoded slide identification information affixed to the at least one of the one or more new slides.

4. The method of claim 3, wherein obtaining slide identification information includes reading a glyph that contains the encoded slide identification information.

5. The method of claim 1, wherein obtaining slide identification information for the at least one of the one or more new slides further comprises reading a radio frequency identification tag associated with the at least one of the one or more new slides.

6. The method of claim 1, wherein the centralized database associated with the plurality of stainers may be accessed for other purposes including slide pre-processing, data entry, queries, and report generation concurrent with the processing of any old slides previously presented to the one of the plurality of stainers.

7. The method of claim 6, wherein the centralized database is resident on a server concurrently accessed by one or more client devices over a client-server network for slide pre-processing, data entry, and report generation.

8. The method of claim 6, wherein slide pre-processing comprises creating or updating a slide record pertaining to a slide in the centralized database associated with the plurality of stainers and generating labels containing slide identification information for affixment to slides.

9. The method of claim 1 wherein the centralized database is resident on a server accessed by clients including the plurality of stainers over a client-server network.

10. The method of claim 9, wherein a current back-up copy of the centralized database is maintained on a separate server.

11. The method of claim 1, wherein obtaining a treatment protocol sequence for the at least one of the one or more new slides from the centralized database associated with the plurality of stainers using the slide identification information further comprises retrieving a slide record containing the treatment protocol sequence for the at least one of the one or more new slides.

12. The method of claim 1, wherein the treatment protocol sequence for the at least one of the one or more new slides is obtained prior to the commencement of processing of the at least one of the one or more new slides.

13. The method of claim 1, wherein processing the at least one of the one or more new slides according to commands in a command list corresponding to the treatment protocol sequence for the at least one of the one or more new slides is performed autonomously by the one of the plurality of stainers.

14. The method of claim 1, wherein processing the at least one of the one or more new slides according to commands in a command list corresponding to the treatment protocol sequence for the at least one of the one or more new slides further comprises:
creating a list of stainer commands corresponding to individual processing steps in the treatment protocol sequence for the at least one of the one or more new slides; and
executing commands in the command list in order on the one of the plurality of stainers on the at least one of the one or more new slides.

15. The method of claim 14, wherein executing commands in the command list in order on the one of the plurality of stainers on the at least one of the one or more new slides further comprises:
determining if prerequisites for execution of a next command on the command list have been satisfied;
taking corrective action if prerequisites for execution of the next command in order on the command list have not been satisfied; and
executing the next command when prerequisites for execution of that command have been satisfied.

16. The method of claim 15, wherein executing the next command when prerequisites for execution of that command have been satisfied further comprises:
applying a reagent to the at least one of the one or more new slides; and
updating at least one database record in the centralized database associated with the plurality of stainers to reflect the completion of execution.

17. The method of claim 16, wherein updating at least one database record in the centralized database associated with the plurality of stainers to reflect the completion of execution further comprises updating at least one database record elected from a group consisting of:
a slide log to reflect the actions taken on the at least one of the one or more new slides,
a reagent log to reflect the actions taken on a reagent, and
a stainer log to reflect the actions taken by the one of the plurality of stainers.

18. The method of claim 15, wherein taking corrective action if prerequisites for execution of the next command in order on the command list have not been satisfied further comprises:
alerting an operator about prerequisites for the next command that have not been satisfied; and
monitoring unsatisfied prerequisites for the next command for changes in status.

19. A method for processing slides, comprising: introducing one or more new slides into one of a plurality of stainers;
obtaining slide identification information for at least one of the one or more new slides;
obtaining a treatment protocol sequence for the at least one of the one or more new slides from a centralized database associated with the one of the plurality of stainers using the slide identification information; and
processing the at least one of the one or more new slides according to commands in a command list corresponding to the treatment protocol sequence for the at least one of the one or more new slides, wherein the one or more new slides are introduced into the one of the plurality of stainers concurrent with processing of any old slides previously presented to the one of the plurality of stainers.

20. The method of claim 19, wherein obtaining slide identification information for the at least one of the one or more new slides comprises reading a label containing the encoded slide identification information affixed to the at least one of the one or more new slides.

21. The method of claim 20, wherein obtaining slide identification information includes reading a glyph that contains the encoded slide identification information.

22. The method of claim 19, wherein obtaining slide identification information for the at least one of the one or more new slides further comprises reading a radio frequency identification tag associated with the at least one of the one or more new slides.

23. The method of claim 19, wherein the centralized database associated with the one of the plurality of stainers may be accessed for other purposes including slide pre-processing, data entry, queries, and report generation concurrent with the processing of any old slides previously presented to the one of the plurality of stainers.

24. The method of claim 23, wherein the centralized database associated with the one of the plurality of stainers is a database and is resident on a server concurrently accessed by one or more client devices over a client-server network for slide pre-processing, data entry, and report generation.

25. The method of claim 23, wherein slide pre-processing comprises creating or updating a slide record pertaining to a slide in the centralized database associated with the one of the plurality of stainers and generating labels containing slide identification information for affixment to slides.

26. The method of claim 19, wherein the centralized database associated with the one of the plurality of stainers is a database serving the plurality of stainers.

27. The method of claim 26, wherein the centralized database is resident on a server accessed by clients including the plurality of stainers over a client- server network.

28. The method of claim 27, wherein a current back-up copy of the centralized database is maintained on a separate server.

29. The method of claim 19, wherein obtaining a treatment protocol sequence for the at least one of the one or more new slides from the centralized database associated with the one of the plurality of stainers using the slide identification information further comprises retrieving a slide record containing the treatment protocol sequence for the at least one of the one or more new slides.

30. The method of claim 19, wherein the treatment protocol sequence for the at least one of the one or more new slides is obtained prior to the commencement of processing of the at least one of the one or more new slides.

31. The method of claim 19, wherein processing the at least one of the one or more new slides according to commands in a command list corresponding to the treatment protocol sequence for the at least one of the one or more new slides is performed autonomously by the one of the plurality of stainers.

32. The method of claim 19, wherein processing the at least one of the one or more new slides according to commands in a command list corresponding to the treatment protocol sequence for the at least one of the one or more new slides further comprises:
    creating a list of stainer commands corresponding to individual processing steps in the treatment protocol sequence for the at least one of the one or more new slides; and
    executing commands in the command list in order on the one of the plurality of stainers on the at least one of the one or more new slides.

33. The method of claim 32, wherein executing commands in the command list in order on the one of the plurality of stainers on the at least one of the one or more new slides further comprises:
    determining if prerequisites for execution of a next command on the command list have been satisfied;
    taking corrective action if prerequisites for execution of the next command in order on the command list have not been satisfied; and
    executing the next command when prerequisites for execution of that command have been satisfied.

34. The method of claim 33, wherein executing the next command when prerequisites for execution of that command have been satisfied further comprises:
    applying a reagent to the at least one of the one or more new slides; and
    updating at least one database record in the centralized database associated with the one of the plurality of stainers to reflect the completion of execution.

35. The method of claim 34, wherein updating at least one database record in the centralized database associated with the one of the plurality of stainers to reflect the completion of execution further comprises updating at least one database record elected from a group consisting of:
    a slide log to reflect the actions taken on the at least one of the one or more new slides,
    a reagent log to reflect the actions taken on a reagent, and
    a stainer log to reflect the actions taken by the one of the plurality of stainers.

36. The method of claim 33, wherein determining if the prerequisites for execution of the next command on the command list have been satisfied further comprises:
    obtaining information on reagents to be used in executing the next command; and
    determining if an adequate quantity of the reagent is available.

37. The method of claim 33, wherein taking corrective action if prerequisites for execution of the next command in order on the command list have not been satisfied further comprises:
    alerting an operator about prerequisites for the next command that have not been satisfied; and
    monitoring unsatisfied prerequisites for the next command for changes in status.

* * * * *

UNITED STATES PATENT AND TRADEMARK OFFICE
CERTIFICATE OF CORRECTION

| | | |
|---|---|---|
| PATENT NO. | : 7,603,201 B2 | Page 1 of 1 |
| APPLICATION NO. | : 11/338524 | |
| DATED | : October 13, 2009 | |
| INVENTOR(S) | : Gordon Alan Feingold et al. | |

It is certified that error appears in the above-identified patent and that said Letters Patent is hereby corrected as shown below:

Title Page, item (57) Abstract, line 3, after "within the apparatus" insert -- are disclosed. --.

In claim 9, column 51, line 24, insert -- , -- after the number "1".

Signed and Sealed this

Eighth Day of June, 2010

David J. Kappos
*Director of the United States Patent and Trademark Office*